(12) United States Patent
West et al.

(10) Patent No.: US 8,791,073 B2
(45) Date of Patent: Jul. 29, 2014

(54) PEPTIDE-MODIFIED POLYURETHANE COMPOSITIONS AND ASSOCIATED METHODS

(75) Inventors: Jennifer L. West, Pearland, TX (US);
Ho-Wook Jun, Houston, TX (US);
Lakeshia J. Taite, Grove Hill, AL (US)

(73) Assignee: William Marsh Rice University, Houston, TX (US)

( * ) Notice: Subject to any disclaimer, the term of this patent is extended or adjusted under 35 U.S.C. 154(b) by 508 days.

(21) Appl. No.: 11/129,941

(22) Filed: May 16, 2005

(65) Prior Publication Data
US 2006/0067909 A1    Mar. 30, 2006

Related U.S. Application Data

(60) Provisional application No. 60/571,313, filed on May 14, 2004.

(51) Int. Cl.
| | | |
|---|---|---|
| A61K 38/00 | (2006.01) | |
| C07K 7/06 | (2006.01) | |
| C08G 18/10 | (2006.01) | |
| C08L 75/04 | (2006.01) | |
| A61K 38/17 | (2006.01) | |
| C08G 18/08 | (2006.01) | |
| C08G 18/64 | (2006.01) | |
| A61K 47/48 | (2006.01) | |

(52) U.S. Cl.
CPC . *A61K 38/00* (2013.01); *C07K 7/06* (2013.01); *A61K 38/17* (2013.01); *C08G 18/08* (2013.01); *C08G 18/6446* (2013.01); *C08L 75/04* (2013.01); *A61K 47/48192* (2013.01); *A61K 47/48215* (2013.01); *A61K 47/48715* (2013.01)
USPC .......... 514/19.1; 530/300; 530/421; 525/54.1

(58) Field of Classification Search
CPC . A61K 38/00; A61K 38/17; A61K 47/48192; A61K 47/48215; A61K 47/48715; C07K 7/06; C08G 18/10; C08G 18/6446; C08L 75/04
USPC .................. 530/300, 421; 525/54.1; 514/19.1
See application file for complete search history.

(56) References Cited

U.S. PATENT DOCUMENTS

| | | | |
|---|---|---|---|
| 5,399,665 A | | 3/1995 | Barrera et al. |
| 5,403,750 A | | 4/1995 | Braatz et al. |
| 5,733,538 A | * | 3/1998 | Riffle ......................... 424/78.08 |
| 6,054,504 A | | 4/2000 | Dalla Riva Toma |
| 6,210,441 B1 | * | 4/2001 | Flodin ......................... 623/13.18 |
| 6,280,765 B1 | | 8/2001 | Gueret |
| 6,313,254 B1 | | 11/2001 | Meijs et al. |
| 6,428,579 B1 | | 8/2002 | Valentini |
| 6,437,073 B1 | | 8/2002 | Gunatillake et al. |
| 2003/0185798 A1 | | 10/2003 | Park |
| 2003/0203915 A1 | | 10/2003 | Fang et al. |

OTHER PUBLICATIONS

Sun X, Sheardown H, Tengvall P, Brash JL, Peptide modified gold-coated polyurethanes as thrombin scavenging surfaces, Journal of Biomedical Material Research, 2000, 49: 66-78.*
Guan J, Sacks MS, Beckman EJ, Wagner WR, Synthesis, characterization, and cytocompatibility of elastomeric, biodegradable poly9ester-urethane)ureas based on poly(caprolactone) and putrescine, Journal of Biomedical Material Research, 2002, 61: 493-503.*
Jun Ho-Wook, Development of Bioactive Polyurethaneureas to Support Endothelialization, Dissertation, Rice University, Apr. 2004.*
Lin H-B, Sun W, Mosher DF, Garcia-Echeverria C, Schaufelberger K, Lelkes PI, Cooper SL, Synthesis, surface, and cell-adhesion properties of polyurethane containing covalently grafted RGD-peptides, Journal of Biomedical Materials Research, 1994, 28(3): 329-342.*
Definition of grafted, from www.dictionary.com, pp. 1-5, Accessed Jul. 16, 2008.*
Definition of incorporation from www.dictionary.com, pp. 1-4. Accessed Feb. 9, 2009.*
Definition of Graft from www.dictionary.com, pp. 1-7. Accessed Feb. 9, 2009.*
Ho-Wook Jun & Jennifer West, J. Biomater. Sci. Polymer Edn, 15(1) 73-94 (2004).
Ho-Wook Jun & Jennifer West, J Biomed. Mater. Res. B. Appl. Biomater. 72(1) 131-9 (2005).
Ho-Wook Jun, et al., Biomacromolecules. 6(2) 838-44 (2005).
Kytai Truong Nguyen & Jennifer West, Biomaterials, 23 4307-14 (2002).
Pathiraja A. Gunatillake & Raju Adhikari, European Cells and Materials, 5 1-16 (2003).
Ho-Wook Jun & Jennifer West, Tissue Engineering, 11(7/8) 1133-40 (2005).

* cited by examiner

*Primary Examiner* — Julie Ha
(74) *Attorney, Agent, or Firm* — Reed Smith LLP; Robert R. Riddle

(57) ABSTRACT

Peptide-modified polyurethanes comprising the reaction product of an isocyanate, a chain extender, and a peptide are provided. Also provided processes for making a peptide-modified polyurethane comprising: providing an isocyanate; providing a chain extender; providing a peptide; and allowing the isocyanate, chain extender, and peptide to react thereby forming the peptide-modified polyurethane, as well as methods for treating a subject comprising: providing a peptide-modified polyurethane that comprises the reaction product of an isocyanate, a chain extender, and a peptide; and administering the peptide-modified polyurethane to the subject.

13 Claims, 75 Drawing Sheets

Step I

Step II

US 8,791,073 B2

PEPTIDE-MODIFIED POLYURETHANE COMPOSITIONS AND ASSOCIATED METHODS

CROSS-REFERENCE TO RELATED APPLICATION

This Application claims priority to U.S. Provisional Patent Application Ser. No. 60/571,313 filed on May 14, 2004 and entitled "Peptide-Modified Polyurethane Compositions and Methods."

STATEMENT OF GOVERNMENT INTEREST

The present invention was developed under grants from the National Science Foundation (Grant Nos. HRD-9817555, 0114264, and BES-9875607) and National Institutes of Health (Grant No. R01-HL60485). The U.S. Government may have certain rights to the invention.

BACKGROUND

The present invention generally relates to peptide-modified polyurethane compositions and methods of using such compositions. These compositions have improved properties that make them useful for a variety of applications, including, in particular, the manufacture of medical devices, articles, or implants that contact living tissues or bodily fluids.

Polyurethanes represent a major class of synthetic polymers that have been evaluated for use with a variety of medical implants. Polyurethanes have favorable mechanical properties (e.g., high tensile strength, tear and abrasion resistance, and stability in biological environments) and are generally biocompatible. Accordingly, polyurethanes are used with medical implants such as cardiac pacemakers, catheters, implantable prostheses, cardiac assist devices, heart valves, and vascular grafts. The favorable mechanical properties of some polyurethanes can be attributed to their two-phase morphology, which is derived from microphase separation of soft and hard polymer segments. The soft segment has a low glass transition temperature (Tg), and the hard segment has a high Tg. For polyurethanes used with certain medical implants, the soft segments may be formed from a polyether polyol such as polytetramethylene oxide (PTMO), and the hard segments may be derived from a diisocyanate such as 4,4'-methylene-diphenyl diisocyanate (MDI) and a polyol chain extender such as 1,4-butanediol.

Vascular grafts are a type of medical implant in which synthetic polymers are useful. Certain vascular diseases often result in a need to open, replace, or bypass diseased or damaged blood vessel segments. In these situations, a graft may be used to direct blood flow around occluded segments of the vasculature, commonly referred to as bypass grafting. In coronary artery bypass grafting (CABG), occluded coronary arteries can be replaced with autologous tissue such as saphenous veins. But, some patients may not have suitable donor tissue, e.g., due to peripheral vascular disease or prior surgery, and a synthetic blood vessel substitute or graft may be required.

Synthetic polymers such as ePTFE (expanded polytetrafluoroethylene), Dacron (polyethylene teraphthalate), and microporous polyurethanes have been developed for use with synthetic grafts and other medical implants. In large-diameter (e.g., >6 mm) applications, these synthetic polymers have been successfully used as vascular grafts, but generally are not suitable for small-diameter applications such as CABG. In small-diameter applications, synthetic grafts often become occluded, decreasing the patency of the graft. Similarly, grafts with low blood flow are more susceptible to patency failure as compared to those in high blood flow. Thus, synthetic grafts are used infrequently for bypass or reconstructive procedures that require small diameters, such as the coronary artery and arteries below the knee.

Compliance also affects the function of small-diameter synthetic grafts. Vascular compliance is the ability of a blood vessel wall to expand and contract passively with changes in pressure and constitutes an important function of large arteries and veins. The compliance of a blood vessel generally is a structural property, which depends on the geometry (diameter and wall thickness) of the blood vessel, rather than a material property. To avoid discontinuity of blood-flow velocity, the compliance of a graft should match the compliance of the vessel it is replacing. Generally, smaller synthetic grafts are unable to meet the compliance requirements of small-diameter vessels.

Endothelialization of synthetic grafts may improve graft patency and improve a synthetic polymer's blood compatibility. Patency and compatibility, however, may be dependent on the attachment and retention (e.g., proliferation and migration) of endothelial cells on the graft or polymer surface. This dependency may be problematic since endothelial cells are known to detach upon exposure to physiological shear stresses. One way to adhere and retain endothelial cells on a synthetic polymer is to modify the polymer's surface. A number of surface modification strategies exist, such as attaching ionic groups, heparin, thrombomodulin, and growth factors to the graft or synthetic polymer. Another approach is to attach cell surface receptors and adhesion proteins ("adhesive peptides"), which are capable of mediating cell adhesion, to the surface of a synthetic material. For example, modifications of materials with adhesive peptides that promote integrin-mediated cell attachment, such as the RGD (arginine-glycine-aspartic acid) peptide, promote cell adhesion and spreading. RGD is known to interact with platelet integrin glycoprotein IIB/IIIA, so while RGD may enhance endothelial cell adhesion, it ultimately may decrease graft performance. The laminin-derived peptide YIGSR (tyrosine-isoleucine-glycine-serine-arginine), which binds nonintegrin receptors on endothelial cells, also may promote endothelialization when attached to synthetic polymers.

In general, the degradability of a synthetic material used with a medical implant should be considered. In some applications, degradable materials (e.g., poly(lactic acid)) are advantageous because they can be used for both tissue engineering and delivery of therapeutic agents to the implantation site. For example, cells may attach and grow on a degradable material, proliferate, and eventually adsorb and replace the material. These degradable materials are often degraded in vivo by hydrolysis or enzymatic mechanisms. To decrease thrombosis, degradable materials modified with adhesive peptides have been tested. For example, RGD has been attached to degradable block copolymers of biotinylated polyethylene glycol (PEG) with poly(lactic acid) (PLA) and poly(lactic acid-co-lysine).

The physiological response to a medical implant often includes platelet adhesion, platelet aggregation, and smooth muscle cell proliferation. In turn, this results in neointimal lesions at the implant placement site. Nitric oxide (NO) is a natural mediator of vascular homeostasis, and known to be a vasodilator, a regulator of vascular cell proliferation and migration, and an inhibitor of thrombus formation. NO has been shown to decrease the incidence of intimal hyperplasia in several animal models, and the inhibition of platelet adhesion and aggregation by NO and several NO-releasing materials has been reported. Synthetic materials that are capable of releasing NO may therefore be suitable for use with medical implants. However, the rate at which such materials release NO may be important. For example, if the release rate is too high, a dose of NO may cause a cytotoxic response, while too little may not stimulate endothelial cell proliferation to a desired degree or inadequately inhibit platelet adhesion and cell growth.

SUMMARY

The present invention generally relates to peptide-modified polyurethane compositions and methods of using such compositions. These compositions have improved properties that make them useful for a variety of applications; in particular, the manufacture of medical devices, articles, or implants that contact living tissues or bodily fluids.

According to one embodiment, the present invention provides a peptide-modified polyurethane comprising the reaction product of an isocyanate, a chain extender, and a peptide.

According to another embodiment, the present invention provides a process for making a peptide-modified polyurethane comprising: providing an isocyanate; providing a chain extender; providing a peptide; and allowing the isocyanate, chain extender, and peptide to react thereby forming the peptide-modified polyurethane.

According to another embodiment, the present invention provides a method for treating a subject comprising: providing a peptide-modified polyurethane that comprises the reaction product of an isocyanate, a chain extender, and a peptide; and administering the peptide-modified polyurethane to the subject.

The features and advantages of the present invention will be readily apparent to those skilled in the art upon a reading of the description of the embodiments that follows.

BRIEF DESCRIPTION OF THE FIGURES

A more complete understanding of this disclosure may be acquired by referring to the following description taken in combination with the accompanying figures.

Figure 1A:
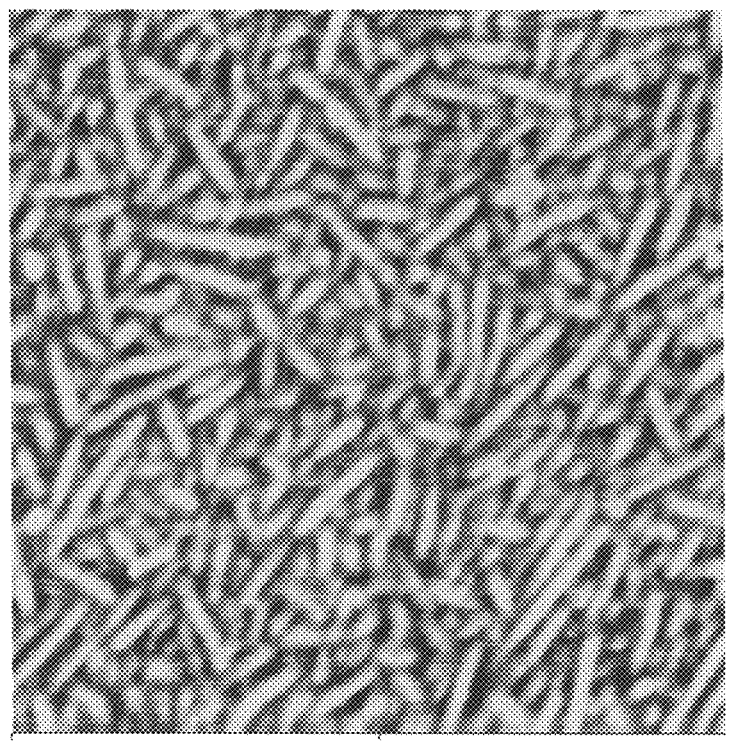
FIG. 1(a) is a photomicrograph of the surface of PUU-PPD polyurethane at $r_{sp}$=0.88 and 500×500 nm, according to one embodiment.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

DESCRIPTION

The present invention generally relates to peptide-modified polyurethane compositions and methods of using such compositions.

As used herein, the abbreviations for the genetically encoded L-enantiomeric amino acids are conventional and are as follows:

| Amino acid | Common One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |

When an amino acid sequence is represented as a series of three-letter or one-letter amino acid abbreviations, it will be understood that the left-hand direction is the amino terminal direction and the right-hand direction is the carboxy terminal direction, in accordance with standard usage and convention.

The present invention provides peptide-modified polyurethanes comprising a polyurethane polymer and a peptide that has been incorporated into the backbone chain of the polyurethane polymer. The term "polyurethane," as used herein, refers to any polymeric molecule having in its backbone chain one or more urethane linkages, urea linkages, or both (e.g., polyurethane, polyurea, polyurethaneurea). In general, the peptide-modified polyurethanes of the present invention should be biocompatible and suitable for use in medical applications. The term "biocompatible" refers to the property of being biologically compatible by not producing a significant toxic, injurious, or immunological response in living tissue. The peptide-modified polyurethanes of the present invention may be useful in medical applications, e.g., small-diameter vascular grafts. In certain embodiments, the peptide-modified polyurethanes of the present invention may have desirable mechanical properties, e.g., elasticity and tensile strength. In certain embodiments, the peptide-modified polyurethanes of the present invention may be bioactive. The term "bioactive" means having an effect on a living organism, e.g., the ability to control cellular behaviors such as proliferation, migration, and extracellular matrix production. For example, the peptide-modified polyurethanes of the present invention may be capable of releasing NO at physiological pHs, or capable of being degraded in vivo, or both. Accordingly, the present invention also provides a material comprising a peptide-modified polyurethane composition as described herein having one or more of biocompatibility, bioactivity, degradability, and improved mechanical properties.

The peptide-modified polyurethanes of the present invention generally include an isocyanate. The isocyanates that can be used in the present invention are typically polyisocyanates and diisocyanates. Suitable isocyanates also can be aromatic or aliphatic. Examples of suitable isocyanates include, but are not limited to, toluene diisocyanate (TDI); methylene diphenyl diisocyanate (MDI); methylene dicyclohexane diisocyanate (H12MDI); naphthalene diisocyanate (NDI); hexamethylene diisocyanate (HDI); p-phenylene diisocyanate (pPDI); trans-cyclohexane-1,4-diisocyanate (CHDI); 1,6-diisocyanatohexane (DICH); isophorone diisocyanate; tetramethylxylene diisocyanate (TMXDI); and an isomer thereof; and a combination thereof. It will be appreciated that this list is not exhaustive and that the invention encompasses any isocyanate known, or that may be found, to be suitable in the manufacture of polyurethanes.

The peptide-modified polyurethanes of the present invention also include a chain extender. The term "chain extender" means any compound having at least two functional groups per molecule that are capable of reacting with an isocyanate group. In general, any chain extender, or mixture of chain extenders, suitable in the art of polyurethane manufacture may be used. In certain embodiments, the chain extender comprises a polyol (e.g., a molecule with two or more reactive hydroxyl groups per molecule), such as, for example, a diol. In other embodiments, the chain extender comprises a polyamine (e.g., a molecule with two or more reactive amine groups per molecule), such as, for example, a diamine. Chain extenders with more than two functional groups may be capable of forming a branched network, a crosslinked network, or both. In certain embodiments, the chain extender may comprise a polysiloxane, for example, polydimethyl siloxane (PDMS). Examples of other suitable chain extenders include, but are not limited to, 1,4-butanediol; 1,4-butadiene; 1,6-hexanediol; 1,8-octanediol; 1,9-nonanediol; 1,10-decanediol; 1,12-dodecanediol; 1,4-cyclohexanedimethanol; 1,4-cyclohexanediol; hydroxyquinone bis(2-hydroxyethyl) ether; 2-ethyl-1,3-hexanediol; 2-butyl-2-ethyl-1,3-propanediol; 2,2,4-trimethyl-1,3-pentanediol; polytetramethylene oxide (PTMO); poly(tetramethylene ether) glycol; polyethylene adipate; ethylene diamine; 1,4-diaminocyclo hexane; ethylene diamine; 1,4-diaminocyclo hexane; and an isomer thereof; and a combination thereof.

The peptide-modified polyurethanes of the present invention also include a peptide. Thus, certain embodiments of the present invention provide peptide-modified polyurethane compositions that include an isocyanate, a chain extender, and a peptide. The term "peptide" means a compound having at least two amino acids per molecule. The term "amino acid" refers to any of the natural amino acids, synthetic amino acids, or other compounds with amino-acid-like properties.

In certain embodiments, the peptides used in peptide-modified polyurethanes of the present invention may include a bioactive peptide. The term "bioactive peptide" refers to peptides capable of performing a desired biological function. Examples of bioactive peptides include, but are not limited to, cell modulating peptides (e.g., an antibody fragment, an integrin-binding peptide, a fibronectin-derived peptide, and a laminin-derived peptide), chemotactic peptides, anticoagulant peptides, antithrombotic peptides, antitumor peptides, anti-infectious peptides, growth potentiating peptides, anti-inflammatory peptides, or combinations thereof. Bioactive peptides also include peptide fragments of proteins that are bioactive and that have the functional properties of those proteins. Other examples of suitable bioactive peptides include, but are not limited to, RGDC (SEQ ID. NO:1), RGEC (SEQ ID. NO:2), RGDT (SEQ ID. NO:3), RGDS (SEQ ID. NO:4), LDV (SEQ ID. NO:5), REDV (SEQ ID. NO:6), RGDV (SEQ ID. NO:7), LRGDN (SEQ ID. NO:8), IKVAV (SEQ ID. NO:9), YIGSR (SEQ ID. NO:10), PDSGR (SEQ ID. NO:11), RNIAEIIKDA (SEQ ID. NO:12), RGDT (SEQ ID. NO:13), DGEA (SEQ ID. NO:14), DGEAGC (SEQ ID. NO:15), EPRGDNYR (SEQ ID. NO:16), EILDV (SEQ ID. NO:17), REDV (SEQ ID. NO:18), SIKVAV (SEQ ID. NO:19), RGD (SEQ ID. NO:20), KQAGDV (SEQ ID. NO:21), HRSNRKGV (SEQ ID. NO:22), VTXG (SEQ ID. NO:23), and combinations thereof. In the context of the present invention, when a peptide is provided as a sequence of amino acids it means that the peptide may be any peptide in which at least a portion of the peptide comprises the sequence provided.

In certain embodiments, the bioactive peptide also may be a proteolytically degradable peptide. Such a proteolytically degradable peptide may be used to form a material capable of being degraded in vivo. Suitable proteolytically degradable peptides may be chosen, among other things, based on their ability to degrade upon exposure to proteolytic enzymes involved with tissue formation processes such as cell migration and tissue remodeling (e.g., matrix metalloproteases, collagenases, and plasmins). Examples of suitable proteolytically degradable peptides include, but are not limited to, collagenase-sensitive peptides (e.g., LGPA, SEQ ID. NO:24) and elastase-sensitive peptides (e.g., AAAAAAAAA, SEQ ID. NO:25). In certain exemplary embodiments, the proteolytically degradable peptide may be provided with other peptides, e.g., cell-adhesive peptides like YIGSR. In addition, the degradation rate may be tailored, e.g., based on adjusting the type and ratio of peptides present and adjusting the overall molecular weight of a given peptide-modified polyurethane molecule.

In certain embodiments, the bioactive peptide may be capable of reversibly binding NO, or may be capable of being modified to reversibly release NO. Such a bioactive peptide may comprise a NO-nucleophile complex, a NO-donor group, or both. In general, NO-nucleophile complexes (e.g., diazeniumdiolate ions) and NO-donating groups (e.g., S-nitrosothiols) may spontaneously decompose and release NO under physiological conditions. Thus, these bioactive peptides may provide a means for delivering NO. In certain exemplary embodiments, the bioactive peptide may include one or more lysines capable of forming a diazeniumdiolate ion (e.g., KKKK, SEQ ID. NO:26, and [K[N(O)NO]-]$_4$, SEQ ID. NO:27). In other exemplary embodiments, the bioactive peptide may include one or more cysteines capable of forming S-nitrosothiols (e.g., CCC, SEQ ID. NO:28).

A variety of suitable bioactive peptides are known in the art. Other useful bioactive peptides may be identified thorough the use of synthetic peptide combinatorial libraries such as those described in Houghton et al., Biotechniques, 13(3): 414-421 (1992), or using phage display procedures such as those described in Hart, et al., J. Biol. Chem. 269:12468 (1994). To determine the biological effect of certain peptide-modified polyurethanes of the present invention, samples may be tested using in vitro assays (e.g., assays designed to measure cell proliferation or cell adhesion or both). Using such assays, peptide-modified polyurethanes having the desired biological activity can be identified. In certain embodiments, in which the peptide-modified polyurethanes of the present invention are used with medical implants, suitable bioactive peptides may be chosen based on, for example, the ability to promote the adhesion of endothelial cells, the ability to promote the retention of endothelial cells under shear stresses, the ability to promote the proliferation and migration of endothelial cells, the ability to decrease platelet adhesion, the ability to reversibly bind nitric oxide, the ability to impart certain mechanical properties, and a combination thereof.

In general, the bioactive peptides may be tailored to facilitate incorporation into the peptide-modified polyurethanes of the present invention. For example, a bioactive peptide may comprise one or more amino acid spacer groups (e.g., glycine) at either or both the N- and C-terminal ends. Spacer groups may, among other things, provide a means to expose at least part of the peptide sequence on the surface of the peptide-modified polyurethanes of the present invention. The peptides also may comprise a C-terminal amine group, for example, to facilitate incorporation of the peptide into peptide-modified polyurethanes. Such an amine group may be provided by, among other things, a lysine. Examples of a suitable bioactive peptides with glycine spacers and C-terminal lysines include, but are not limited to, GGGYIG-SRGGGK (SEQ ID. NO:29), GGGCCCGGGK (SEQ ID.

NO:30), SGGKKKKGGS (SEQ ID. NO:31), and SGG[K[N(O)NO]-]$_4$GGS (SEQ ID. NO:32).

In some embodiments, other bioactive molecules may be incorporated into the peptide-modified polyurethanes of the present invention. For example, growth factors (e.g., epidermal growth factor, transforming growth factor β, and vascular endothelial cell growth factor) may be included, for example, to regulate cell behaviors such as proliferation, migration, and differentiation.

In certain embodiments, the peptide-modified polyurethanes of the present invention also may include a PEG molecule. PEG may provide a means to adjust the flexibility of the peptide-modified polyurethanes of the present invention. In addition, PEG's hydrophilic nature may limit platelet adhesion depending on, for example, its ratio of hard and soft segments, its molecular weight, and the type of PEG chosen. In general, the amount, molecular weight, and ratio of a given PEG may be varied to achieve certain desired properties. In some embodiments, the peptide-modified polyurethanes of the present invention may comprise about 4,600 g/mole of PEG. In other embodiments, PEG may be incorporated into the peptide-modified polyurethanes at about a 15% molar ratio. A person having ordinary skill in the art will recognize that an upper level exist in which the incorporation of PEG can result in undesirable mechanical properties, or in which the peptide is no longer exposed to the surface, thereby preventing cell attachment.

The choice and combination of peptides, bioactive peptides, bioactive molecules, and PEG in the peptide-modified polyurethanes of the present invention may be tailored to achieve a desired effect. For example, combinations of bioactive peptides (e.g., cell-adhesive peptides, proteolytic peptides, or NO-binding peptides) and PEG may result in a peptide-modified polyurethane that is degradable and benefits from synergistic effects leading to faster levels of endothelialization while minimizing intimal hyperplasia. Other combinations may result in a peptide-modified polyurethane that is capable of enhancing attachment, proliferation, migration, and extracellular matrix production of endothelial cells without increasing platelet adhesion.

In certain embodiments, the mechanical properties of the peptide-modified polyurethanes of the present invention may be tailored to achieve a desired result. In general, the choice or combination of peptides, PEG, or both may influence certain mechanical properties (e.g., elasticity and tensile strength). For example, incorporation of a YIGSR peptide may increase elongation while permitting tensile strength to remain unaltered. Such mechanical properties may be helpful, among other things, to transmit mechanical stimuli to seeded endothelial cells and also improve compliance matching (e.g., to reduce intimal hyperplasia at anastomotic sites). As another example, incorporation of a YIGSR peptide and PEG may increase both elongation and tensile strength.

Certain embodiments of the peptide-modified polyurethanes of the present invention may be further described as comprising a reaction product of an isocyanate, a chain extender, and a peptide. In certain embodiments, the reaction product may further comprise a PEG. As referred to herein, the term "reaction product" will be understood to mean any product that is produced during the course of the reaction between an isocyanate, a chain extender, and a peptide (and, optionally, other additives that contemporaneously may be present (e.g., mixed in) when the isocyanate, the chain extender, and the peptide are reacted), and includes the composition ultimately produced when the reaction is allowed to proceed fully to completion, as well as an intermediate product. For example, if the reaction between an isocyanate, a chain-extender, and a peptide is allowed to proceed fully to completion, the reaction product may include a composition such as, for example, a PUU-YIGSR, a PUU-PEG-YIGSR, a PUU-YIGSR-LGPA, a PU-BD-NO, a PU-BD-PEG-YIGSR, or a PU-BD-PEG-YIGSR-NO. As referred to herein, the term "intermediate product" will be understood to mean any product that is produced during the course of the reaction between an isocyanate, a chain extender, and a peptide (and, optionally, other additives that contemporaneously may be present (e.g., mixed in) when the isocyanate, the chain extender, and the peptide are reacted). For example, if the reaction between an isocyanate, a chain-extender, and a peptide is halted before the reaction is complete, the resulting composition is an "intermediate product" of the reaction between an isocyanate, a chain extender, and a peptide. As another example, a prepolymer (e.g., PUU-PPD, PU-BD, or a PUU-PPD-PEG) is an intermediate product of the reaction between an isocyanate, a chain extender, and a peptide.

After administration into a recipient subject like a human or an animal, the peptide-modified polyurethanes of the present invention may be metabolically altered through in vivo processes such as endothelialization, degradation, NO release, or a combination thereof. Thus, the peptide-modified polyurethanes of the present invention may comprise a metabolically produced form of a reaction product of an isocyanate, a chain extender, and a peptide.

In certain embodiments, the peptide-modified polyurethanes of the present invention comprise a reaction product of MDI, PTMO, PPD, and GGGYIGSRGGK. Such compounds are referred to as "PUU-YIGSR."

In certain embodiments, the peptide-modified polyurethanes of the present invention comprise a reaction product of MDI, PTMO, PPD, PEG, and GGGYIGSRGGK. Such compounds are referred to as "PUU-PEG-YIGSR."

In certain embodiments, the peptide-modified polyurethanes of the present invention comprise a reaction product of MDI, PTMO, PPD, GGGYIGSRGGK, and GGGLGPAGGK (SEQ ID. NO:33). Such compounds are referred to as "PUU-YIGSR-LGPA."

In certain embodiments, the peptide-modified polyurethanes of the present invention comprise a reaction product of MDI, PTMO, BD, and SGG[K[N(O)NO]—]$_4$GGS. Such compounds are referred to as "PU-BD-NO."

In certain embodiments, the peptide-modified polyurethanes of the present invention comprise a reaction product of MDI, PTMO, BD, PEG, and GGGYIGSRGGK. Such compounds are referred to as "PU-BD-PEG-YIGSR."

In certain embodiments, the peptide-modified polyurethanes of the present invention comprise a reaction product of MDI, PTMO, BD, PEG, GGGYIGSRGGK, and SGG[K[N(O)NO]—]$_4$GGS. Such compounds are referred to as "PU-BD-PEG-YIGSR-NO."

In certain embodiments, the peptide-modified polyurethanes of the present invention may be prepared by first preparing a prepolymer. In certain exemplary embodiments, the prepolymer may comprise a reaction product of MDI, PTMO, and PPD. Such prepolymers are referred to as "PUU-PPD." In other exemplary embodiments, the prepolymer may comprise a reaction product of MDI, PTMO, and BD. Such prepolymers are referred to as "PU-BD." In other exemplary embodiments, the prepolymer may comprise a reaction product of MDI, PTMO, PPD, and PEG. Such compounds are referred to as "PUU-PPD-PEG."

The peptide-modified polyurethanes of the present invention may be prepared by any suitable technique familiar to those skilled in the manufacture of polyurethanes. These methods include, but are not limited to: manual or mechanical mixing, with or without any solvents present; casting; reaction extrusion; and reaction injection molding. The amounts of the chain extenders, isocyanates, and peptides may be chosen based on the particular peptide-modified polyurethane desired. In general, a particular molar ratio of chain extender functional groups to isocyanate group will affect the molecular weight of the resultant peptide-modified polyurethane being synthesized. If desired, conventional polyurethane additives can be incorporated into the peptide-modified polyurethanes during preparation (e.g., catalysts, antioxidants, stabilizers, lubricants, dyes, pigments, inorganic fillers, organic fillers, and reinforcing materials).

Peptide-modified polyurethanes of the present invention are easily adaptable to a variety of fabrication techniques including, but not limited to, solvent casting, blow molding, machining, and other conventional processing techniques such as injection molding and extrusion. The peptide-modified polyurethanes also may be processed by conventional methods such as extrusion, injection, and compression. The peptide-modified polyurethanes of the present invention are particularly useful for preparing biomaterials, especially for devices and implants requiring one or more of the aforementioned properties.

In certain embodiments, peptide-modified polyurethanes of the present invention may be fabricated to comprise a plurality of micropores. The micropores may have an open and interconnected structure, among other things, to induce cell migration through the micropores. In general, the size and number of micropores may be controlled depending on the desired result. For example, the size and number of micropores may affect, for example, the ability of cells to grow into and migrate through the micropores. The size and number of micropores also may affect the mechanical properties of a peptide-modified polyurethane, such as strength and compliance. In some embodiments, the micropores have a size sufficient to allow cell growth into and through the micropores, or a size sufficient to prevent excessive blood leakage through the micropores, or both. Such embodiments may be suitable for use in medical applications such as vascular graft applications, among others. In other embodiments, peptide-modified polyurethanes comprising micropores may be used to promote transmural and anastomotic tissue in growth from surrounding tissues, or to promote the formation of a continuous monolayer of cells, or both.

Peptide-modified polyurethanes of the present invention that comprise micropores may be fabricated using any method. Examples of suitable methods include, but are not limited to, solvent casting/salt leaching, gas foaming, gas foaming/salt leaching, super critical point $CO_2$, excimer laser ablation, phase separation, and freeze-drying/salt leaching. The method chosen may depend on, among other things, a desired result, or a particular application, or both. In certain embodiments, peptide-modified polyurethanes comprising micropores may be fabricated using a gas foaming and salt leaching method. This method may be advantageous when forming peptide-modified polyurethanes for use in vascular grafts because, among other things, pore size and number can be controlled simultaneously.

In certain embodiments, the present invention provides peptide-modified polyurethanes having favorable mechanical properties and compatibility in biological environments, particularly when implanted in vivo for extended periods of time. Accordingly, the peptide-modified polyurethanes of the present invention may be used as a biomaterial. The term "biomaterial" is used in its broadest sense, referring to a material that is used in situations in which it comes in contact with the cells or bodily fluids or both of living animals or humans. Thus, the peptide-modified polyurethanes of the present invention may be useful in manufacturing medical devices, articles, or implants.

In certain embodiments, the present invention provides a medical device, article, or implant composed wholly or partly of the peptide-modified polyurethanes of the present invention. Such devices, articles, or implants may be capable of endothelialization at an anastomotic site. Examples of medical devices, articles, or implants include, but are not limited to, cardiac pace makers, cardiac assist devices, heart valves, extra-corporeal devices, blood pumps, balloon pumps, A-V shunts, biosensors, artificial joints, orthopedic implants, blood-contacting devices, sutures, vascular implants, stents, vascular grafts, heart valves, drug pumps, drug-delivery catheters, infusion catheters, thromboresistant scaffold for endothelialization, and drug-delivery guidewires.

It is understood that the peptide-modified polyurethanes of the present invention also may have applications in nonmedical areas. Such applications may include, for example, their use in the manufacture of structural components for pumps, vehicles, mining screens, and laminating compounds.

In certain embodiments, the present invention provides an article composed wholly or partly of the peptide-modified polyurethanes of the present invention.

The present invention also provides methods of using the peptide-modified polyurethanes of the present invention. Suitable uses include, among other things, those disclosed above. For example, the peptide-modified polyurethanes may be used as a method to treat a cardiovascular disease or disorder, e.g., a vascular graft.

In certain embodiments, the present invention provides a method of controlling the mechanical properties of a polyurethane polymer by incorporating a peptide into the polyurethane polymer. Such methods offer a simpler alternative to surface modification of polyurethanes because, among other things, the peptide can be used as a chain extender during polymer synthesis. Additionally, this sort of bulk incorporation allows one to develop microporous materials that are, for example, uniformly cell adhesive. For example, the amino acid sequence incorporation methods of the present invention may produce a polyurethane polymer that is more elastic without decreasing its tensile properties. This improved elasticity may be helpful to transmit mechanical stimuli to seeded endothelial cells and also to improve compliance matching, potentially reducing intimal hyperplasia at anastomotic sites.

Furthermore, the peptide-modified polyurethanes of the present invention may be designed to include multiple peptides with different biological functions to optimize, among other things, biological performance of the peptide-modified polyurethane, as well as the biological performance of the device, article, or implant comprising the peptide-modified polyurethane. For example, a mixture of several peptides (including, for example, one or more of cell adhesive peptides, chemotactic peptides, and NO-generating peptides) may be included, among other things, during the chain-extender reaction. The inclusion of a mixture of peptides may, among other things, promote endothelial cell attachment, growth, and migration while minimizing platelet adhesion and thrombosis. In certain embodiments, PEG may be included in the soft-segment domain of such materials.

To facilitate a better understanding of the present invention, the following examples of specific embodiments are given. In no way should the following examples be read to limit, or to define, the entire scope of the invention.

EXAMPLES

Materials and Methods

Synthesis of Peptide-Modified Polyurethanes Comprising YIGSR Peptides.

A PUU-PPD prepolymer was synthesized by reacting methylene di(p-phenyl isocyanate) (MDI; Aldrich Chemical Co., Milwaukee, Wis.) with poly(tetramethylene oxide) (PTMO; Aldrich Chemical Co., Milwaukee, Wis.), and then extended with p-phenylene diamine (PPD; ACROS, New Jersy). A 10% (w/v) solution of MDI (8 mmol, MW: 250) in 20 mL anhydrous N,N-dimethylformamide (DMF; Aldrich Chemical Co., Milwaukee, Wis.) was prepared in a 100 mL three-neck round flask and stirred at room temperature. A 10% (w/v) solution of PTMO (4 mmol, MW: 1,000) in 40 mL anhydrous DMF was added, and the mixture was heated to 75° C. and held there for 2 hours under argon gas. The reactor was cooled to room temperature before PPD (4 mmol, MW: 108) in 4 mL anhydrous DMF was added as a chain extender. The polymer solution was then incubated at 45° C. for 2 hours under argon gas, resulting in the formation of the PUU-PPD prepolymer. The resultant polymer solution containing the PUU-PPD prepolymer was then cooled to room temperature, precipitated in methanol, and dried under vacuum.

One example of a peptide-modified polyurethane comprising a YIGSR peptide (PUU-YIGSR) was synthesized as follows. The prepolymer prepared above was synthesized by reacting MDI with PTMO as described above and extended with a combination of GGGYIGSRGGGK peptide (Sigma-Genosys, Woodlands, Tex.) and PPD. A 10% (w/v) solution of MDI (2.4 mmol) in 6 mL anhydrous DMF was prepared in a 100 mL three-neck round flask and stirred at room temperature. A 10% (w/v) solution of PTMO (1.2 mmol) in 12 mL anhydrous DMF was added, and the mixture was heated to 75° C. and held there for 2 hours under argon gas. The reactor was cooled to room temperature before GGGYIGSRGGGK peptide (0.11 mmol) in 10 mL anhydrous DMF and PPD (1.1 mmol) in 10 mL anhydrous DMF were added as chain extenders. The polymer mixture was incubated at 45° C. for 2 hours under argon gas. The polymer solution was cooled to room temperature, precipitated in methanol, and dried under vacuum.

Synthesis of Peptide-Modified Polyurethanes Comprising PEG.

One example of peptide-modified polyurethane comprising PEG (PUU-PPD-PEG) was synthesized as follows. First, a PUU-PPD prepolymer was synthesized as described above. Then, PTMO and polyethylene glycol (PEG, MW: 4,600 g/mol; Aldrich Chemical Co., Milwaukee, Wis.) were dried for 48 hours under vacuum and used as the soft segments (molar ratio of PTMO to PEG=85/15). Polymer synthesis proceeded as described above, but used a mixture of 85% PTMO/15% PEG to form the soft segments.

One example of peptide-modified polyurethane comprising PEG and a YIGSIR peptide (PUU-PEG-YIGSIR) was synthesized as follows. A prepolymer was synthesized by reacting MDI with PTMO/PEG mixture (85/15 molar ratio) as described above and extended with a combination of GGGYIGSRGGGK peptide (Sigma-Genosys, Woodlands, Tex.) and PPD to form PUU-PEG-YIGSIR.

Synthesis of Peptide-Modified Polyurethanes Comprising Nitric Oxide Binding Peptides.

Figure 18:
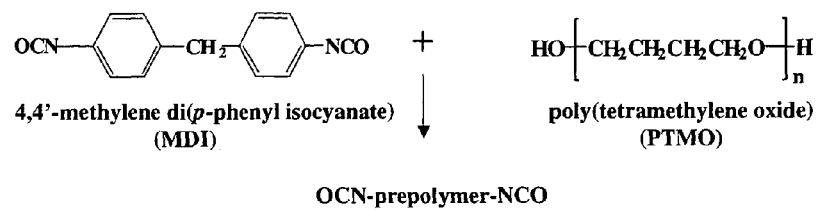
FIG. 18 is a reaction scheme for PU-BD, according to one embodiment.
Figure 18:
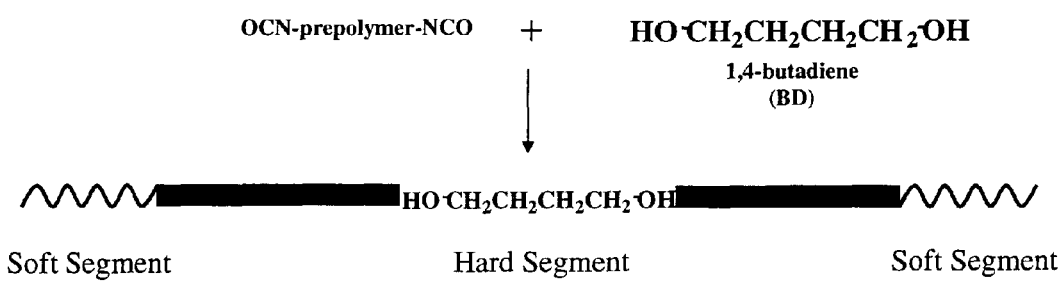

A polyurethane prepolymer (PU-BD) was synthesized by reacting MDI (Aldrich Chemical Co., Milwaukee, Wis.) with PTMO (Aldrich Chemical Co., Milwaukee, Wis.), and then extended with 1,4-butadiene (BD; Aldrich Chemical Co., Milwaukee, Wis.) as shown in FIG. 18. A 10% (w/v) solution of MDI (4 mmol, MW: 250) in 10 mL DMF (Aldrich Chemical Co., Milwaukee, Wis.) was prepared in a 100 mL three-neck round flask and stirred at room temperature. A 10% (w/v) solution of PTMO (2 mmol, MW: 2000) in 20 mL anhydrous DMF was added, and the mixture was heated to 75° C. and held there for 3 hours under argon gas. The reactor was cooled to room temperature before BD (2 mmol, MW: 90) in 2 mL anhydrous DMF was added as a chain extender. The polymer solution was then incubated at 45° C. for 3 hours under argon gas. The polymer solution was cooled to room temperature, precipitated in methanol, and dried under vacuum.

A lysine-containing peptide, SGGKKKKGGS, was synthesized using standard fluorenylmethoxycarbonyl (Fmoc) chemistry on an Applied Biosystems 431A peptide synthesizer (Foster, Calif.). The lysine residues have pendant amine groups that can be converted to diazeniumdiolates, while serine residues contain pendant hydroxyl groups to allow incorporation of the peptide into the polymer chain. The peptide was dissolved in DI water and reacted with NO gas at room temperature under argon gas in a 100 mL round bottom flask overnight. The extent of conversion of amine groups of lysine to diazeniumdiolates was measured using the Ninhydrin assay, which quantifies amines in solution. The diazeniumdiolate peptide, SGG[K[N(O)NO]-]$_4$GGS, was freeze-dried and stored at −80° C.

Figure 19:
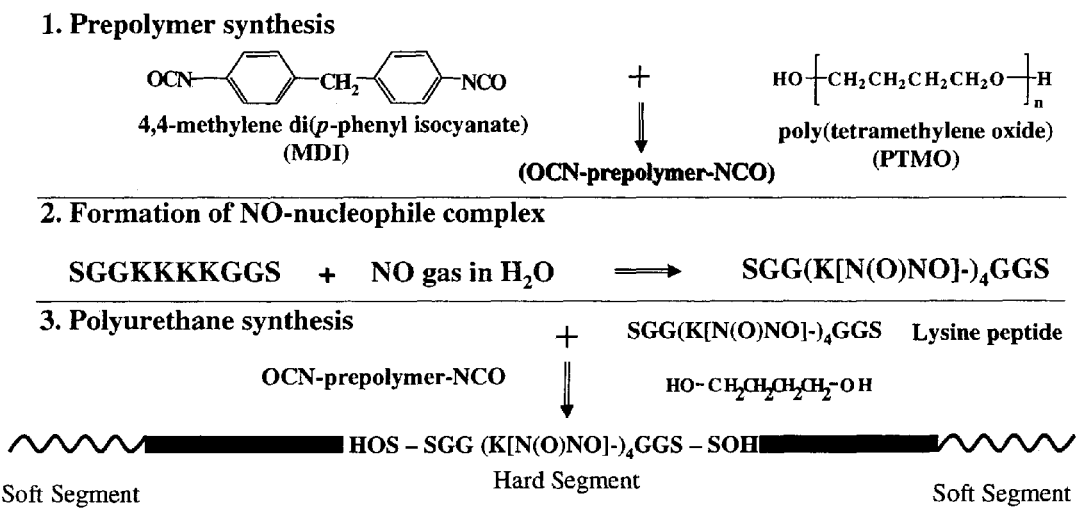
FIG. 19 is a reaction scheme for PU-BD-NO, according to one embodiment.

One example of peptide-modified polyurethane comprising nitric oxide (PU-BD-NO) was synthesized as follows. The polyurethane prepolymer was synthesized by reacting MDI with PTMO as described above and extended with a combination of SGG[K[N(O)NO]—]$_4$GGS peptide (0.22 mmol) and BD (0.54 mmol) in 5 mL anhydrous DMF as shown in FIG. 19. The polymer mixture was incubated at 45° C. for 3 hours under argon gas, then cooled to room temperature, precipitated in ethyl acetate, and dried under vacuum.

One example of peptide-modified polyurethane comprising PEG, YIGSR, and nitric oxide (PU-BD-PEG-YIGSR-NO) was synthesized as follows. A peptide having the YIGSR sequence was synthesized as described above. A polyurethane prepolymer was synthesized by reacting methylene di(p-phenyl isocyanate) (MDI; Aldrich chemical Co., Milwaukee, Wis.) with a mixture of poly(tetramethylene oxide) (PTMO; Aldrich chemical Co., Milwaukee, Wis.) and poly (ethylene glycol) (PEG; Aldrich chemical Co., Milwaukee, Wis.) before chain extension using the SGGYIGSRGGS peptide and 1,4-butanediol (BD; Aldrich chemical Co., Milwaukee, Wis.). MDI was recrystallized in hexane and a 10% (w/v) solution of MDI (4 mmol, MW: 250) in 10 mL anhydrous N,N-dimethylformamide (DMF; Aldrich Chemical Co., Milwaukee, Wis.) was prepared in a 100 mL three-neck round flask and stirred at room temperature. PTMO (1.7 mmol, MW: 2,000) and PEG (0.3 mmol, MW: 4,600) were dried for 48 hours under vacuum and mixed at an 85:15 (PTMO:PEG) molar ratio in 20 mL anhydrous DMF. This was added to the MDI solution and the mixture heated to 75° C. and held there for 3 hours under argon. The reactor was cooled to room temperature before the peptide SGGYIGSRGGS (0.1 mmol) and BD (0.65 mmol, MW: 90) in anhydrous DMF were added as chain extenders. The polymer solution was then stirred at 45° C. for 3 hours under argon. The polymer solution was cooled to room temperature, precipitated in ethyl acetate, and dried under vacuum. The resultant polymer was one example of a PU-BD-PEG-YIGSR peptide-modified polyurethane (see FIG. 34).

Next, the lysine-containing peptide, SGGKKKKGGS, was synthesized and reacted with NO to form SGG[K[N(O)

Figure 34:
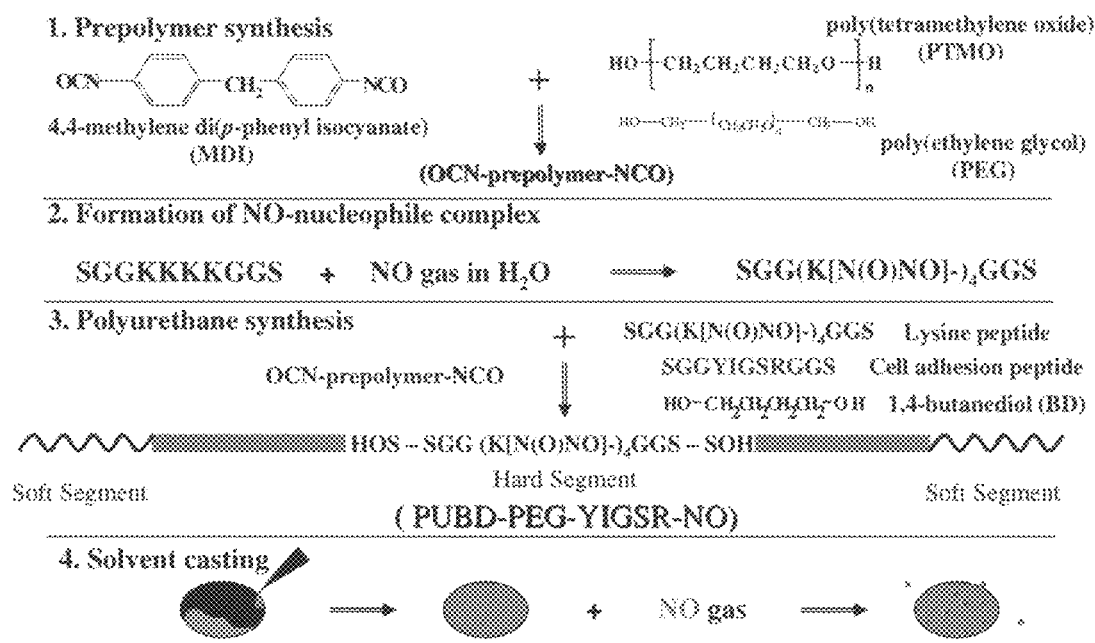
FIG. 34 is a reaction scheme for PU-BD-PEG-YIGSR-NO, according to one embodiment.

NO]⁻]₄GGS, as described above. The polyurethane prepolymer was synthesized by reacting MDI with a PTMO/PEG mixture as described above and extended with a combination of SGG[K[N(O)NO]⁻]₄GGS peptide (0.2 mmol), SGGYIGSRGGS peptide (0.1 mmol), and BD (0.45 mmol) in anhydrous DMF. The polymer mixture was stirred at 45° C. for 3 hours under argon, then cooled to room temperature, precipitated in ethyl acetate, and dried under vacuum. The resultant polymer was one example of a PU-BD-PEG-YIGSR-NO peptide-modified polyurethane (FIG. 34).

Synthesis of Peptide-Modified Polyurethanes Comprising Proteolytic Peptides.

One example of peptide-modified polyurethane comprising a proteolytic peptide was synthesized as follows. PUU-YIGSR-LGPA was prepared as follows. PUU-PPD prepolymer was synthesized as described above and extended with a combination of GGGYIGSRGGGK, GGGLGPAGGGK (Sigma-Genosys, Woodlands, Tex.), and PPD. A prepolymer was synthesized using a 10% (w/v) solution of MDI (2.4 mmol), and PTMO (1.2 mmol) at 75° C. for 3 hours under argon gas as above. Next, chain extension was performed using GGGYIGSRGGGK (0.11 mmol), GGGLGPAGGGK (0.33 mmol), and PPD (0.76 mmol) in anhydrous DMF at 45° C. for 3 hours under argon. The polymer solution was cooled to room temperature, precipitated in ethyl acetate, and dried under vacuum.

Characterization of Peptide-Modified Polyurethanes.

Polyurethanes were characterized via ¹H NMR using a 400 MHz NMR spectrometer (Advance 400, Bruker, Germany) DMF-d₇ (Aldrich Chemical Co., Milwaukee, Wis.). Molecular weight distributions were obtained by GPC with UV and evaporative light scattering detectors (Polymer Laboratories, Amherst, Mass.). Samples for GPC analysis were dissolved in HPLC-grade DMF at a concentration of 1 mg/mL and run at 70° C. through PLgel 5 µm Mixed-C columns (Polymer Laboratories, Amherst, Mass.) at a flow rate of 1 mL/min. Calibration was performed using polystyrene standards (PS; Polymer Laboratories, Amherst, Mass.), ranging in molecular weight from 5,000-96,4000 Da. DSC thermograms were obtained using a Differential Scanning Calorimeter (Pyris 1, Perkin Elmer, Wellesley, Mass.). Samples were cooled below −60° C. and increased at 10° C./min to 300° C. under nitrogen gas. Glass transition temperatures and melting temperatures were analyzed using Pyris software. Fourier transform infrared (FT-IR) spectroscopy was performed using a Nicolet 500 spectrometer. Thin films were prepared by mixing samples with KBr and pressed into pellets under vacuum. Sixteen scans were taken of each sample at a resolution of 4 cm⁻¹.

Characterization of Peptide-Modified Polyurethane Films.

Polyurethane films were dissolved in tetrahydrofuran (THF; 0.3 wt %) and sterilized using 0.2 µm pore size PTFE syringe filters (Whatman, N.J.). Polyurethane films were prepared on glass coverslips (18 mm; Fisher Scientific, PA) by solvent casting at room temperature. Polyurethane films were held under vacuum for 48 hours to ensure removal of the solvent. The polyurethane films were held under vacuum for 48 hours to ensure removal of the solvent and sterilized under UV light.

The equilibrium contact angles of DI water on polyurethane films were measured using a contact angle goniometer (CAM-Micro). Six measurements were taken to calculate average contact angles on the surface of each film. ESCA analysis was performed using a Physical Electronics Model 5700 XPS instrument. Photo-emissions were produced through the use of a X-ray source (1486.6 eV) operated in the fixed retard ratio mode at a pass energy of 23.5 eV. Spectra were acquired over a 10-45 take-off angle range. Charge neutralization was accomplished via bombardment with a low energy beam.

To evaluate the distribution of YIGSR peptide on the surface of certain polyurethane films, films were reacted with the fluorescent probe 7-chloro-4-nitrobenzo-2-oxa-1,3-diazole (NBD-Cl; Molecular Probes, Eugene, Oreg.). This fluorescent compound reacts with tyrosine residues. 250 mM NBD-Cl was prepared in DMSO. Polyurethane films were placed in a well of a 12-well tissue culture plate, 2 mL potassium phosphate buffer solution (pH 8.0) was added, and then 80 µl NBD-Cl solution was added. Samples were incubated at 37° C. for 2 hours. Unreacted NBD-Cl was rinsed with buffer solution over one week. The surfaces were observed using a Nikon E600 fluorescence microscope equipped with a Sony DXC-950P CCD camera. A Nikon multiband DAPI-FITIC-Texas red (excitation wavelengths: 385-415, 485-505, 555-585 nm, emission wavelengths: 450-470, 510-540, 590-650 nm) filter was used.

To investigate the distribution of hard and soft segments in a peptide-modified polyurethane, the surfaces of certain polyurethane films were imaged by AFM (NanoScope IIIa, Digital Instruments, Santa Barbara, Calif.). A 125 µm etched silicon cantilever was used. The radius of curvature of a silicon tip was 5-10 nm, and the resonance frequency was 300 kHz. Phase and height images were obtained using tapping mode under ambient conditions from $r_{sp}$=0.92 to 0.80 ($r_{sp}$=set point amplitude/free amplitude of oscillation). The data obtained were analyzed with Nanoscope IIIa controller and software.

Uniaxial mechanical testing was performed using an Instron model 5565 at a cross head speed of 25 mm/min with a 5 kN load cell. Polymers were dissolved in DMF (Aldrich Chemical Co., Milwaukee, Wis.) at 10 wt % and sterilized using 0.2 µm pore size PTFE syringe filters (Whatman, N.J.). Polyurethane films were prepared in Teflon molds by solvent casting at 60° C. under vacuum for 48 hours. Test specimens were prepared according to ASTMD-638-VI. The tensile strength was calculated from the maximum load at break and the initial cross sectional area of the specimen. Sample thickness was measured using a digital caliper (Mitutoyo, Hauppauge, N.Y.).

NO Release Profiles of Peptide-Modified Polyurethane Films.

Sterilized polyurethane films were reacted with NO gas under argon at room temperature overnight. After rinsing the films with N-2-hydroxyethylpiperazine-N'-2-ethanesulfonic acid (HEPES) buffered saline (HBS, pH 7.4) three times to remove physically adsorbed NO gas on the surface, the films were incubated in HBS at 37° C. Release of NO from the films was measured using the Griess assay, which quantifies nitrites, the primary degradation product of NO, in solution.

Cell Maintenance.

Bovine aortic endothelial cells (BAECs; Clonetics, San Diego, Calif.) and Sprague-Dawley rat aortic smooth muscle cells (SDSMCs), passage 2-5, were used. Dulbecco's modified Eagles's medium (DMEM; Sigma Chemical Co., St. Louis, Mo.) was prepared with 10% fetal bovine serum (FBS; BioWhitaker, Walkersville, Md.), 2 mM L-glutamine, 1 U/mL penicillin, and 100 mg/L streptomycin (GPS; Sigma Chemical Co., St. Louis, Mo.). Endothelial basal medium (EBM; Sigma Chemical Co., St. Louis, Mo.) was prepared with 10% endothelial medium supplement (Sigma Chemical Co., St. Louis, Mo.), which contained FBS, basic fibroblast growth factor (bFGF), heparin, epidermal growth factor, and hydrocortisone. BAECs were maintained on a mixture of EBM and DMEM (25/75 or 50/50 volume ratio) at 37° C. in a 5% $CO_2$ environment.

Viability of Cells on Peptide-Modified Polyurethane Films.

To evaluate viability of endothelial cells on films, eight-well FlexiPerms (Sigma Chemical Co., St. Louis, Mo.) were attached to polyurethane films to create culture wells on each surface. BAEC suspensions were prepared and seeded at a concentration of 17,000 cells/$cm^2$ on the films. Calcein AM and ethidium homodimer-1 (Live-Dead Assay Kit; Molecular Probes, Inc., Eugene, Oreg.) were used to determine endothelial cell viability after 24 or 72 hours in culture. Calcein AM is converted to a green fluorescent product within live cells due to enzymatic activity, while ethidium homodimer-1, a red fluorescent compound, accumulates in dead cells due to increased membrane permeability.

To evaluate cytotoxicity of any leachable products, polyurethane films were placed in glass vials and dried under vacuum for 48 hours. Each film had a 6 $cm^2$ surface area. According to USP extraction ratio of synthetic Polyurethane films with thickness less than 0.5 mm, 1 mL of HBS (HEPES-buffered saline) buffer (10 mM, pH 7.4) solution was added to each vial. Samples were incubated at 37° C. After 30 and 60 days of extraction, endothelial cells were seeded into a 24-well tissue culture plate at 15,000 cells/$cm^2$. About 24 hours after cell seeding, the extract solutions were sterilized using a 0.2 μm pore size syringe filter and added to the culture medium at 10, 15, or 25% (v/v). After 24 hours of incubation with the extracts, cell viability was evaluated by Calcein AM/ethidium homodimer staining as described above.

Adhesion and Spreading of Cells on Peptide-Modified Polyurethane Films.

To evaluate adhesion of endothelial cells, BAECs were seeded at a concentration of 17,000 cells/$cm^2$ in eight-well FlexiPerm chambers (Sigma Chemical Co., St. Louis, Mo.) attached to polyurethane films, or in six-well polystyrene plates (Corning Inc., Corning, N.Y.) using hollow stainless steel molds. Cells were cultured at 37° C. in a 5% $CO_2$ environment. To evaluate cell spreading and adhesion, after 4, 6, 24 or 48 hours of incubation, nonadherent cells were removed by rinsing, and fresh medium was added. Cells were observed by phase contrast microscopy (Zeiss Axiovert 135, Thornwood, N.Y.), and digital image processing (Scion Image) was used to determine cell areas. To evaluate cell attachment, the medium was removed by rinsing with PBS, and adherent cells were detached with trypsin and counted using a Coulter Counter (Multisizer 3, Beckman Coulter).

Competitive inhibition of attachment and spreading of endothelial cells was also examined using soluble YIGSR peptides to ensure that improved BAEC adhesion and spreading was due to biospecific interactions with the YIGSR peptides that were incorporated into the polymer structure. Cells were seeded at a concentration of 17,000 cells/$cm^2$ in eight-well FlexiPerm chambers attached to polyurethane films and incubated with soluble YIGSR peptide (Sigma Chemical Co., St. Louis, Mo.) at 0, 0.01, 0.1, and 1 mM in EBM/DMEM (25:75 or 50:50 volume ratio) at 37° C. in a 5% $CO_2$ environment. After 4 hours incubation, attachment and spreading of cells were evaluated as described above.

Proliferation of Cells on Peptide-Modified Polyurethane Films.

To evaluate cell proliferation, eight-well FlexiPerms were attached to polyurethane films. Cells were seeded at a concentration of 17,000 cells/$cm^2$. After 48 hours incubation at 37° C. in a 5% $CO_2$ environment, immunohistochemical staining for proliferating cell nuclear antigen (PCNA) was employed. The PCNA antibody stains cells in the S-phase of mitosis. Cells were washed with PBS, fixed with 10% formalin (Stephens Scientific, N.J.) for 10 min, permeabilized with methanol (Sigma Chemical Co., St. Louis, Mo.) for 2 min, and incubated in 3% $H_2O_2$ (Fisher Scientifics, PA) for 5 min. Cells were incubated with mouse anti-human PCNA IgG (DAKO, Carpinteria, Calif.) for 1 hour, rinsed with PBS, and incubated with horseradish peroxidase (HOURSP)-conjugated anti-mouse IgG (Dako, Carpinteria, Calif.) for 40 min. Antibodies were diluted 1:100 in PBS containing 3% FBS, and incubations were performed at room temperature in a humidified chamber. After rinsing with PBS, cells were treated with aminoethylcarbazole choursomagen (Dako, Carpinteria, Calif.) for 10 min. Counter-staining was performed with Mayer's hematoxylin (Dako, Carpinteria, Calif.). Using this procedure, proliferating cells appear red and nonproliferating cells appear blue. Two wells were used as controls; one well with no primary (anti-PCNA IgG) antibody, and one well with neither primary nor secondary (HOURSP-conjugated anti-mouse IgG) antibody.

For PU-BD and PU-BD-NO, polyurethane films were prepared and sterilized as described above. PU-BD-NO films were reacted with NO gas under argon at room temperature overnight and then rinsed with PBS. To evaluate BAEC and SDSMC proliferation, cells were seeded at a concentration of 17,000 cells/$cm^2$ in a six-well cluster polystyrene plate (Corning Incorporated, Corning, N.Y.). After a 24-hour incubation at 37° C. in a 5% $CO_2$ environment, PU-BD and PU-BD-NO films were placed into transwell inserts (24 mm diameter, 0.4 μm pore polycarbonate membrane, Corning Incorporated, Corning, N.Y.) in the six-well plates. After another 48 hours of culture at 37° C. in a 5% $CO_2$ environment, immunohistochemical staining for proliferating cell nuclear antigen (PCNA) was employed to assess cellular proliferation. The PCNA antibody stains cells in the S-phase of mitosis, and, using this procedure, proliferating cells appear red and nonproliferating cells appear blue. Cells were fixed in a 10% buffered formalin solution (Sigma Chemical Co., St. Louis, Mo.). A 3% hydrogen peroxide solution was used to block endogenous peroxidases, and cells were incubated with anti-mouse IgG HRP (Dako Corp., Carpinteria, Calif.) diluted 1:100 in PBS with 3% FBS. After rinsing, cells were incubated with anti-mouse IgG HRP (Dako Corp., Carpinteria, Calif.), which generates a red precipitate. Cells were counterstained with Mayer's hemotoxylin (Dako Corp., Carpinteria, Calif.). The percentage of proliferating cells per field of view (200×) was determined using phase contrast microscopy (Ziess Axiovert 135, Thornwood, N.Y.) by averaging five fields per sample.

Migration of Endothelial Cells on Peptide-Modified Polyurethane Films.

To assess migration, a fence-style assay was utilized. Polyurethane films were placed in the six-well tissue culture plates, and double-walled round Teflon molds (inner diameter: 6 mm, outer diameter: 17 mm) were placed on top of the films. BAECs were seeded at a concentration of 35,000 cells/$cm^2$ in the inner walls. After 24 hours, the original boundaries were recorded, and the inner walls were removed. Mitomycin C (Calbiochem, San Diego, Calif.) was added to the medium at 0.5 μg/mL to prevent cell proliferation. After 24 and 48 hours of incubation at 37° C. in a 5% $CO_2$ environment, the cells that had migrated over the original boundary were observed using a phase contrast microscope (Zeiss Axiovert 135).

Endothelialization at an anastomotic site was also simulated in an in vitro system. Polyurethane films were cast on glass, and then eight-well FlexiPerms were attached to the surfaces. Collagen I (Sigma Chemical Co., St. Louis, Mo.) was dissolved at 2.5 mg/mL in 3% glacial acetic acid. Surfaces coated with collagen I were prepared by adding 50 µl of the collagen I solution into each well and drying under vacuum. After washing the surfaces in PBS three times, endothelial cells were seeded onto the surfaces at 34,000 cells/cm$^2$. After 24 hours the FlexiPerms were removed, the boundaries were marked, and fresh medium was added. After 48 hours incubation at 37° C. in a 5% $CO_2$ environment, the number of cells that had migrated across the boundary simulating an anastomotic site, from the collagen I-coated surface to the polyurethane surface, were counted under a phase contrast microscope as described above.

Extracellular Matrix Production by Endothelial Cells on Peptide-Modified Polyurethane Films.

To evaluate extracellular matrix (ECM) production, eight-well FlexiPerms were attached to the polyurethane films. BAEC suspensions were prepared with 5 µg/mL ascorbic acid added to the culture medium and seeded at a concentration of 17,000 cells/cm$^2$. Four of the wells on each film were cultured with 1 µCi/mL $^3$H-glycine added to the medium to measure the ECM production via incorporation of the radioactive amino acid into newly synthesized ECM proteins. The other four wells were cultured in the absence of $^3$H-glycine and used for cell counting. After 48 hours of incubation at 37° C. in a 5% $CO_2$ environment, cells cultured in the absence of $^3$H-glycine were trypsinized and counted on a Coulter Counter. Cells in the remaining wells were rinsed with PBS and deionized (DI) water and then lysed in 25 mM ammonium hydroxide for 30 min. The remaining ECM was washed with 70% ethanol and air-dried. In order to digest glycoprotein, elastin, and collagen, the ECM was sequentially exposed to 200 µg/mL trypsin for 4 hours, 58 U/mL elastase for 4 hours, and 76 U/mL collagenase for 8 hours at 37° C. Finally, the wells were incubated in 1 N NaOH for 1 hour at room temperature to remove any remaining proteins. All enzyme solutions were prepared in TEC buffer (25 mM Tris-HCl, 5 mM calcium chloride, pH 8). ECM production was determined by the amount of radioactivity in the glycoprotein (trypsin-sensitive), elastin (elastase-sensitive), and collagen (collagenase-sensitive) fractions using scintillation counting (Minaxiβ Tri-Carb 4000, Packard Instrument Co., Meridien, Conn.). NaOH fractions were also evaluated by scintillation counting to ensure that the ECM had been completely digested.

Adhesion of Platelets on Peptide-Modified Polyurethane Films.

Polyurethane films were cast on glass coverslips (18 mm; Fisher Scientific, PA) as described above. A solution of 2.5 mg/mL collagen I (Sigma Chemical Co., St. Louis, Mo.) solution was prepared in 3% glacial acetic acid. Glass coverslips were incubated with the collagen I solution for 45 minutes in a humidified environment at room temperature to provide a highly thrombogenic reference material. Blood was obtained from a healthy volunteer, and 10 U/mL heparin (Sigma Chemical Co., St. Louis, Mo.) was added to prevent coagulation of the blood. About 10 µM mepacrine (Sigma Chemical Co., St. Louis, Mo.) was added to fluorescently label the platelets. Surfaces of collagen I (positive control) and various peptide-modified polyurethane polyurethane films were incubated with mepacrine-labeled whole blood at 37° C. for 20 minutes and then rinsed with PBS to remove all visible blood. The number of adherent platelets per field of view (200×) was determined using a fluorescent microscope (Zeiss Axiovert 135, Thornwood, N.Y.).

Fabrication of Peptide-Modified Polyurethane Microporous Scaffolds.

PUU-PEG and PUU-PEG-YIGSR were used to fabricate microporous scaffolds using gas foaming and salt leaching via incorporation of sodium bicarbonate. PUU-PEG and PUU-PEG-YIGSR were separately dissolved in anhydrous DMF (Aldrich Chemical Co., Milwaukee, Wis.) at 10% (w/v) concentration, and DMF was partially evaporated at 60° C. under vacuum. Sieved sodium bicarbonate salts (Sigma Chemical Co., St. Louis, Mo.; particle size of 100-200 µm, weight fraction=90 wt %) were added into the viscous polymer solutions at room temperature and mixed well. The paste of polymer and salts was placed in a Teflon mold (75×25×1 mm) and dried for 24 hour at room temperature. The polymer/salt films were immersed in a 50% citric acid solution (Sigma Chemical Co., St. Louis, Mo.) for 30 minute to induce gas foaming and then in DI water for 3 days to leach remaining salts. DI water was changed everyday, and samples were freeze-dried for 48 hour. Scaffolds were cut into disk shape (diameter=7 mm, thickness=1 mm, weight=10-20 mg) for further study.

Characterization of Peptide-Modified Polyurethane Microporous Scaffolds.

The porosity of the above-described scaffolds was determined using a mercury intrusion porosimeter (Autoscan-500, Quantachrome, Boynton Beach, Fla.). Scaffolds were loaded into the intrusion chamber for measurement. Mercury was intruded into samples at 500 psi, and the intruded mercury volume and pressure were recorded. Porosity was determined from the total intruded volume per unit mass.

The microstructure of the scaffold was investigated using scanning electron microscopy (SEM). Samples were sputter coated with gold for 30 sec at 100 mA by a sputter coater (Pelco Sputter Coater 91000, Ted Pella, Redding, Calif.). The surface and cross-section of scaffolds were observed using SEM (JEOL, JSM-5300, Japan; operated at 30 kV).

Uniaxial mechanical testing was performed using an Instron model 5565 at a cross head speed of 25 mm/min with a 50 N load cell. Test specimens were prepared according to ASTMD-638-VI. Sample thickness was measured using a digital caliper (Mitutoyo, Hauppauge, N.Y.).

Seeding and Culture of Endothelial Cells in Peptide-Modified Polyurethane Microporous Scaffolds.

Scaffold disks were immersed in 70% ethanol overnight prior to use. The scaffolds were then soaked three times in sterile PBS for 30 minutes each time, and in cell culture media for 15 min. For cell seeding, the scaffolds were placed in six-well tissue culture plates, and excess medium was removed. 40 µL of cell suspension at 1×10$^6$ cells/mL was added onto the top of the scaffold slowly and allowed to permeate through the matrix. The scaffold was turned over, and an additional 40 µL of cell suspension was added the opposite surface. six-well plates containing cell seeded-scaffolds were maintained at 37° C. in a 5% $CO_2$ environment for cell attachment. After 90 min, cell-seeded scaffolds were placed in 9 six-well plates, culture medium was added, and constructs were incubated at 37° C. in a 5% $CO_2$ environment. After three days, each cell-seeded scaffold was placed in a well of a 24-well plate, washed three times with the sterile PBS, and fixed with 2.5% glutaraldehyde (Sigma Chemical Co., St. Louis, Mo.) overnight at 4° C.

For evaluation by SEM, the cell-seeded scaffolds were dehydrated in a graded series of ethanol/water solutions, and dried with tetramethylsilane on the ice bath (TMS, Electron Microscopy Science, Fort Washington, Pa.). Samples were sputter coated, and morphology of cells in the scaffold was observed under SEM as described above.

For histological analysis, cell-seeded scaffolds were sectioned to 30 μm at −30° C. using a cryostat (HM505E; Microm, Walldorf, Germany). Sections were stained with Mayer's hematoxylin and observed by light microscopy (Zeiss Axiovert 135).

Migration of Cells Through Peptide-Modified Polyurethane Microporous Scaffolds.

The scaffolds were prepared as described above and placed in six-well plates, and 40 μL of cell suspension at $1\times10^6$ cells/mL was added onto only the top of the scaffold. The plates were then incubated at 37° C. in a 5% $CO_2$ environment for 90 minutes to allow cell attachment. Each scaffold was placed into a transwell cell culture insert (6.4 mm diameter, 8 μm pore PET membrane: Becton Dickinson, Franklin Lakes, N.J.) in 24-well companion plates (Becton Dickinson). Medium was added to the insert and the well, and then incubated at 37° C. in a 5% $CO_2$ environment. After 7 days of culture, each scaffold was removed from the insert well, and each insert well was placed in 24-well companion plate. The membrane of the insert well was washed with sterile PBS, and adherent cells on the top and bottom of the insert membrane were removed by trypsinization and counted using a Coulter counter (Multisizer 3, Beckman Colulter).

DNA and Hydroxyproline Measurement in Peptide-Modified Polyurethane Microporous Scaffolds.

The sterile scaffolds were prepared as described above. The scaffolds were placed in six-well plates, and 40 μL of cell suspension at $1\times10^6$ cells/mL was added onto the top and the bottom of the scaffold respectively, as described above. The cell seeded scaffolds in the six-well plates were placed at 37° C. in a 5% $CO_2$ environment for cell attachment for 90 minutes and then transferred to 9 six-well plates. Additional medium was added, and the cell-seeded scaffolds were incubated at 37° C. in a 5% $CO_2$ environment. After three days of culture, cell-seeded scaffolds were washed with the sterile PBS and cut into four pieces. Samples were digested with 0.1 N NaOH overnight at 37° C. The digested samples were neutralized with 0.1 N HCl. The digested samples and calf thymus DNA standards were diluted with TE buffer (200 mM Tris-HCl, 20 mM EDTA, pH 7.5) and combined with Hoechst 33258 (Molecular Probes, Eugene, Oreg.), a fluorescent DNA binding dye. DNA content was determined by measuring fluorescence using fluorometer (VersaFluor, BioRad Lab., Hercules, Calif.) with excitation wavelength of 360 nm and emission wavelength of 460 nm, and compared to the calf thymus DNA standards (0 to 100 ng/mL).

For hydroxyproline measurement, the neutralized samples and hydroxyproline standards were combined with 4 N NaOH in Wheaton cryovial (Wheaton Science Products, Millville, N.J.) and autoclaved for 20 minute at 247° F. to hydrolyze collagen. Samples and hydroxyproline standards (in DI water, 0-100 ng) were cooled to room temperature and neutralized with 4 N HCl. Then they were oxidized with Chloramine T (ICN Biomedicals, Aurora, Ohio) and developed with p-dimethylbenzaldehyde (ICN Biomedicals, Aurora, Ohio). The production of hydroxyproline was determined using spectrophotometer at 550 nm.

Results

Synthesis and Characterization of a PUU-PPD and a PUU-YIGSR Peptide-Modified Polyurethane.

The NMR spectra of PUU-PPD and PUU-YIGSR were obtained, and the characteristic proton peaks of tyrosine (6.5-7.0 ppm) from the GGGYIGSRGGGK sequence indicated the successful incorporation of the peptide sequence into the PUU-YIGSR polymer. To ensure that the peptides were not merely physically entangled or mixed in polymer matrix, the polymer was washed and filtered several times with methanol prior to NMR measurement. The peaks of prepolymer, PUU-PPD, and PUU-YIGSR were also assigned and characterized. Then, the number of the protons was calculated from the intensity. The intensity was compared to theoretical values. The reactivity of the peptide into the polymer was nearly 100%. ESCA and contact angle measurements also supported the conclustion that the peptide sequences were incorporated into the polymer. The peptide concentration of the polymer matrix was approximately 56 μmol per gram determined from NMR.

The number-average molecular weight (Mn), the weight-average molecular weight (Mw), and the polydispersity index (PDI) were determined by GPC using polystyrene standards. The PUU-PPD and PUU-YIGSR polymers had similar molecular weights (PUU-PPD: Mn=40,001, Mw=53,307, PDI=1.33 and PUU-YIGSR: Mn=43,054, Mw=54, 531, PDI=1.27).

The surface atomic concentration was determined using ESCA with various take-off angles (PUU-PPD: C=83.6%, N=1.1%, O=15.3% at 10° and C=86.7%, N=0.8%, O=12.5% at 45°; PUU-YIGSR: C=70.6%, N=3.4%, O=26.0% at 10° and C=77.2%, N=1.3%, O=21.4% at 45°). Nitrogen (N) and oxygen (O) concentrations are related to the urea linkages of the hard segments and amide linkages of the peptide sequences. The higher level of nitrogen and oxygen detected on the PUU-YIGSR surface indicates that the GGGYIGSRGGGK peptide sequences were successfully incorporated into the polymer backbone and present at the surface of the material.

There was no significant difference in the FT-IR spectra between PUU-PPD and PUU-YIGSR. For both PUU-PPD and PUU-YIGSR, the hydrogen-bonded urea carbonyl peak occurred at 1640 $cm^{-1}$. The urethane carbonyl peaks appeared at 1720 $cm^{-1}$ for hydrogen bond and at 1740 $cm^{-1}$ for free bond. The CH stretch peaks of the soft segment, PTMG, appeared at 2850 $cm^{-1}$ and 2940 $cm^{-1}$, and the hydrogen-bonded NH peak also appeared at 3310 $cm^{-1}$.

The thermal behaviors of PUU-PPD and PUU-YIGSR were examined using DSC. The glass transition temperature (Tg) was determined to be −30° C. for PUU-PPD and −45° C. for PUU-YIGSR. The melting point (Tm) was approximately 260° C. for both polymers. Thus, the introduction of peptides into the polymer backbone lowered the glass transition temperature of the soft segment, but did not affect the melting temperature of the hard segment.

Characterization of a PUU-YIGSR Peptide-Modified Polyurethane Film.

Polyurethane films fabricated using a solvent casting method on glass coverslips as described above were characterized. The bulk polymer characterization shows that GGGYIGSRGGGK peptide sequences were successfully incorporated into the polymer at a ratio of approximately 56 μmol per gram of polymer. Based on this, the surface peptide concentration of PUU-YIGSR is approximately 0.2 nmol/$cm^2$. This concentration was calculated using the polymer density (1.25 g/$cm^3$) and the thickness of the monolayer (20 nm). The thickness of the monolayer was obtained based on hard segment length. Water contact angle measurements showed that the contact angle on PUU-YIGSR (68.8±1.17°) was approximately about 10° lower than the contact angle on PUU-PPD (80.16±1.72°), indicating that the surface of PUU-YIGSR is more hydrophilic and polar due to the incorporated peptides.

In order to study the peptide distribution on the surface of polyurethane films, a fluorescent dye (NBD-Cl) was employed that is capable of reacting with the tyrosine residues under aqueous conditions. When reacted with NBD-Cl, PUU-PPD showed no fluorescence; however, PUU-YIGSR showed bright orange fluorescence evenly distributed over its entire surface area. This result suggests that peptides are uniformly distributed on the surface of the PUU-YIGSR polymer.

Figure 1B:
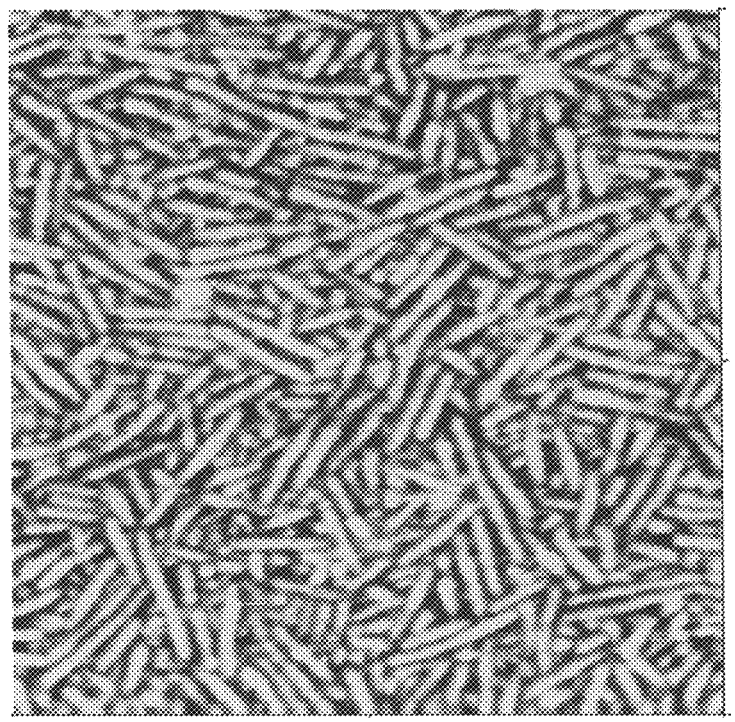
FIG. 1(b) is a photomicrograph of the surface of PUU-YIGSR at $r_{sp}$=0.88 and 500×500 nm, according to one embodiment.

The hard segment distribution on the surface was also examined using AFM. FIG. 1(a) and FIG. 1(b) shows AFM tapping mode images from the surface of polyurethane films at $r_{sp}$=0.88. The $r_{sp}$ value is the ratio of set point amplitude and free amplitude of oscillation. At $r_{sp}$=0.88, the very top layer of the surface is being detected. The hard segment domains were exposed to the surface and appeared bright. The cylindrical and spherical hard segment domains were distributed in the soft segment matrix very randomly on the PUU-PPD surface. However, on PUU-YIGSR, most hard segment domains were cylindrically shaped and arranged parallel to the plane of the surfaces. Even at low tapping force, $r_{sp}$=0.80, the patterns of hard segment distribution in PUU-PPD and PUU-YIGSR were very similar to $r_{sp}$=0.88.

The incorporation of the peptides into the polymer backbone did not significantly affect the tensile strength (7.3±0.29 MPa for PUU-PPD and 7.6±0.71 MPa for PUU-YIGSR). However, the elastic modulus decreased from 3.9±0.70 MPa for PUU-PPD to 0.9±0.07 MPa for PUU-YIGSR (p<0.005), and elongation increased from 123.2±18.6% for PUU-PPD to 512±59.6% for PUU-YIGSR (p<0.001).

BAEC Viability and Cytotoxicity of a PUU-YIGSR Peptide-Modified Polyurethane Film.

BAECs were seeded and cultured on the polyurethane films and also cultured in extract solutions from the films to evaluate cytotoxicity of any leachables. Over 95% of endothelial cells remained viable at 24 or 72 hours when cultured on PUU-PPD and PUU-YIGSR films. In addition, to evaluate cytotoxicity of any leachables under aqueous conditions, the polyurethane films were incubated in HBS buffer solution for 30 or 60 days, and BAECs were then cultured with the extract solutions. Over 90% of BAECs were viable over the three different extract concentrations for both PUU-PPD and PUU-YIGSR.

BAEC Adhesion and Spreading on a PUU-YIGSR Peptide-Modified Polyurethane Film.

Figure 2A:
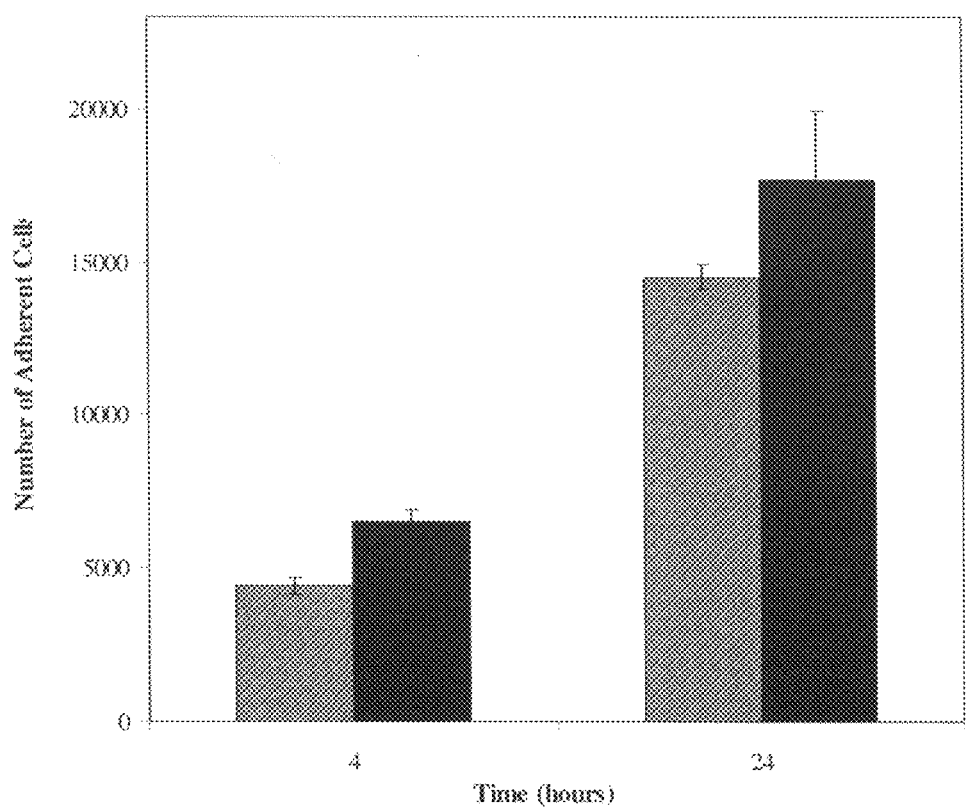
FIG. 2(a) is a graph comparing the number of adherent BAECs to PUU-PPD and PUU-YIGSR after a 4- and a 24-hour incubation, according to one embodiment.
Figure 2B:
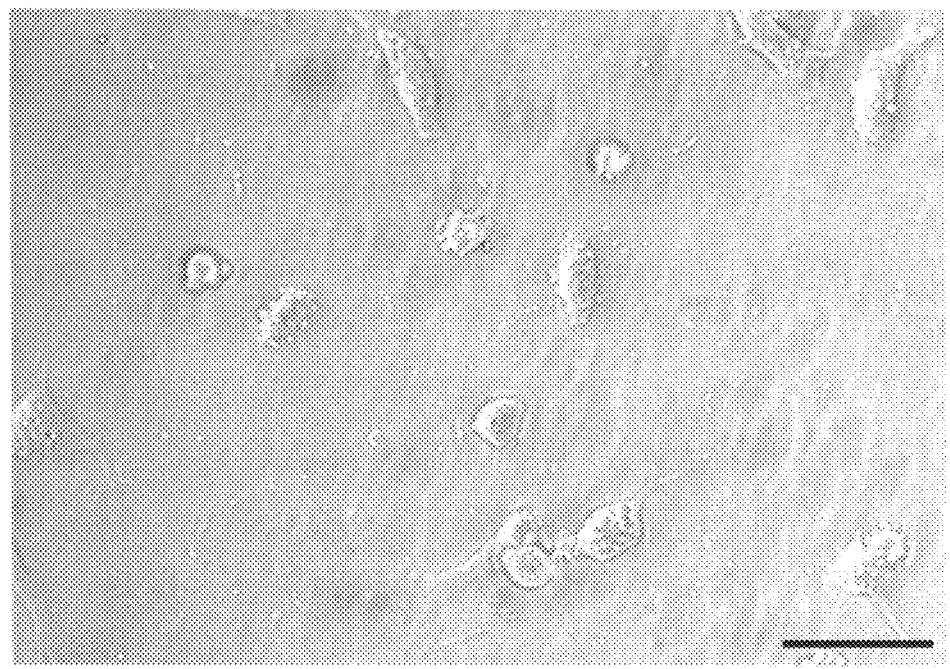
FIG. 2(b) is a photomicrograph of BAECs on PUU-PPD film after a 4-hour incubation under phase contrast, according to one embodiment. The length of the scale bar is 50 μm.
Figure 2C:
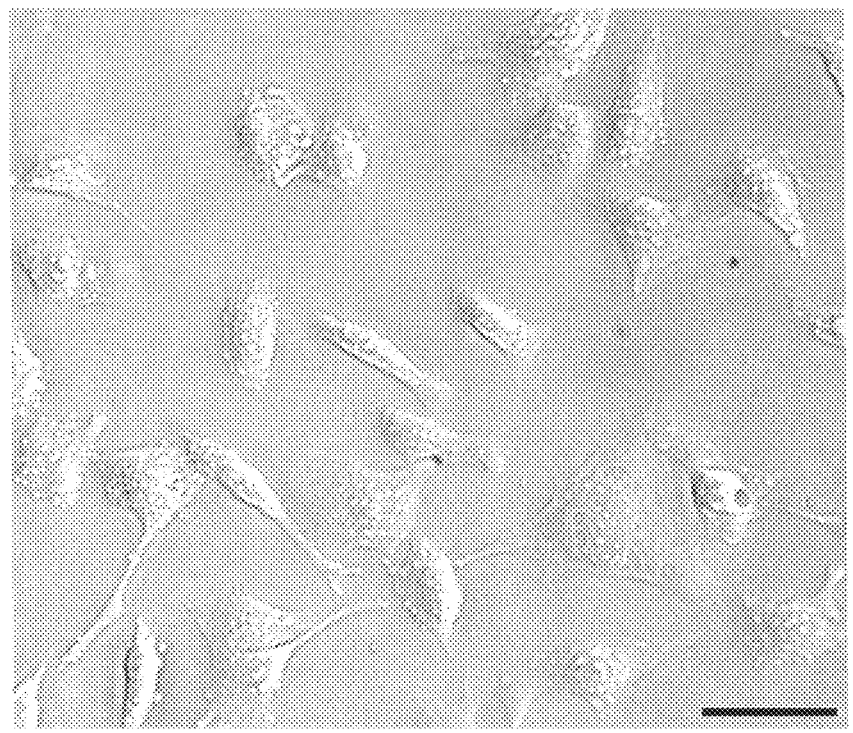
FIG. 2(c) is a photomicrograph of BAECs on PUU-YIGSR films after a 4-hour incubation under phase contrast films after a 4-hour incubation, according to one embodiment. The length of the scale bar is 50 μm.
Figure 3A:
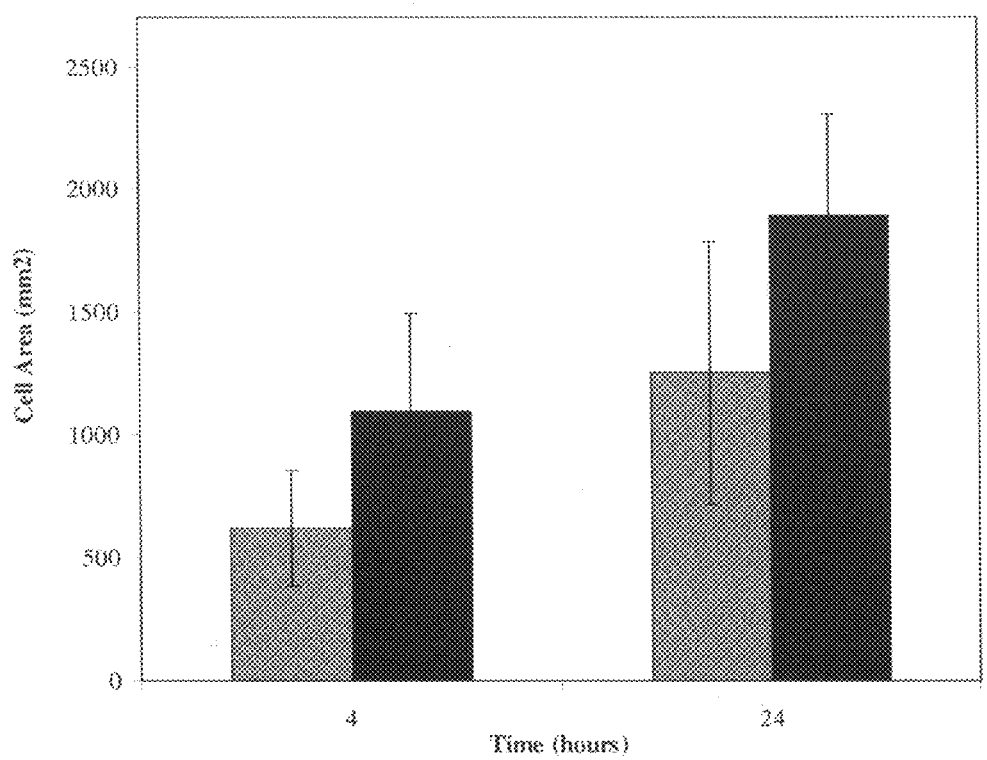
FIG. 3(a) is a graph comparing the cell surface area spreading of BAECs on PUU-PPD and PUU-YIGSR films, according to one embodiment.
Figure 3B:
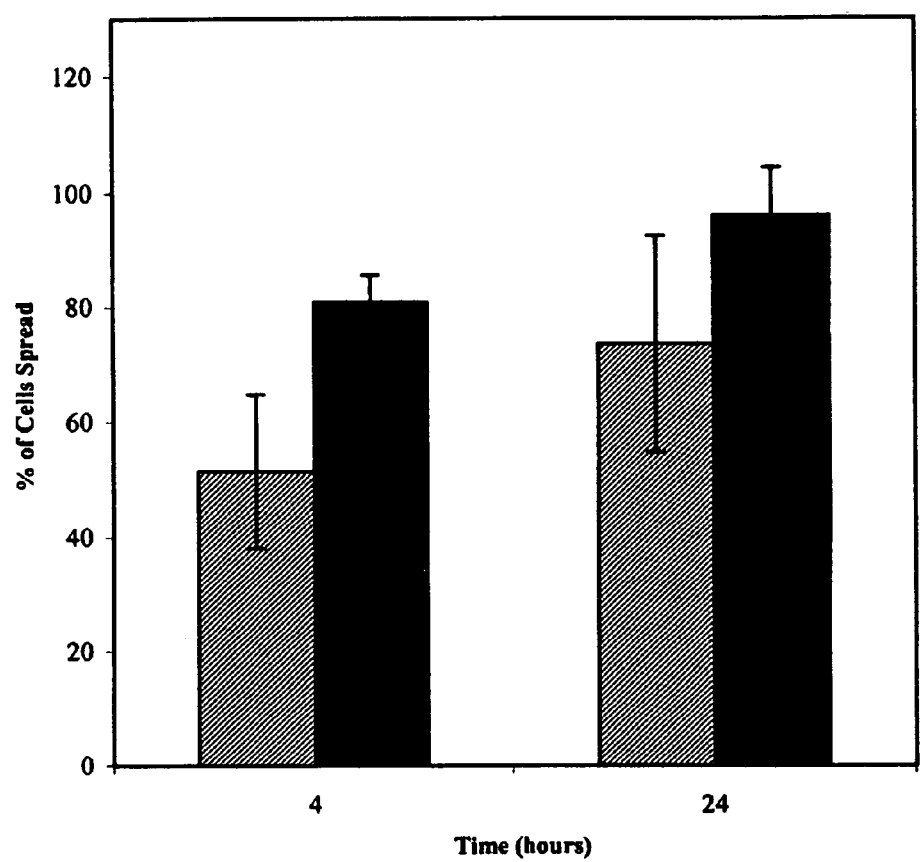
FIG. 3(b) is a graph comparing the spreading of BAECs on PUU-PPD and PUU-YIGSR films as measured by the percent of cells that were spread, according to one embodiment.

Next, analysis was performed to identify whether the peptides incorporated into the polymer backbone could enhance BAEC adhesion and spreading. The attachment of BAECs on polyurethane films is shown in FIG. 2(a)-(c). The number of adherent cells increased with increasing incubation time. The number of adherent cells on PUU-YIGSR was significantly higher than on PUU-PPD after both 4 and 24 hours of incubation (p<0.01 for 4 hours and p<0.05 for 24 hours). Spreading of endothelial cells on polyurethane films was also investigated (FIG. 3(a)-(b)). Cell areas and the percent of spread cells increased with increasing incubation time for both surfaces. However, BAECs on PUU-YIGSR showed significantly greater cell surface area and percent of spreading cells than on PUU-PPD after both 4 and 24 hours of culture (p<0.01).

Figure 4A:
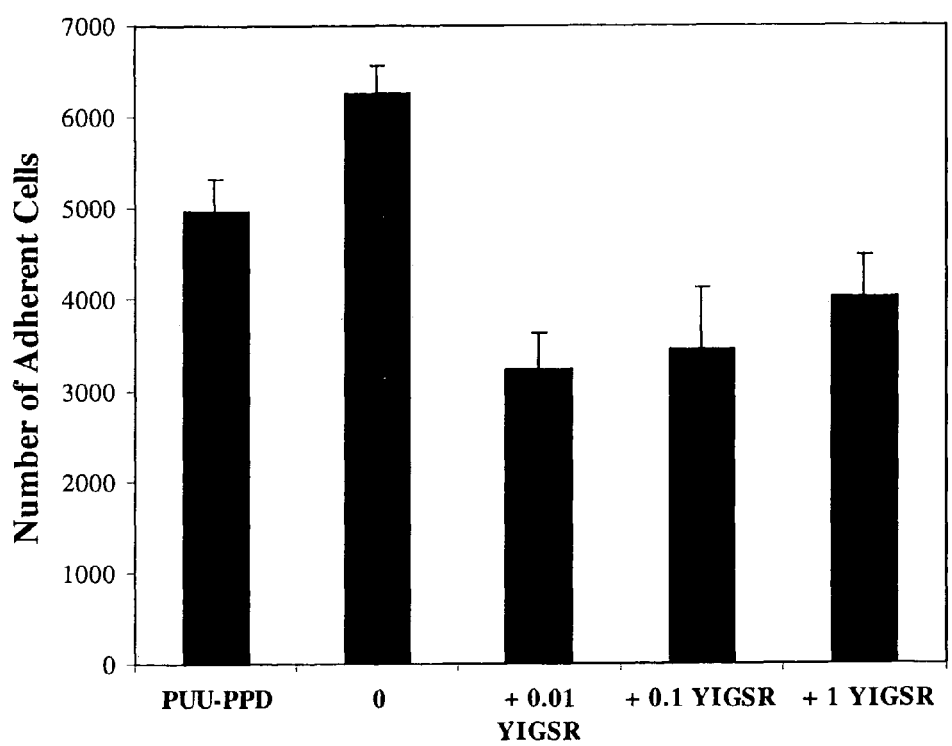
FIG. 4(a) is a graph comparing the competitive inhibition of attachment and spreading of BAECs by soluble YIGSR at three different concentrations (0.01, 0.1, and 1 mM) compared to PUU-PPD as measured by adherent cells, according to one embodiment.
Figure 4B:
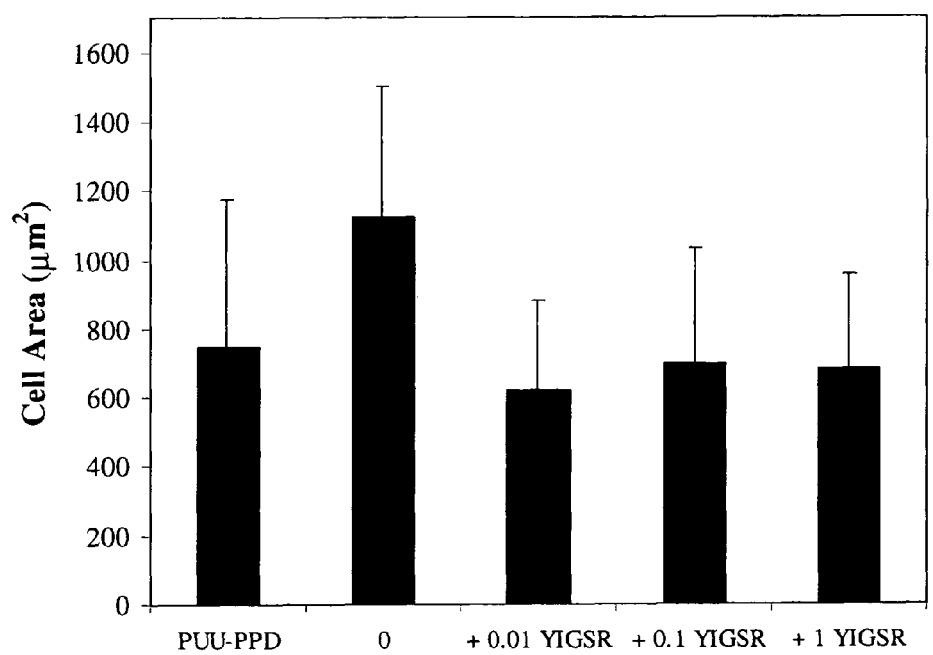
FIG. 4(b) is a graph comparing the competitive inhibition of attachment and spreading of BAECs by soluble PUU-YIGSR at three different concentrations (0.01, 0.1, and 1 mM) compared to PUU-PPD as measured by cell surface area, according to one embodiment.
Figure 4C:
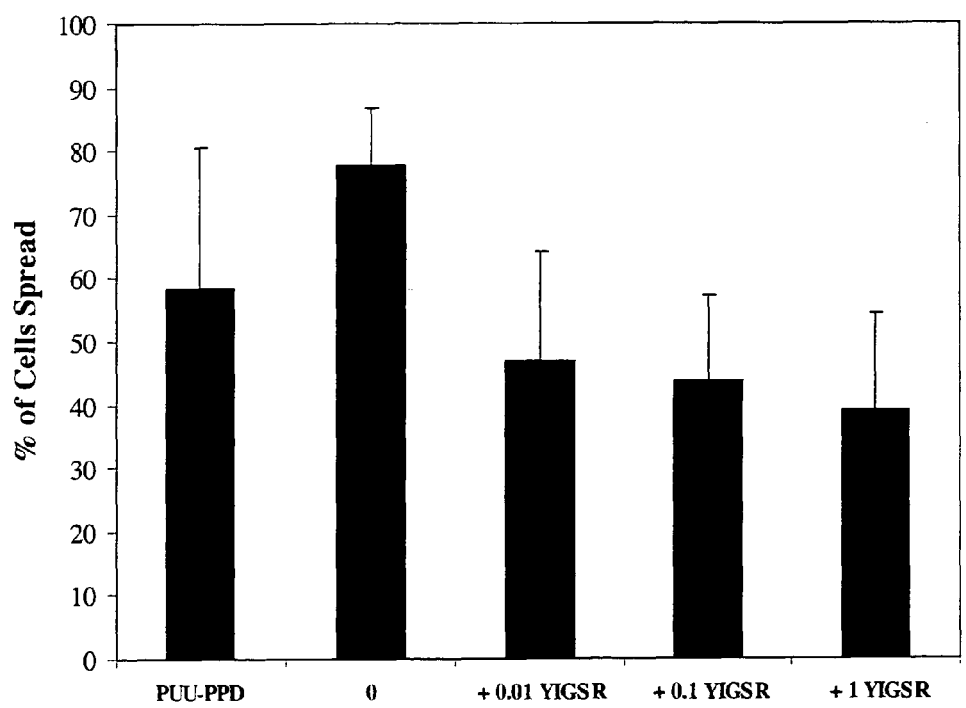
FIG. 4(c) is a graph comparing the competitive inhibition of attachment and spreading of BAECs by soluble PUU-YIGSR at three different concentrations (0.01, 0.1, and 1 mM) compared to PUU-PPD as measured by the percent of cells that were spread, according to one embodiment.

In order to ensure that the improved cell adhesion and spreading were due to biospecific interactions with YIGSR peptides in the bioactive polymer, competitive inhibition of endothelial cell attachment and spreading was investigated using soluble YIGSR peptides in the culture media. As shown in FIG. 4(a), the number of adherent cells on PUU-YIGSR was significantly greater than on PUU-PPD, but the values were reduced in the presence of soluble YIGSR peptides over the entire ranges of the soluble peptide concentrations. Cell surface area and the percent of cell spreading were also reduced over the entire range of soluble peptide concentrations (FIG. 4(b) and (c)). Thus, these results indicate that the improved cell adhesion and spreading were specifically mediated by YIGSR-sensitive cell adhesion receptors.

BAEC Proliferation, Migration, and ECM Production on a PUU-YIGSR Peptide-Modified Polyurethane Film.

The effect of peptide incorporation on endothelial cell proliferation was examined using immunohistochemical staining with a PCNA-HOURSP conjugate. PCNA is present in cells in the S-phase of mitosis and indicates proliferative activity. The percent of PCNA-positive cells on PUU-YIGSR was significantly greater than on PUU-PPD after 48 hours of culture (78±5% vs. 60±4%, p<0.001).

Figure 5:
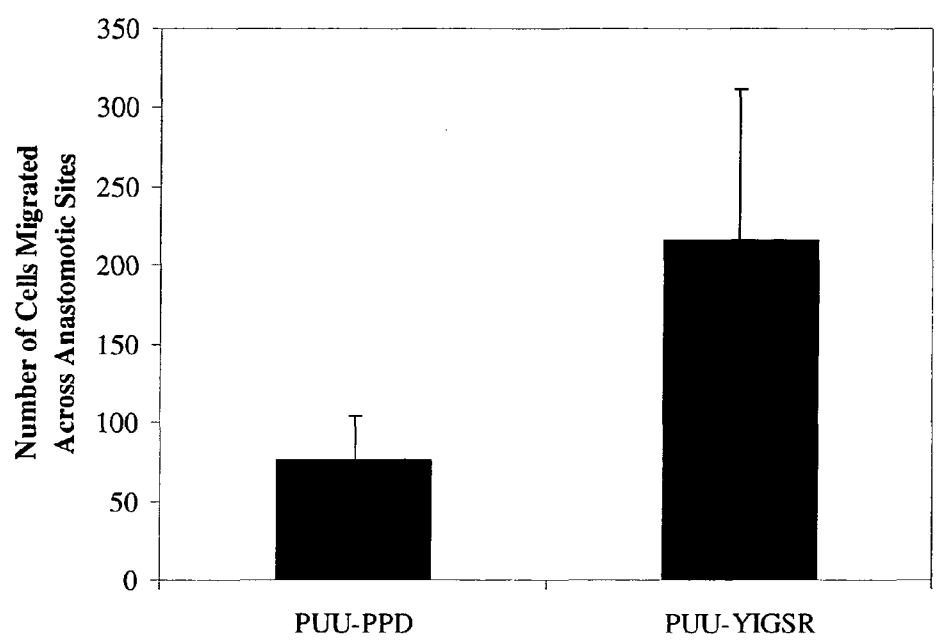
FIG. 5 is a graph showing the migration of BAECs across simulated anastomotic sites from collagen I surfaces to PUU-PPD and PUU-YIGSR surfaces, according to one embodiment.

A fence-style assay was used to assess endothelial cell migration on polyurethane films. The number of cells that had migrated over the original boundary was significantly greater on PUU-YIGSR compared to that on PUU-PPD (63±8 vs. 37±12, p<0.05). In addition, endothelialization at an anastomotic site was simulated in an in vitro system. It is important for endothelial cells to migrate across the anastomotic site, from a natural ECM environment to the synthetic polymer material, for example, to cover the surface of an implanted graft. A fence-style assay was also used, and the number of cells that had migrated over the original boundary from the collagen I-coated surface to the polyurethane surface was determined using a phase contrast microscope. On PUU-YIGSR, more cells migrated across anastomotic sites than on PUU-PPD (216±95 vs. 76±29, p<0.02), as shown in FIG. 5.

To evaluate extracellular matrix (ECM) production, cells were incubated in the presence of $^3$H-glycine on polyurethane films. Matrix production was determined by incorporation of $^3$H-glycine into glycoprotein, elastin, and collagen of ECM by using sequential enzyme digests. The ECM production by BAECs was significantly increased on PUU-YIGSR compared to PUU-PPD (0.0075±0.0004 cpm/cell vs. 0.0055±0.001 cpm/cell, p<0.05).

Platelet Adhesion on a PUU-YIGSR Peptide-Modified Polyurethane Film.

Figure 6:
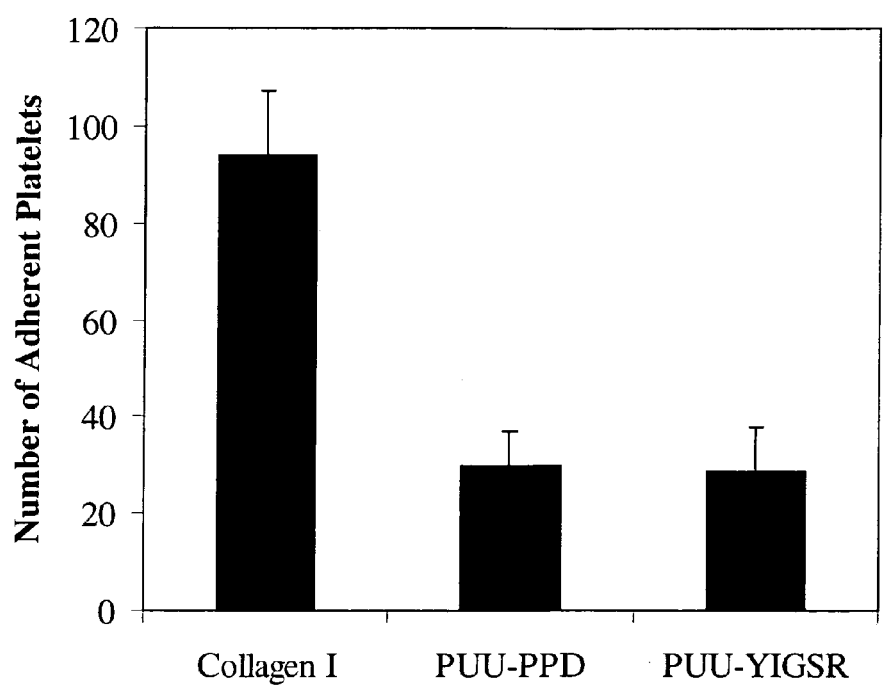
FIG. 6 is a graph showing platelet adhesion to PUU-YIGSR compared to collagen I, according to one embodiment.

Since some peptides such as RGD support adhesion of platelets, the effect of the YIGSR peptide sequences incorporated in the polymer backbone on platelets adhesion was examined using mepacrine-labeled whole blood (FIG. 6). Platelets adhesion on PUU-PPD (29.7±7.1) and PUU-YIGSR (28.6±9.1) were dramatically lower than on collagen I (94.1±13.1), the positive control. Additionally, there was no significant difference in the number of adherent platelets between PUU-PPD and PUU-YIGSR, indicating that the incorporation of the YIGSR adhesion peptide did not enhance thrombogenicity.

Synthesis and Characterization of a PUU-PEG-YIGSR Peptide-Modified Polyurethane.

The NMR spectra of certain embodiments of the peptide-modified polyurethanes of the present invention were obtained and characterized as described above. The characteristic proton peaks of tyrosine (6.5-7.0 ppm) from the GGGYIGSRGGGK sequence were assigned, indicating the successful incorporation of the peptide sequence into the PUU-YIGSR polymer. The peaks of prepolymer, PUU-PPD-PEG, and PUU-PEG-YIGSR were also assigned and characterized. Based on the number of protons calculated from peak intensities, the peptide concentration in the polymer was approximately 56 µmol/g. The surface peptide concentration of PUU-PEG-YIGSR film was also estimated to be approximately 0.2 nmol/cm$^2$ using the polymer density and the thickness of the monolayer.

FT-IR spectra of the polyurethanes were also obtained and characterized. The incorporation of the PEG as a soft segment did not affect FT-IR spectra compared to PUU-PPD. For both PUU-PPD-PEG and PUU-PEG-YIGSR, peaks for hard segments were observed at 1640 cm$^{-1}$ (hydrogen-bonded urea carbonyl), at 1720 cm$^{-1}$ (urethane carbonyl peaks for hydrogen bond), and at 1740 cm$^{-1}$ (urethane carbonyl peaks for free bond). The CH stretch peaks of the soft segment, PTMO, appeared at 2850 cm$^{-1}$ and 2940 cm$^{-1}$, and the hydrogen-bonded NH peak also appeared at 3310 cm$^{-1}$.

Figure 7:
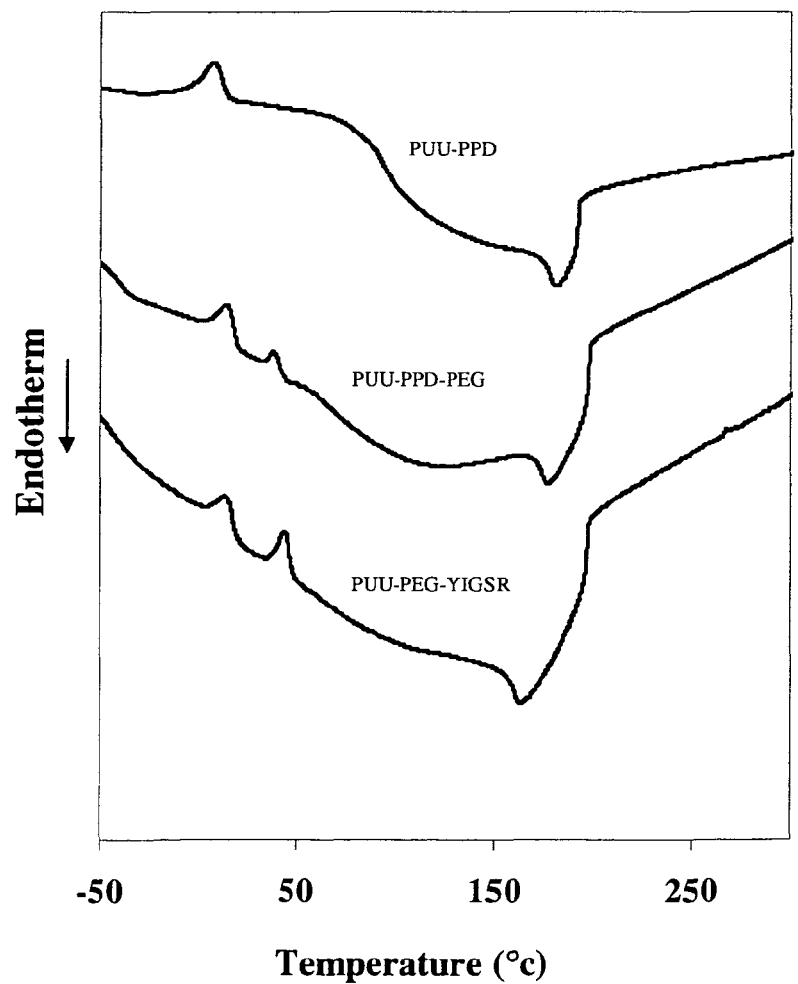
FIG. 7 is a graph showing DSC thermograms of PUU-PPD, PUU-PPD-PEG, and PUU-PEG-YIGSR, according to one embodiment.

Thermal behaviors from DSC provide successful incorporation of PEG as a soft segment as shown in FIG. 7. The Tg of PUU-PPD was observed at 9° C. However, two distinct Tg were observed at 14° C. and 40° C. for PUU-PPD-PEG and PUU-PEG-YIGSR, likely caused by PTMO and PEG, respectively. The melting point (Tm) of PUU-PPD and PUU-PPD-PEG was determined about 180° C., and the Tm of PUU-PEG-YIGSR was approximately 165° C.

The number-average molecular weight (Mn), the weight-average molecular weight (Mw), and the polydispersity index (PDI) were determined by GPC. PUU-PPD-PEG and PUU-PEG-YIGSR had similar molecular weights (PUU-PPD: Mn=113,489, Mw=153,973, PDI=1.36, PUU-PPD-PEG: Mn=92,645, Mw=124,072, PDI=1.34 and PUU-PEG-YIGSR: Mn=96,675, Mw=116,103, PDI=1.20).

The surface atomic concentration was determined using ESCA with various take-off angles (PUU-PPD-PEG: C=58.4%, N=12.1%, O=30.4% at 10° and C=75.1%, N=0.4%, O=24.8% at 45°, PUU-PEG-YIGSR: C=58.7%, N=12.0%, O=29.0% at 100 and C=73.0%, N=0.9%, O=25.9% at 45°). Nitrogen (N) and oxygen (O) concentrations are related to the urea linkages of the hard segments and amide linkages of the peptide sequences. The higher level of nitrogen and oxygen detected on the PUU-PEG-YIGSR at 45° indicates that the GGGYIGSRGGGK peptide sequences were successfully incorporated into the polymer backbone and present at the surface of the material.

Water contact angle measurement demonstrated that the contact angle dropped significantly on PEG-modified polyurethanurea, PUU-PPD-PEG (59.6±1.7) and PUU-PEG-YIGSR (50.6±1.3), compared to PUU-PPD (81.6±1.1). The contact angle of PUU-PEG-YIGSR was also significantly lower than that of PUU-PPD-PEG. Thus, the combination of the incorporated peptides and PEG made the surface of PUU-PEG-YIGSR more hydrophilic and polar.

The incorporation of the PEG and peptide sequences into the polyurethane backbone affected the mechanical properties. The mechanical properties of PUU-PPD-PEG (elastic modulus: 0.44±0.1 MPa, tensile strength: 3.1±0.4 MPa, elongation: 370±84.3%) were significantly lower compared to PUU-PPD (elastic modulus: 1.1±0.2 MPa, tensile strength 27.2±1.2 MPa, elongation: 2580±544.7%). However, the incorporation of the peptide sequences increased the mechanical properties of PUU-PEG-YIGSR (elastic modulus: 0.21±0.1 MPa, tensile strength 9.2±1.8 MPa, elongation: 3532±222.8%).

Adhesion and Spreading of BAECs on a PUU-PEG-YIGSR Peptide-Modified Polyurethane Film.

Figure 8A:
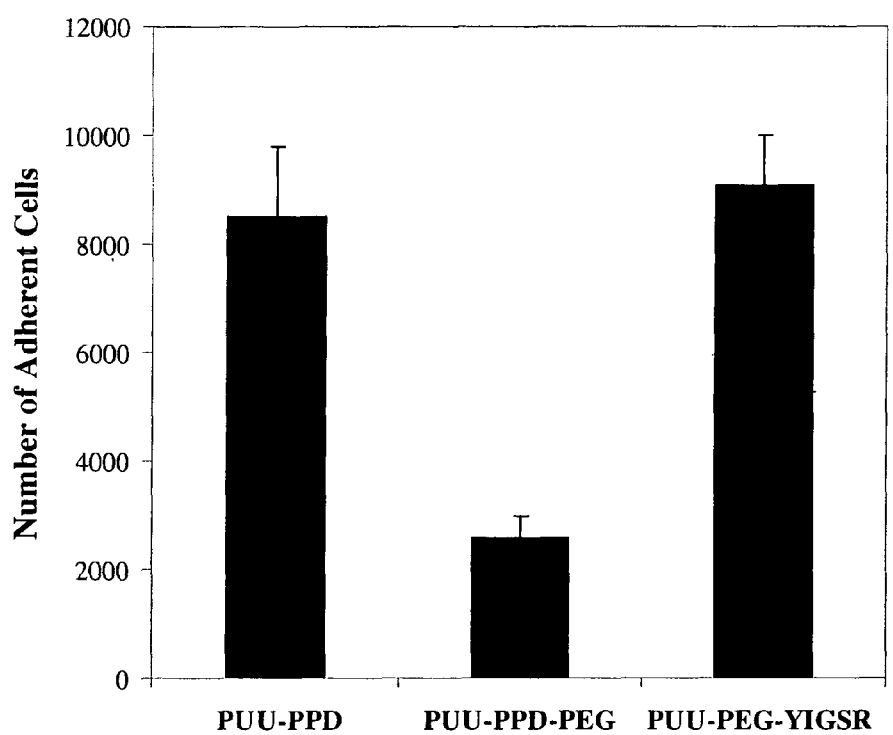
FIG. 8(a) is a graph comparing the number of adherent BAECs to PUU-PPD, PUU-PPD-PEG, and PUU-PEG-YIGSR, according to one embodiment.
Figure 8B:
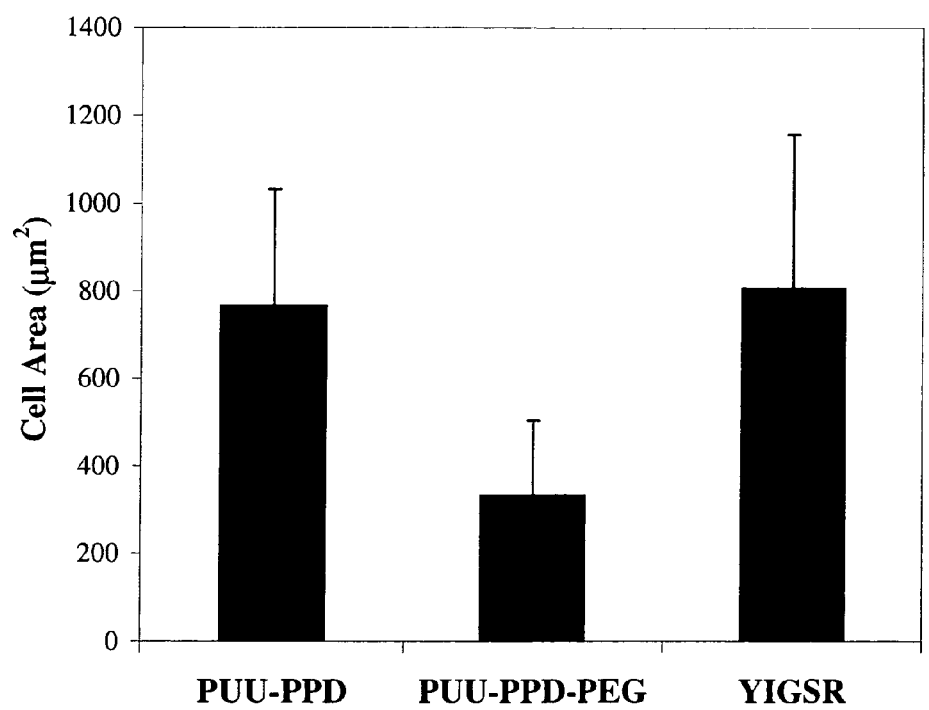
FIG. 8(b) is a graph comparing the number of adherent BAECs to PUU-PPD, PUU-PPD-PEG, and PUU-PEG-YIGSR as measured by cell surface area, according to one embodiment.
Figure 8C:
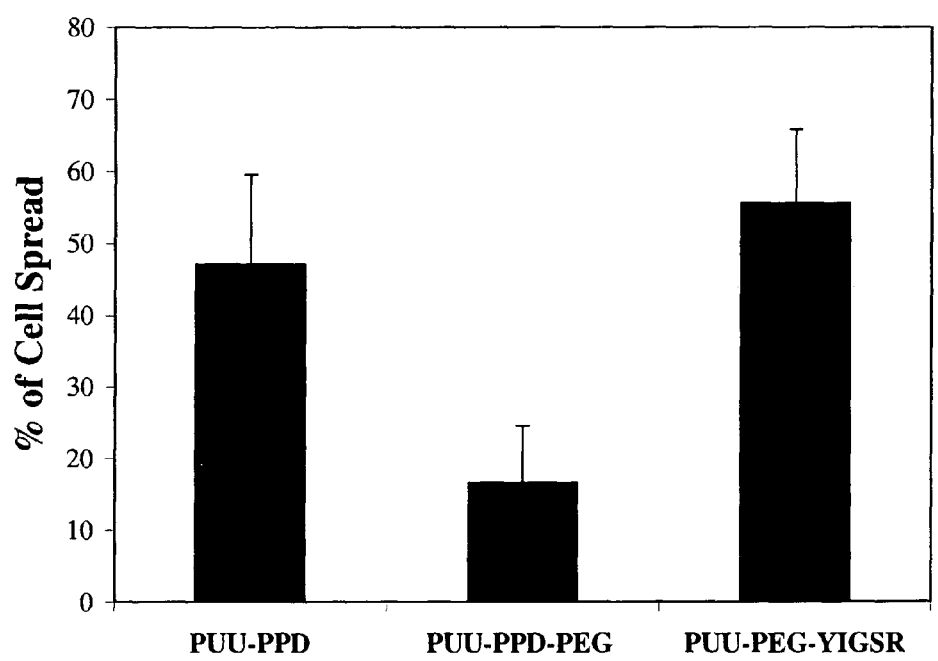
FIG. 8(c) is a graph comparing the number of adherent BAECs to PUU-PPD, PUU-PPD-PEG, and PUU-PEG-YIGSR as measured by the percent of cells that were spread, according to one embodiment.
Figure 9A:
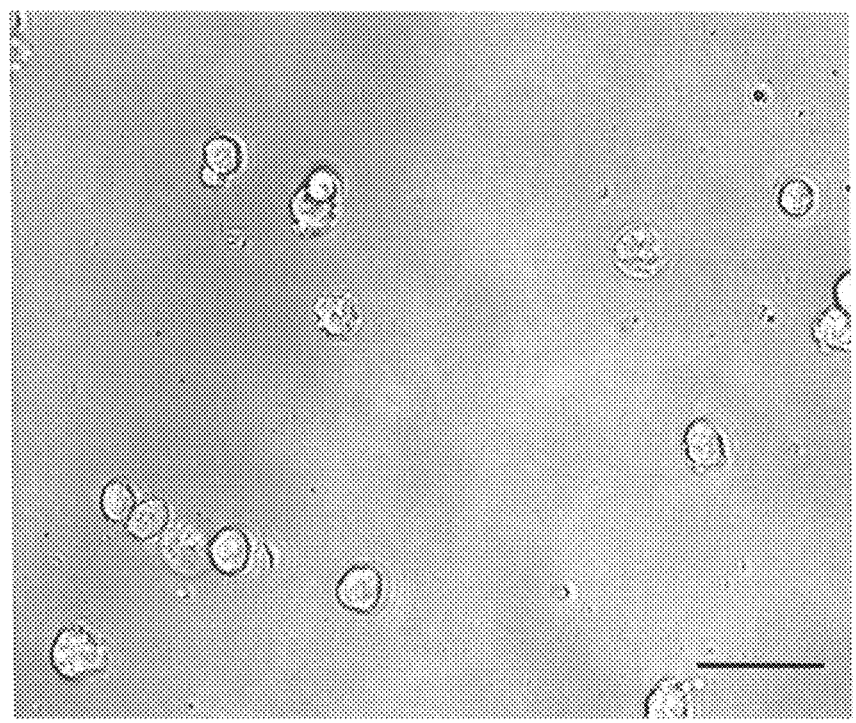
FIG. 9(a) is a photomicrograph of BAECs on PUU-PPD-PEG using phase contrast after a 4-hour incubation, according to one embodiment. The length of the scale bar is 50 μm.
Figure 9B:
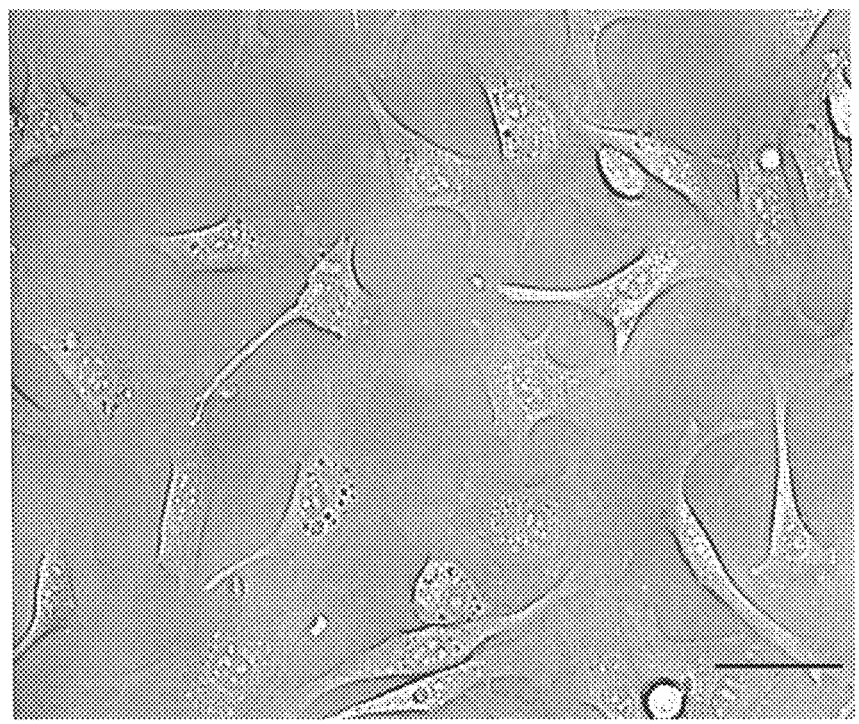
FIG. 9(b) is a photomicrograph of BAECs on PUU-PEG-YIGSR using phase contrast after a 4-hour incubation, according to one embodiment. The length of the scale bar is 50 μm.

An analysis was performed to determine whether the incorporation of PEG and peptides into certain peptide-modified polyurethanes of the present invention impacted BAEC attachment and spreading. BAECs were seeded on PUU-PPD, PUU-PPD-PEG, and PUU-PEG-YIGSR polyurethane films, and adhesion and spreading were investigated after 4 hours. The number of adherent cells on PUU-PPD-PEG was significantly lower than on PUU-PPD (p<0.005) as shown in FIG. 8(a). However, cell attachment increased dramatically on PUU-PEG-YIGSR (p<0.001). There was no statistical difference for endothelial cell attachment on PUU-PPD versus PUU-PEG-YIGSR. Similar results were also observed for cell area (see FIG. 8(b)) and percent of cell spreading (see FIG. 8(c)). FIG. 9(a)-(b) also shows phase contrast micrographs of endothelial cells on PUU-PPD-PEG and PUU-PEG-YIGSR films. The incorporation of PEG into PUU-PPD decreased cell surface area and percent of cell spreading, but the incorporation of the peptides promoted cell spreading in PUU-PEG-YIGSR. Few cells attached; most cells that did attach were round shape and did not spread on PUU-PPD-PEG. However, a greater number of cells attached and completely spread on PUU-PEG-YIGSR.

Figure 10A:
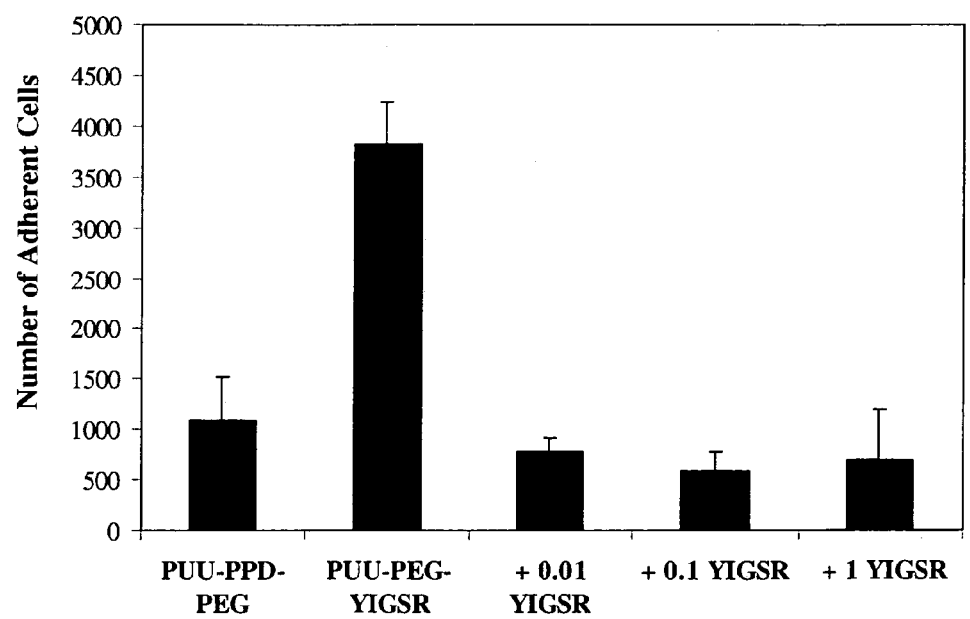
FIG. 10(a) is a graph comparing the competitive inhibition of attachment and spreading of BAECs by soluble YIGSR at three different concentrations (0.01, 0.1, and 1 mM) compared to PUU-PPD-PEG and PUU-PEG-YIGSR as measured by adherent cells, according to one embodiment.
Figure 10B:
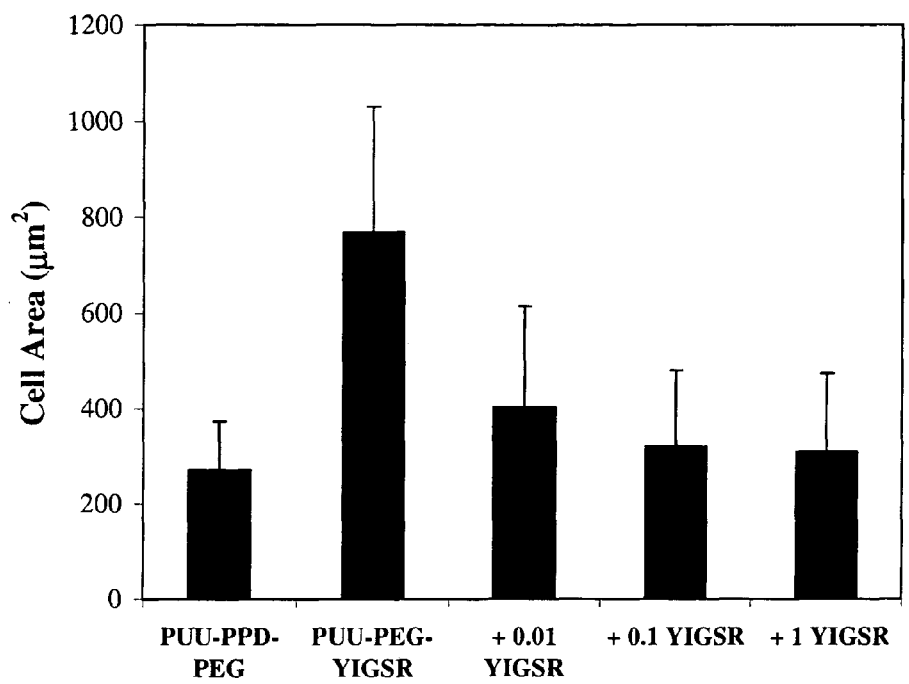
FIG. 10(b) is a graph comparing the competitive inhibition of attachment and spreading of BAECs by soluble YIGSR at three different concentrations (0.01, 0.1, and 1 mM) compared to PUU-PPD-PEG and PUU-PEG-YIGSR as measured by cell surface area, according to one embodiment.
Figure 10C:
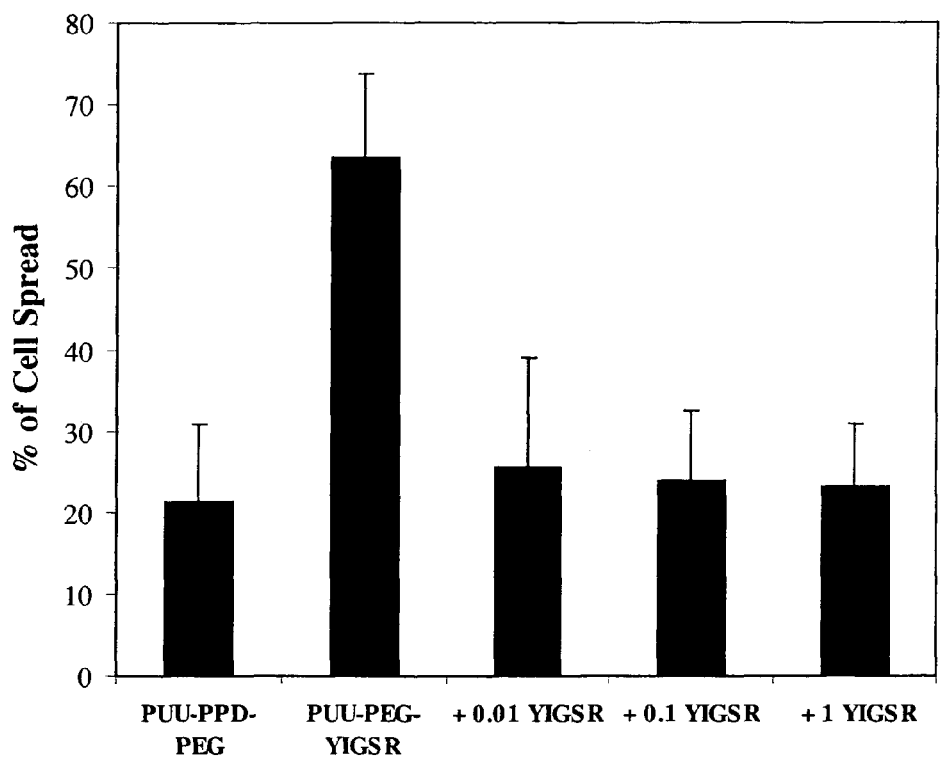
FIG. 10(c) is a graph comparing the competitive inhibition of attachment and spreading of BAECs by soluble YIGSR at three different concentrations (0.01, 0.1, and 1 mM) compared to PUU-PPD-PEG and PUU-PEG-YIGSR as measured by the percent of cells that were spread, according to one embodiment.
Figure 11A:
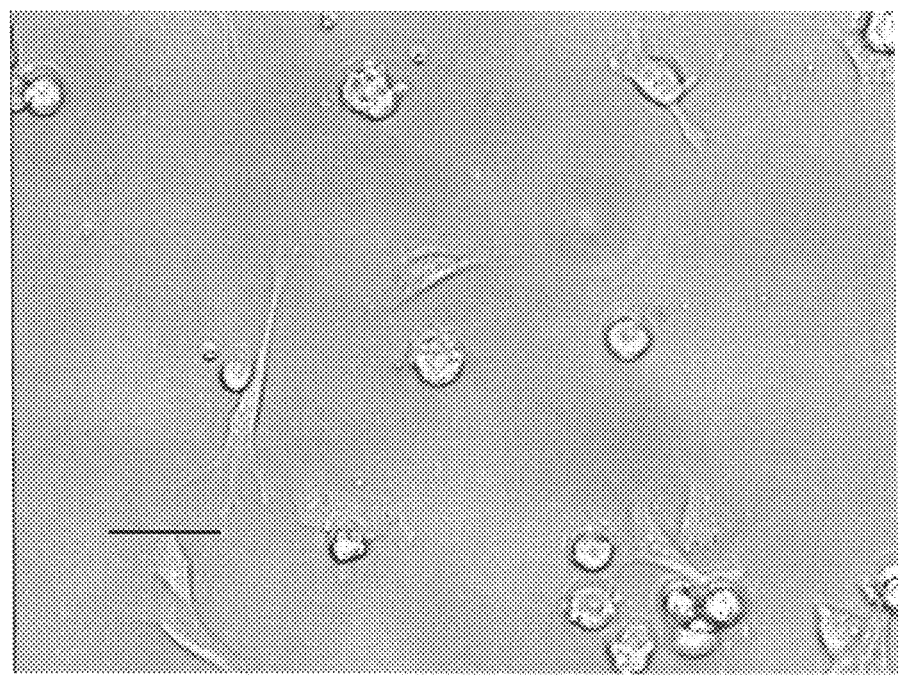
FIG. 11(a) is a photomicrograph showing the competitive inhibition of attachment and spreading of BAECs incubated with PUU-PEG-YIGSR using phase contrast after a 4-hour incubation, according to one embodiment. The length of the scale bar is 50 μm.
Figure 11B:
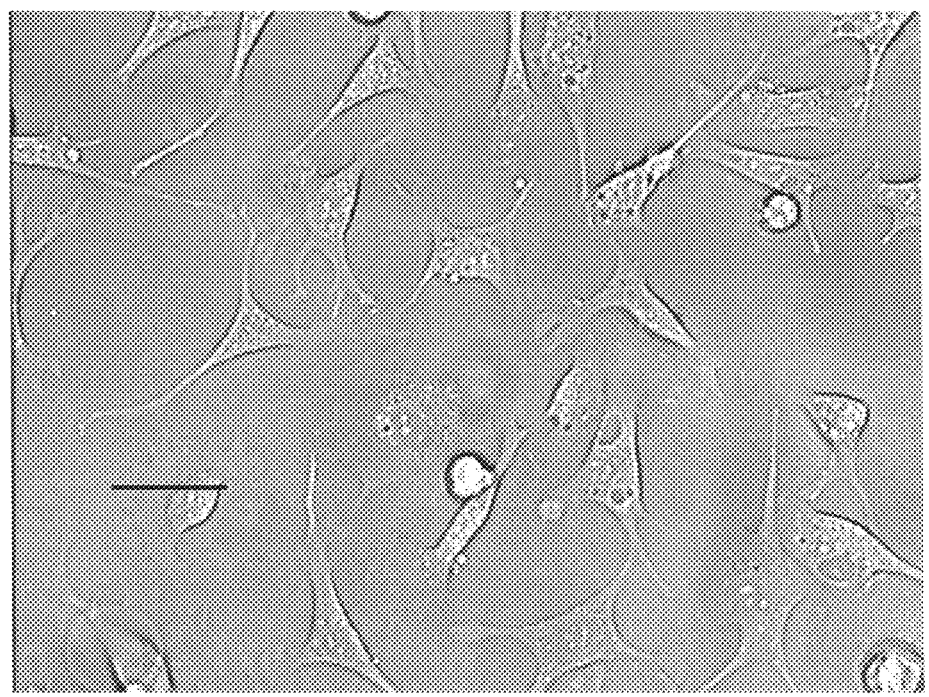
FIG. 11(b) is a photomicrograph showing the competitive inhibition of attachment and spreading of BAECs incubated with with PUU-PEG-YIGSR and 0.01 mM soluble YIGSR using phase contrast after a 4-hour incubation, according to one embodiment. The length of the scale bar is 50 μm.
Figure 11C:
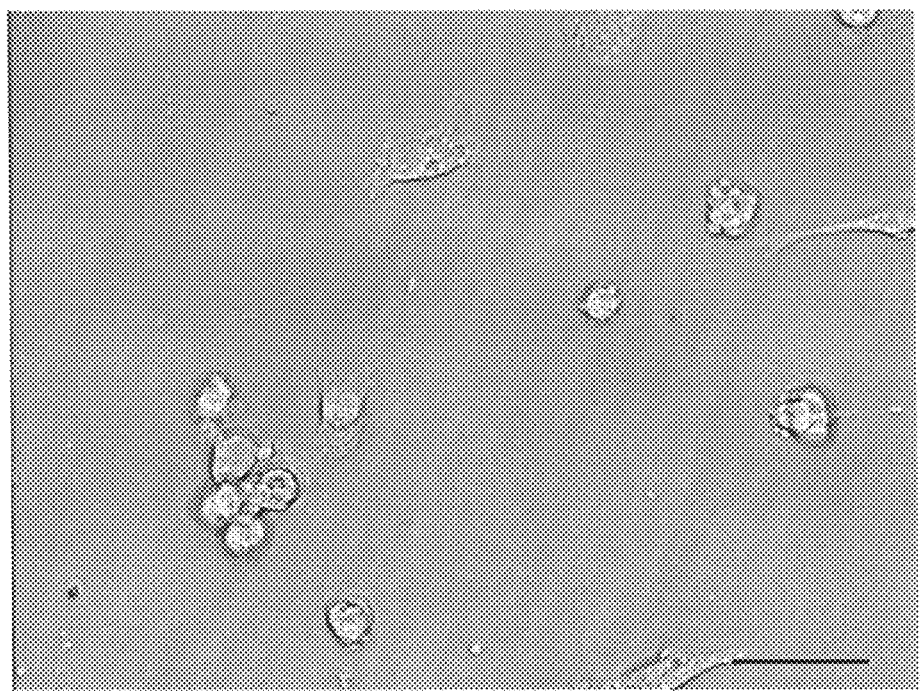
FIG. 11(c) is a photomicrograph showing the competitive inhibition of attachment and spreading of BAECs incubated with PUU-PEG-YIGSR and 0.1 mM soluble YIGSR using phase contrast after a 4-hour incubation, according to one embodiment. The length of the scale bar is 50 μm.
Figure 11D:
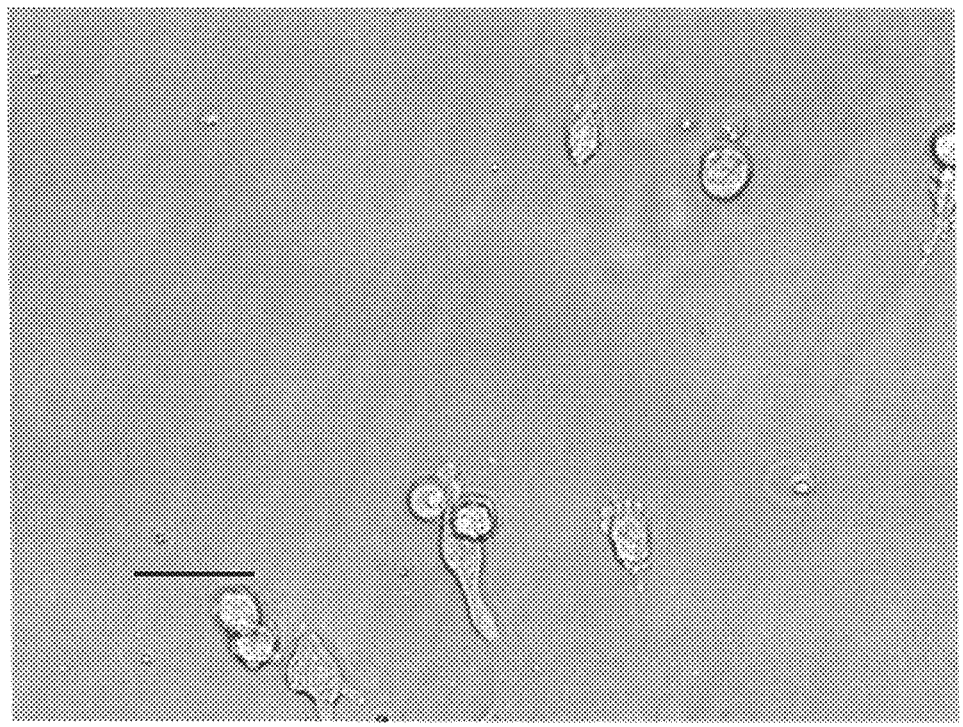
FIG. 11(d) is a photomicrograph showing the competitive inhibition of attachment and spreading of BAECs incubated with with PUU-PEG-YIGSR and 1 mM soluble YIGSR using phase contrast after a 4 hour incubation, according to one embodiment. The length of the scale bar is 50 μm.

To ensure that improved cell adhesion and spreading were mediated by YIGSR specific cell adhesion receptors, competitive inhibition of endothelial cell attachment and spreading was studied using soluble YIGSR peptides in culture media. The adhesion of endothelial cells dramatically increased on PUU-PEG-YIGSR compared to that on PUU-PPD-PEG. However, adhesion of BAECs was reduced in the presence of soluble YIGSR peptides over the entire ranges of the soluble peptide concentrations (0.01, 0.1, and 1 mM) as shown in FIG. 10(a)-(c). Similar results were also observed in cell surface area and percent of cell spreading. Fewer cells attached, and most attached cells were round in shape over the entire range of soluble peptide concentrations as shown in FIG. 11(a)-(d). These results suggest that adhesion of BAECs to this peptide-modified material is predominantly mediated by specific receptor-ligand interactions.

Migration of BAECs on a PUU-PEG-YIGSR Peptide-Modified Polyurethane Film.

Figure 12A:
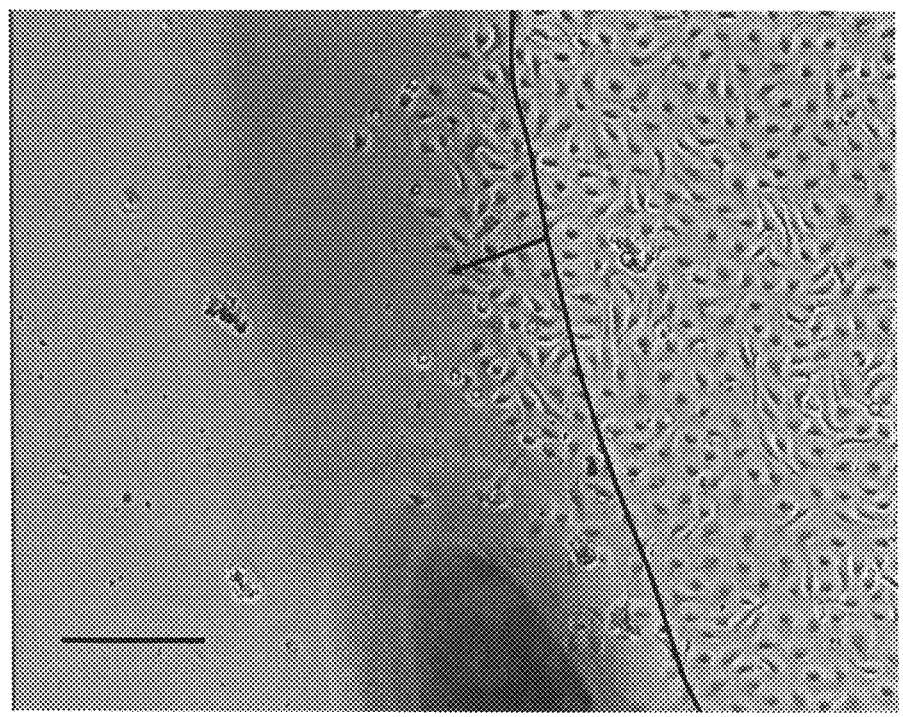
FIG. 12(a) is a photomicrograph showing the migration of BAECs on PUU-PEG-YIGSR after 24 hours, according to one embodiment. The length of the scale bar is 200 μm.
Figure 12B:
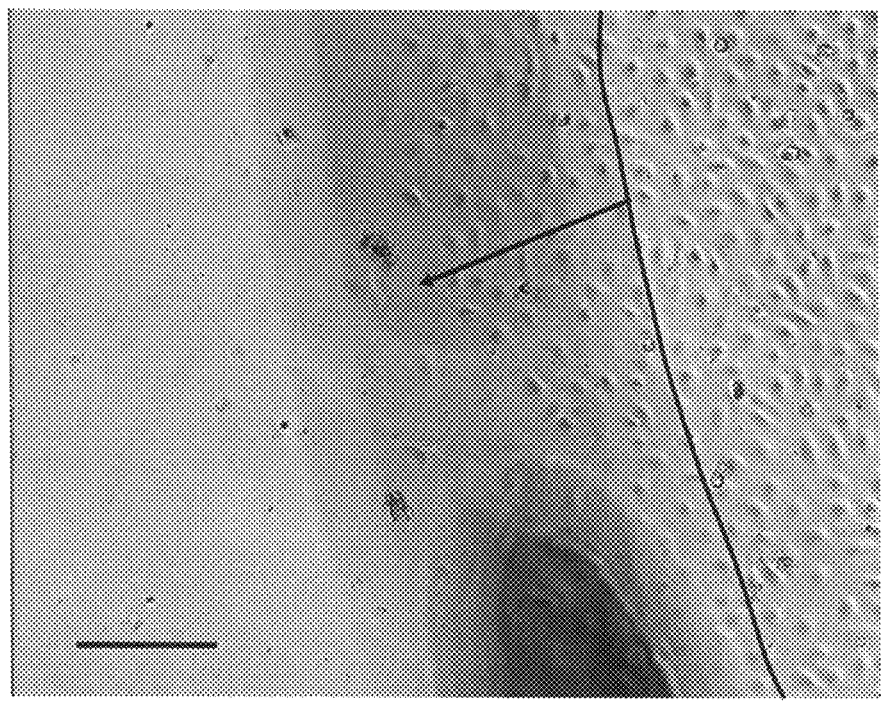
FIG. 12(b) is a photomicrograph showing the migration of BAECs on PUU-PEG-YIGSR after 48 hours, according to one embodiment. The length of the scale bar is 200 μm.
Figure 13:
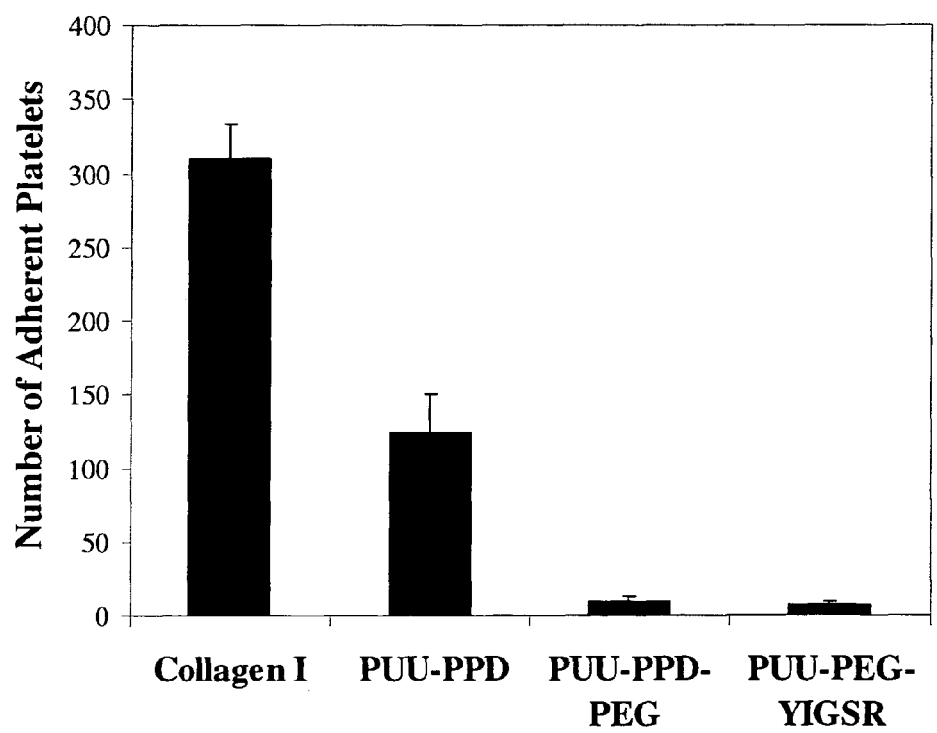
FIG. 13 is a graph showing the number of adherent platelets on the surfaces of collagen I, PUU-PPD, PUU-PPD-PEG, and PUU-PEG-YIGSR, according to one embodiment.
Figure 14A:
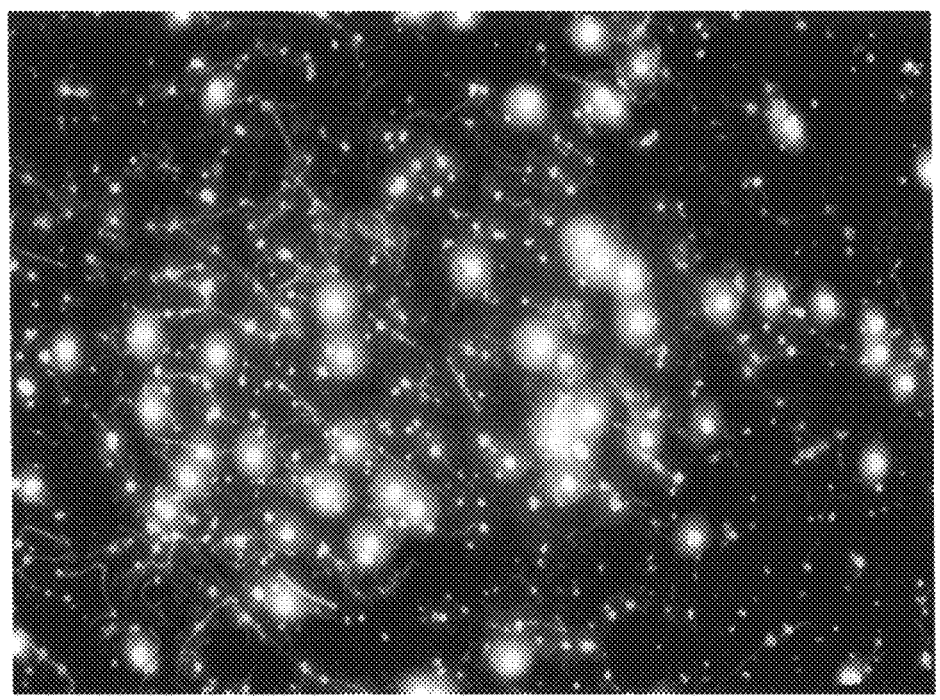
FIG. 14(a) is a fluorescent photomicrograph of platelets fluorescently labeled with mepacrine on collagen I, according to one embodiment.
Figure 14B:
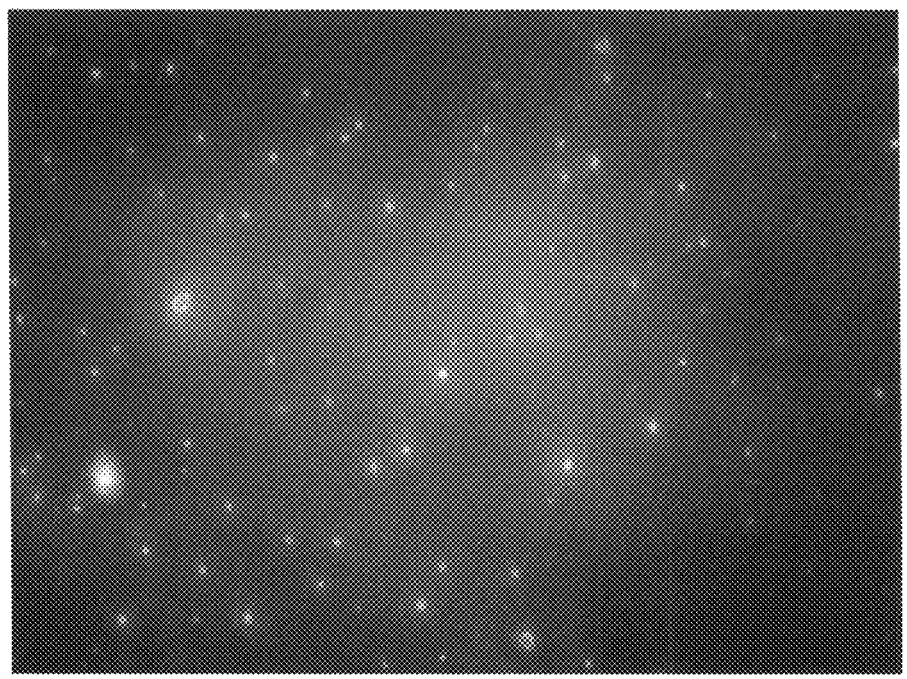
FIG. 14(b) is a fluorescent photomicrograph of platelets fluorescently labeled with mepacrine on PUU-PPD, according to one embodiment.
Figure 14C:
FIG. 14(c) is a fluorescent photomicrograph of platelets fluorescently labeled with mepacrine on PUU-PPD-PEG, according to one embodiment.
Figure 14D:
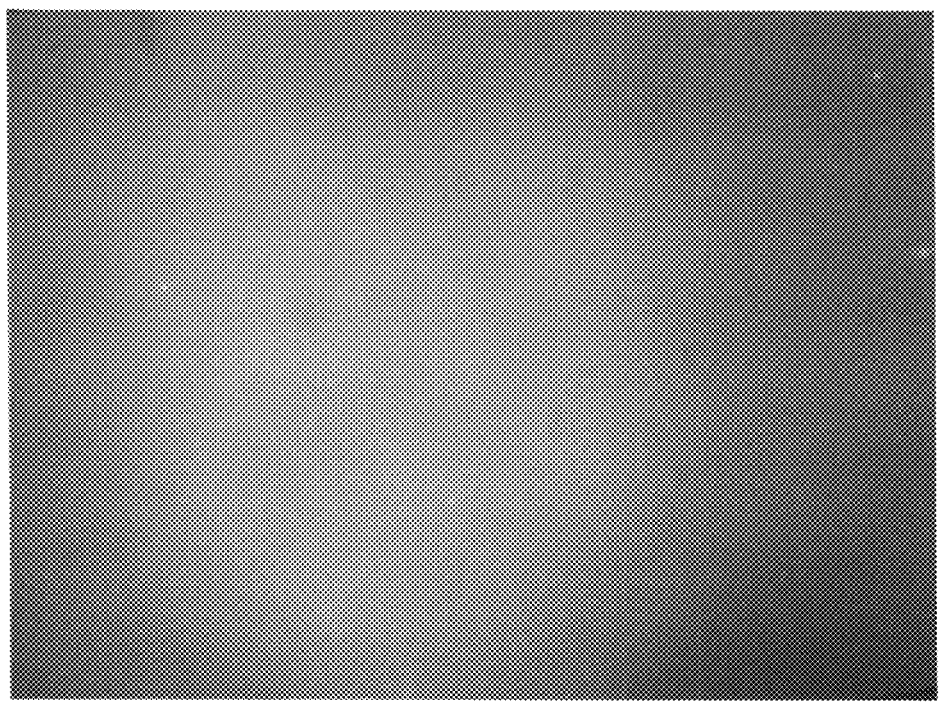
FIG. 14(d) is a fluorescent photomicrograph of platelets fluorescently labeled with mepacrine on PUU-PEG-YIGSR, according to one embodiment.

Because cell adhesion was low on PUU-PPD-PEG, migration of BAECs was evaluated only on PUU-PEG-YIGSR. As shown in FIG. 12(a)-(b), by 24 and 48 hours after seeding, significant migration beyond the original boundary was observed. This suggests that these materials will be capable of supporting autologous endothelialization.

Adhesion of Platelets on a PUU-PEG-YIGSR Peptide-Modified Polyurethane Film.

To generate a platelet-resistant material, peptide-modified polyurethanes were synthesized that included PEG as a portion of the soft segment domains. The adhesion of platelets on polyurethanurea films was evaluated using mepacrine-labled whole blood (FIG. 13 and FIG. 4(a)-(c)). Adhesion of platelets on PUU-PPD (1696±369/mm$^2$) was lower than on collagen I (4069±324/mm$^2$) but still substantial. However, there was almost no adhesion of the platelets on PUU-PPD-PEG (129±48/mm$^2$) or PUU-PEG-YIGSR (99±34/mm$^2$). Thus, PUU-PEG-YIGSR is a material that supports endothelial cell attachment and growth while being resistant to platelet adhesion and resultant complications.

Synthesis and Characterization of a PU-BD and a PU-BD-NO Peptide-Modified Polyurethane.

Figure 20:
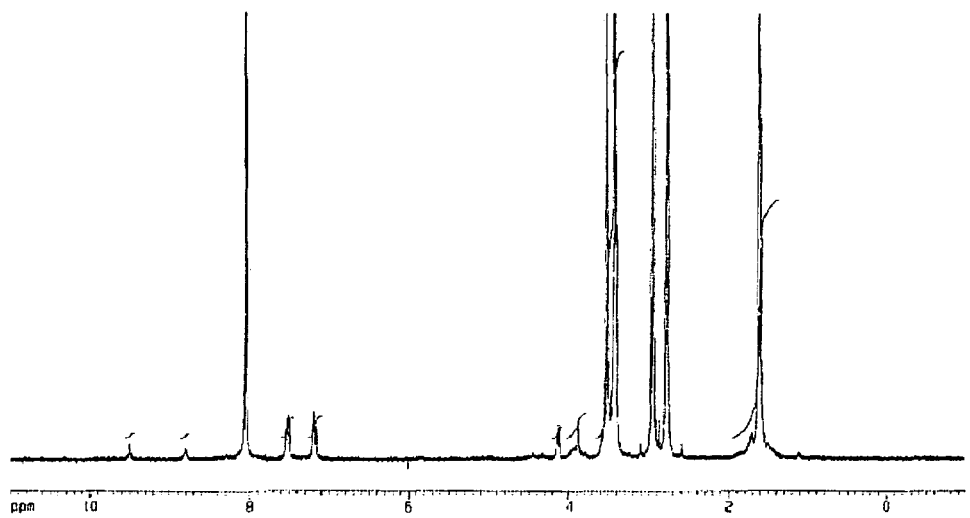
FIG. 20 is a $^1$H NMR spectrum of PU-BD-NO, according to one embodiment.

The conversion of free amine groups on the side chains of the SGGKKKKGGS peptide to diazeniumdiolates was measured using the Ninhydrin assay, and approximately 93% of amines were converted to NO-nucleophile complexes. PU-BD-NO was synthesized by incorporating the SGG[K[N(O)NO]$^-$]$_4$GGS sequence into the polymer backbone. The $^1$H NMR spectra of PU-BD and PU-BD-NO were obtained, and the characteristic proton peaks of the SGGKKKKGGS sequence indicated the successful incorporation of the peptide sequence into the polymer (FIG. 20). The peptide concentration of the polymer matrix was approximately 100 μmol/gram.

The number-average molecular weight ($M_n$), the weight-average molecular weight ($M_w$), and the polydispersity index (PDI) were determined by GPC using polystyrene standards. The PU-BD and PU-BD-NO polymers had similar molecular weights (PU-BD: $M_n$=54,701, $M_w$=75,167, PDI=1.37 and PU-BD-NO: $M_n$=50,323, $M_w$=71,006, PDI=1.41).

Figure 21A:
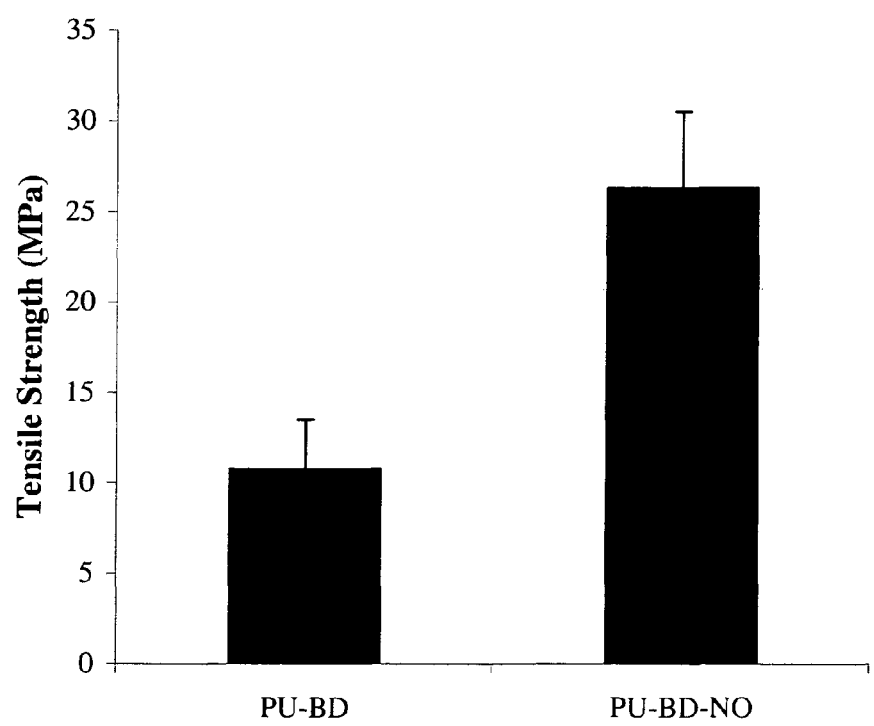
FIG. 21(a) is a graph showing the elastic modulus of PU-BD and PU-BD-NO, according to one embodiment.
Figure 21B:
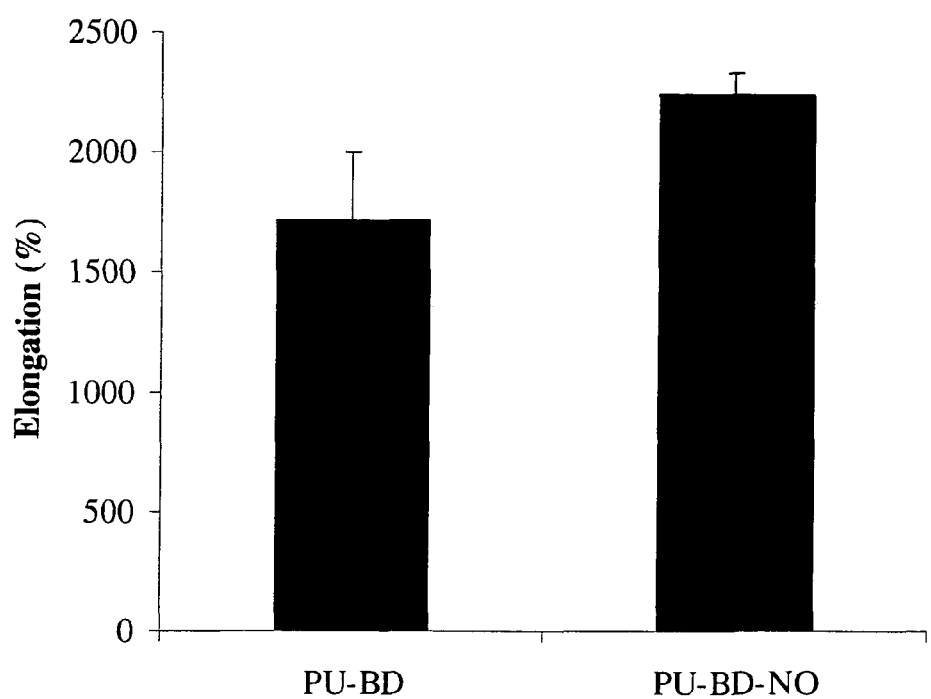
FIG. 21(b) is a graph showing the tensile strength of PU-BD and PU-BD-NO, according to one embodiment.

The incorporation of the peptides into the polymer backbone increased mechanical properties. Both the elastic modulus and tensile strength of PU-BD-NO were greater than those of PU-BD (FIG. 21). Subsequent NO release from PU-BD-NO should not alter the mechanical properties, as the original amine, in this case lysine, is the result. The mechanical properties of PU-BD-NO were comparable to commercial polyurethane vascular grafts as well as to native tissue.

NO Release Kinetics of a PU-BD-NO Peptide-Modified Polyurethane Film.

Figure 22:
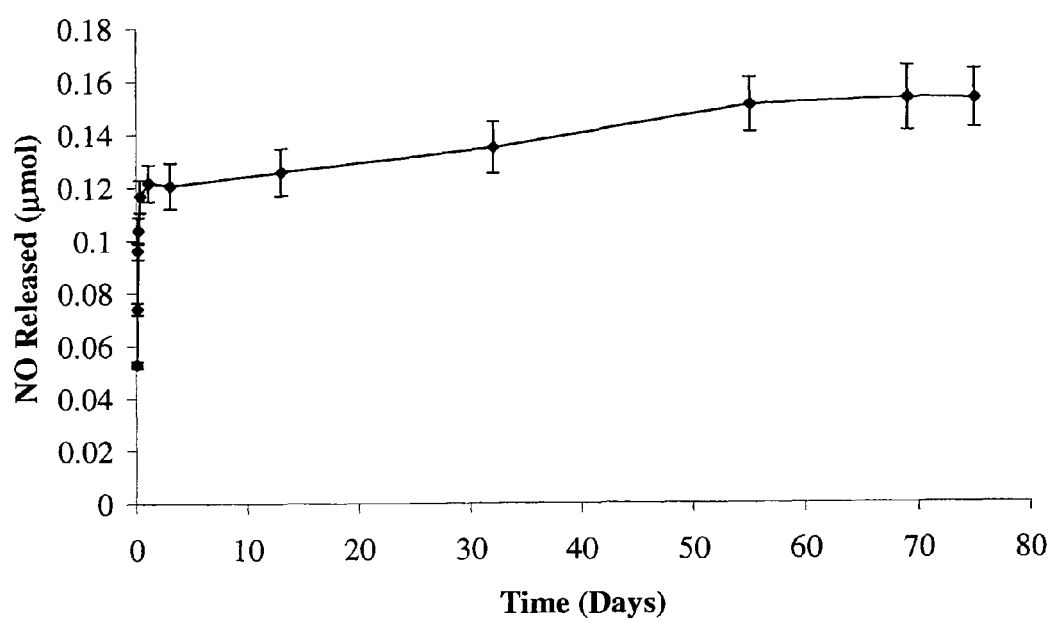
FIG. 22 is a graph showing NO release from a PU-BD-NO film, according to one embodiment.

NO release kinetics from PU-BD-NO films is shown in FIG. 22, occurring over 2 months. Rapid release occurred over the first 48 hours followed by much slower, sustained release for almost 60 days. By way of explanation, and not of limitation, the initial burst of NO release is likely caused by dissociation of diazeniumdiolate complexes on the surface of the films, while the prolonged release after 48 hours is likely caused by the escape of NO embedded in the matrix of the material. No release of NO was detected from PU-BD films reacted with NO gas.

BAEC and SDSMC Proliferation on a PU-BD-NO Peptide-Modified Polyurethane Film.

Figure 23:
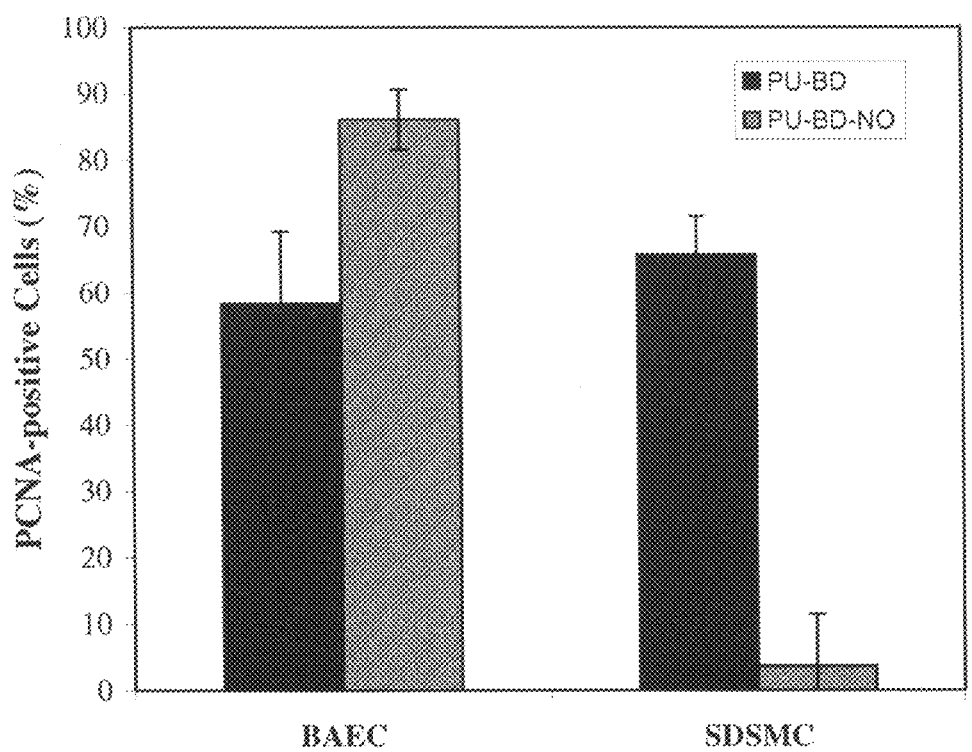
FIG. 23 is a graph comparing BAEC and SDSMC proliferation on films of PU-BD-NO. (burst phase) and PU-BD, according to one embodiment.
Figure 24A:
FIG. 24(a) is a photomicrograph of BAEC cells immunohistochemically stained for PCNA (proliferating cells appear red and nonproliferating cells appear blue) on a PU-BD film, according to one embodiment.
Figure 24B:
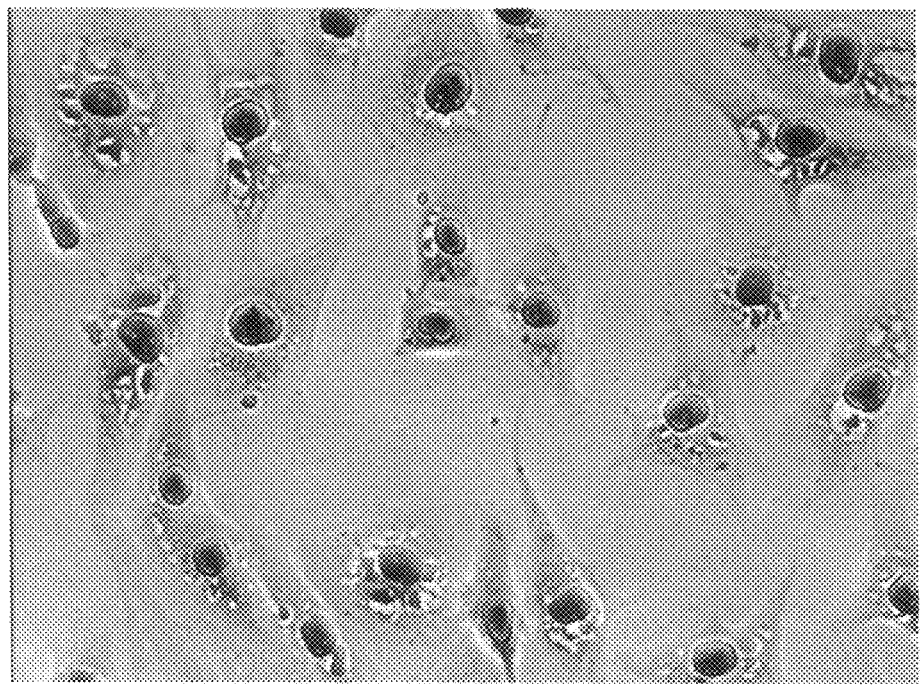
FIG. 24(b) is a photomicrograph of BAEC cells immunohistochemically stained for PCNA (proliferating cells appear red and nonproliferating cells appear blue) on a PU-BD-NO (burst phase) film, according to one embodiment.
Figure 24C:
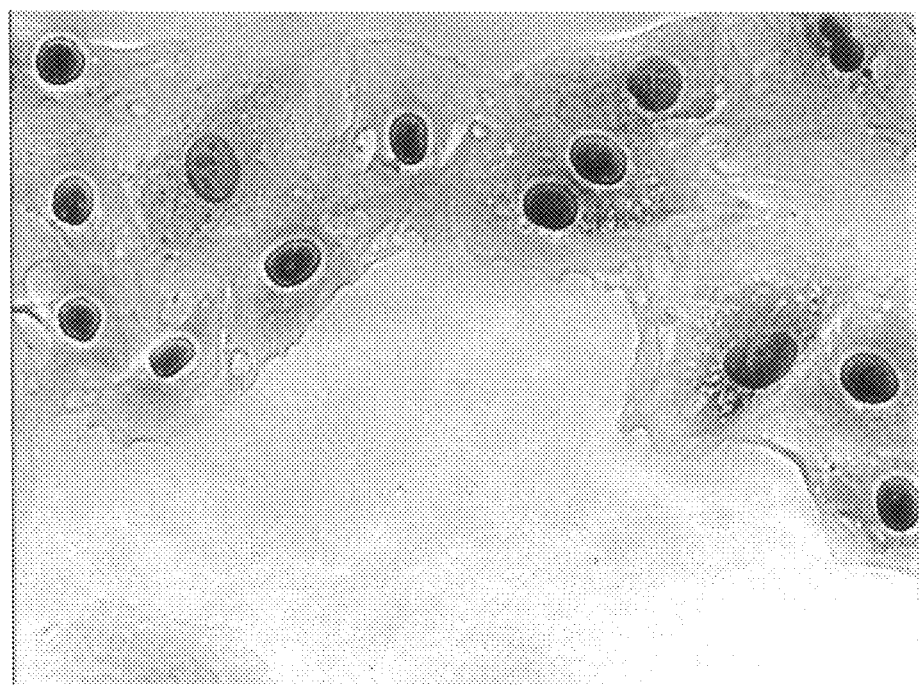
FIG. 24(c) is a photomicrograph of SDSMC cells immunohistochemically stained for PCNA (proliferating cells appear red and nonproliferating cells appear blue) on a PU-BD film, according to one embodiment.
Figure 24D:
FIG. 24(d) is a photomicrograph of SDSMC cells immunohistochemically stained for PCNA (proliferating cells appear red and nonproliferating cells appear blue) on a PU-BD-NO (burst phase) film, according to one embodiment.
Figure 25:
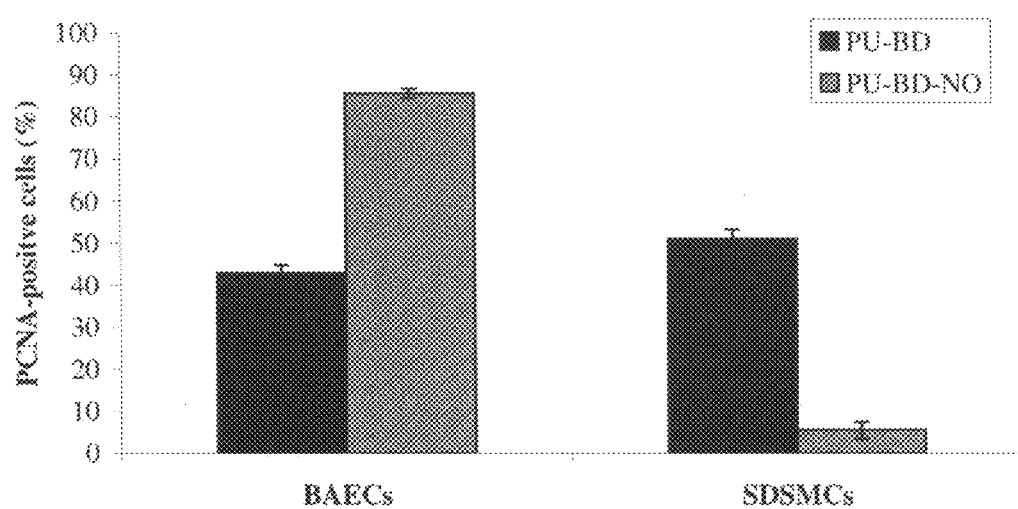
FIG. 25 is a graph comparing BAEC and SDSMC proliferation on PU-BD-NO (slow phase) and PU-BD, according to one embodiment.
Figure 26A:
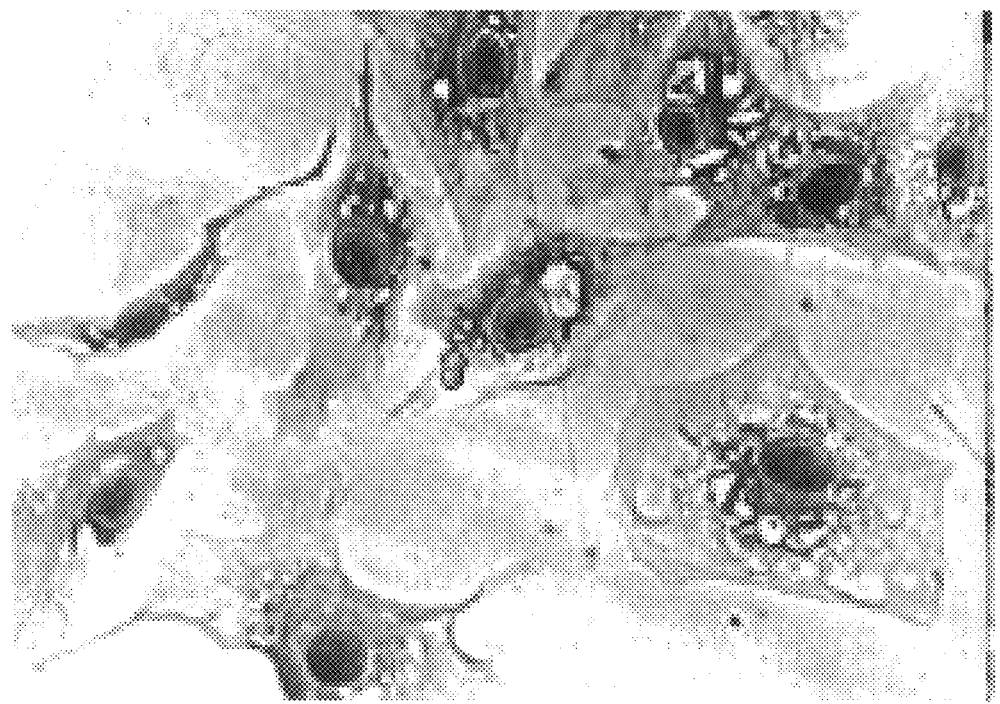
FIG. 26(a) is a photomicrograph of BAEC cells immunohistochemically stained for PCNA (proliferating cells appear red and nonproliferating cells appear blue) on a PU-BD film, according to one embodiment.
Figure 26B:
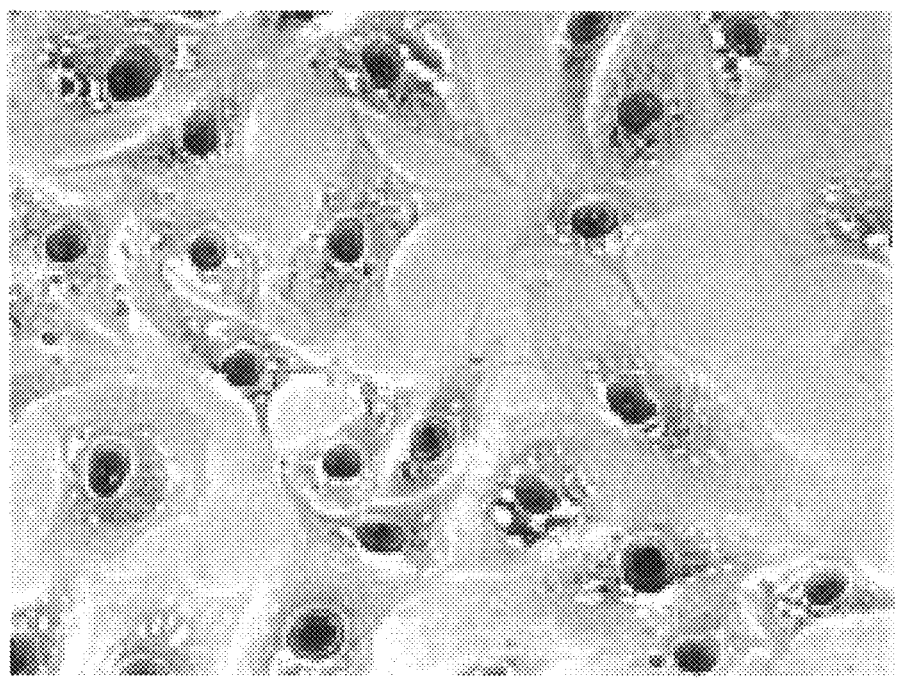
FIG. 26(b) is a photomicrograph of BAEC cells immunohistochemically stained for PCNA (proliferating cells appear red and nonproliferating cells appear blue) on a PU-BD-NO (slow phase) film, according to one embodiment.
Figure 26C:
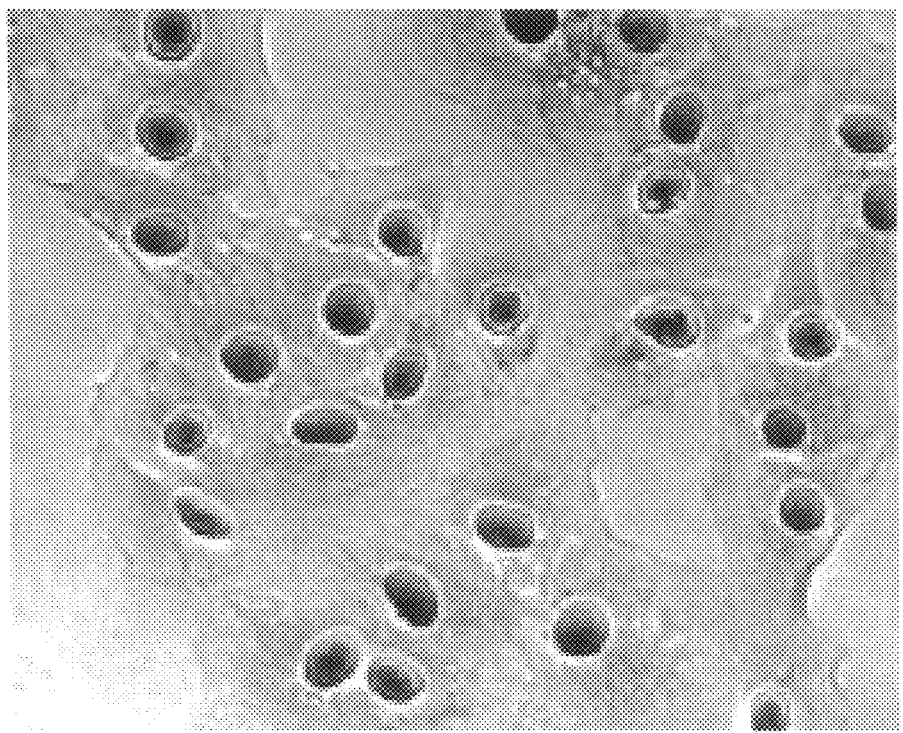
FIG. 26(c) is a photomicrograph of SDSMC cells immunohistochemically stained for PCNA (proliferating cells appear red and nonproliferating cells appear blue) on a PU-BD film, according to one embodiment.
Figure 26D:
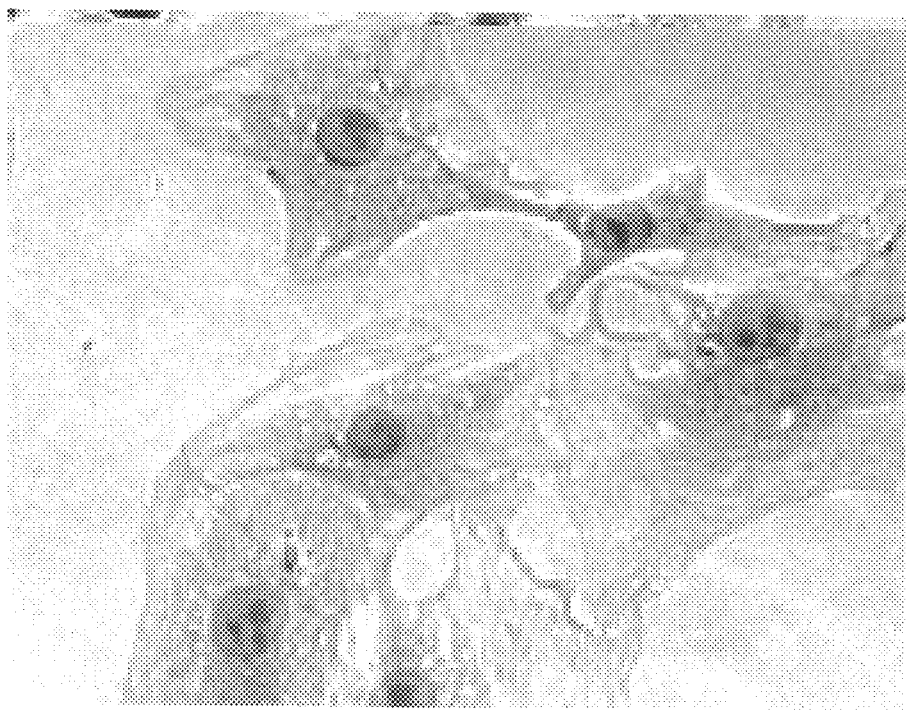
FIG. 26(d) is a photomicrograph of SDSMC cells immunohistochemically stained for PCNA (proliferating cells appear red and nonproliferating cells appear blue) on a PU-BD-NO (slow phase) film, according to one embodiment.
Figure 27:
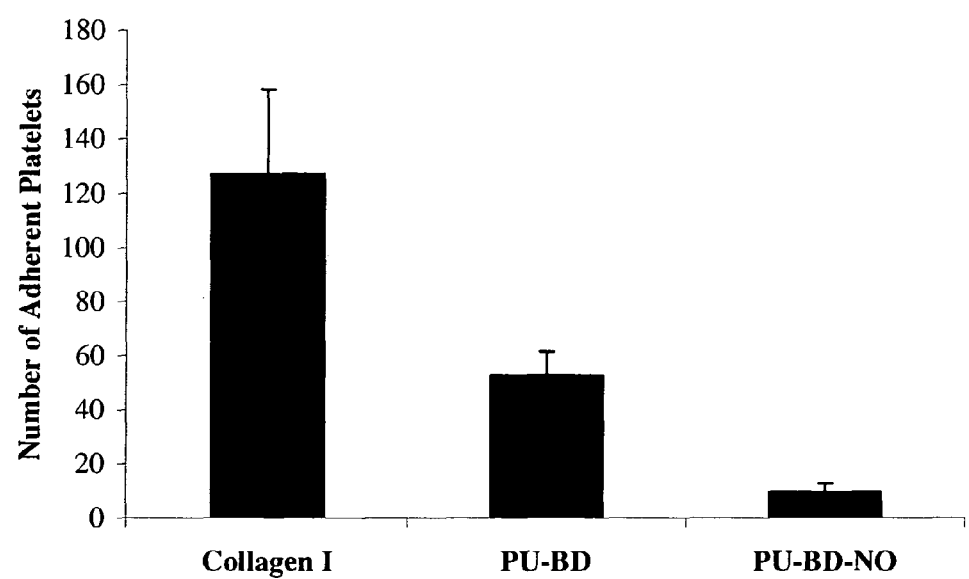
FIG. 27 is a graph comparing platelet adhesion on films of PU-BD, PU-BD-NO (burst phase), and collagen I, according to one embodiment.
Figure 28A:
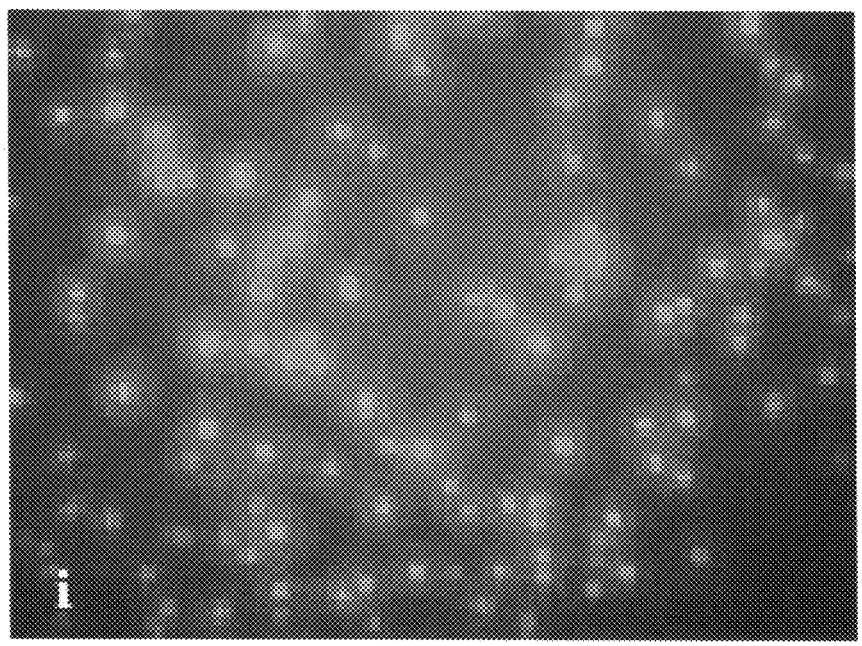
FIG. 28(a) is a photomicrograph of mepacrine-labeled platelets adhering to collagen I, according to one embodiment.
Figure 28B:
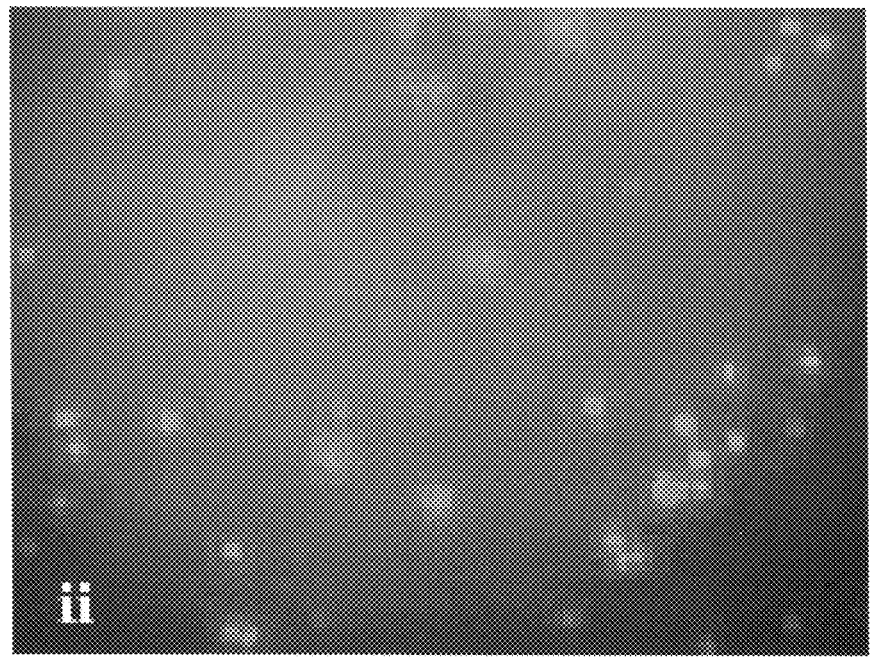
FIG. 28(b) is a photomicrograph of mepacrine-labeled platelets adhering to a PU-BD film, according to one embodiment.
Figure 28C:
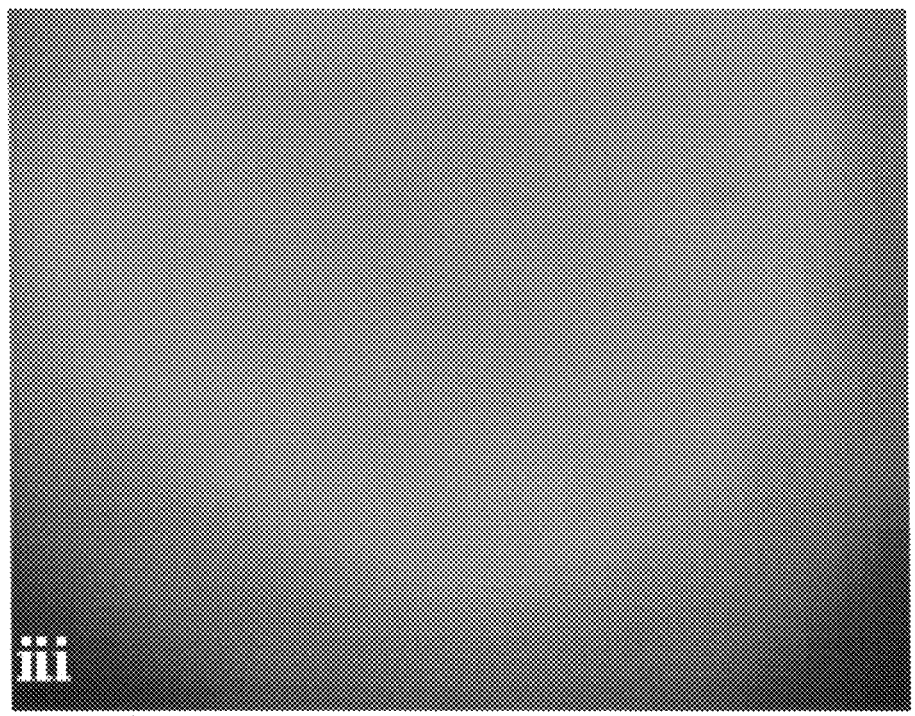
FIG. 28(c) is a photomicrograph of mepacrine-labeled platelets adhering to a PU-BD-NO film (burst phase), according to one embodiment.
Figure 29:
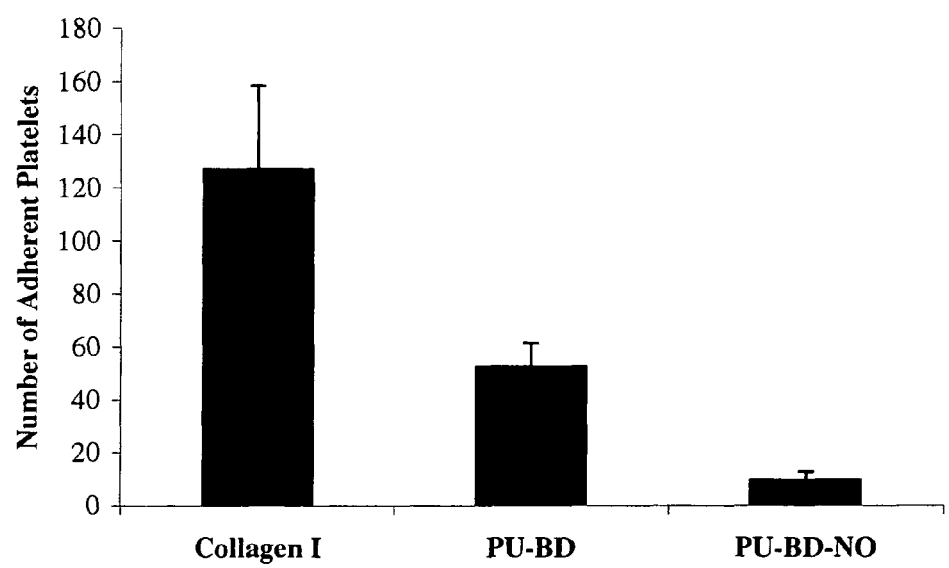
FIG. 29 is a graph comparing platelet adhesion on films of PU-BD, PU-BD-NO (slow phase), and collagen I, according to one embodiment.
Figure 30A:
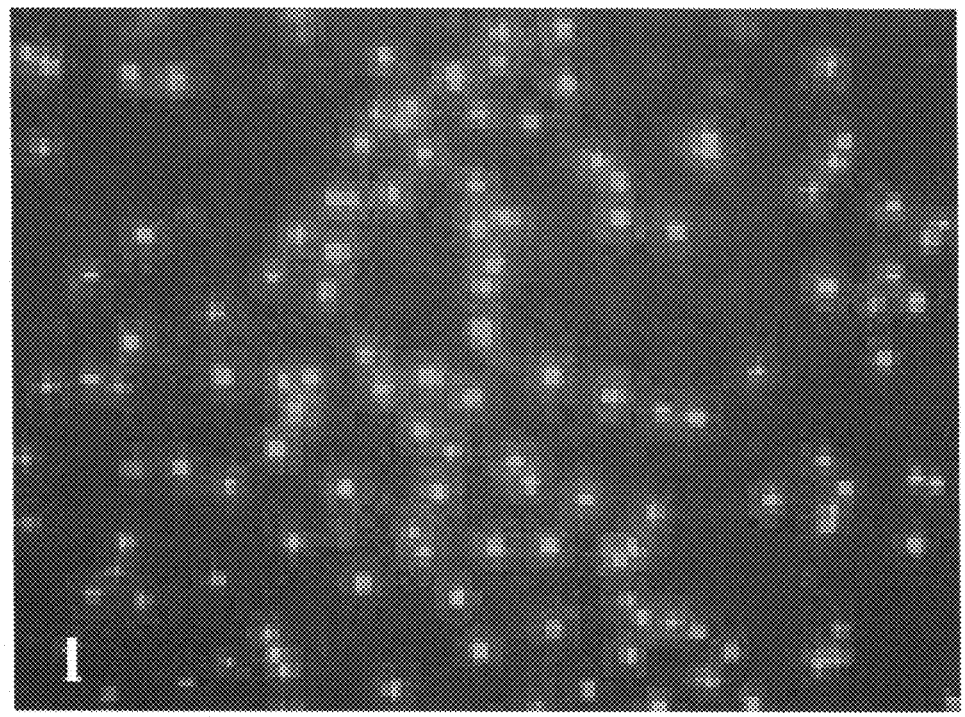
FIG. 30(a) is a photomicrograph of mepacrine-labeled platelets adhering to collagen I, according to one embodiment.
Figure 30B:
FIG. 30(b) is a photomicrograph of mepacrine-labeled platelets adhering to a PU-BD film, according to one embodiment.
Figure 30C:
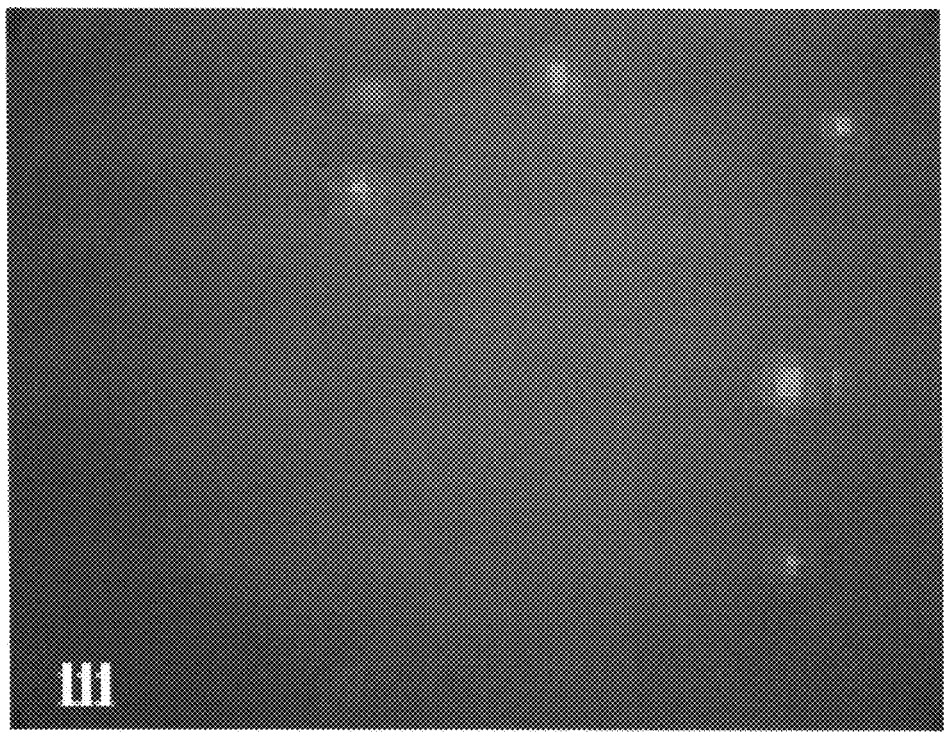
FIG. 30(c) is a photomicrograph of mepacrine-labeled platelets adhering to a PU-BD-NO film (slow phase), according to one embodiment.
Figure 31A:
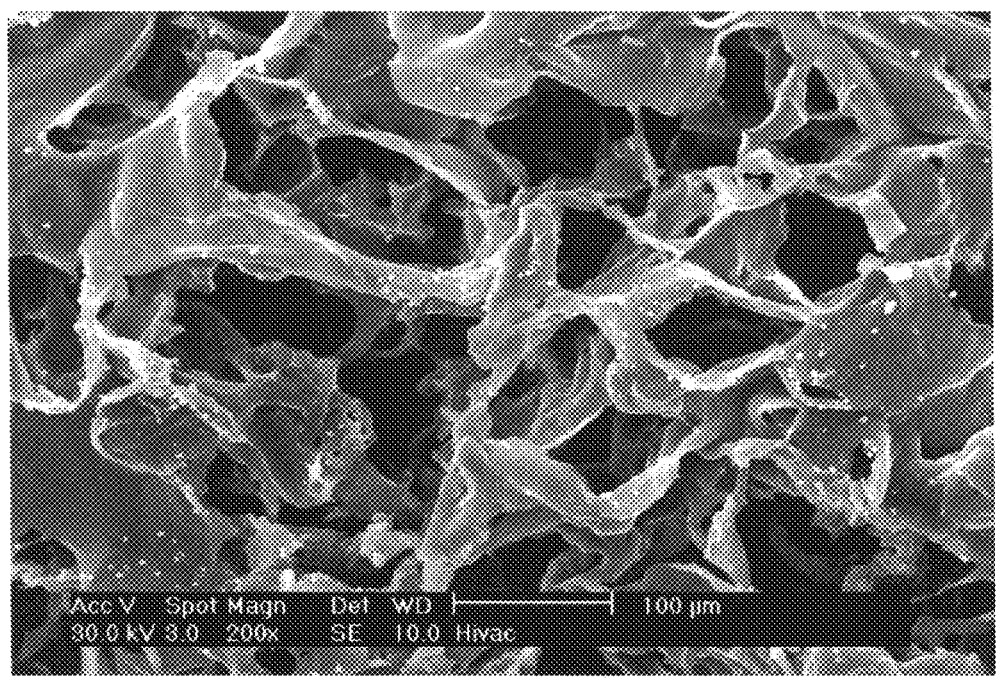
FIG. 31(a) is a surface SEM photomicrograph of the scaffold matrix from a PUU-PPD-PEG microporous scaffold, according to one embodiment.
Figure 31B:
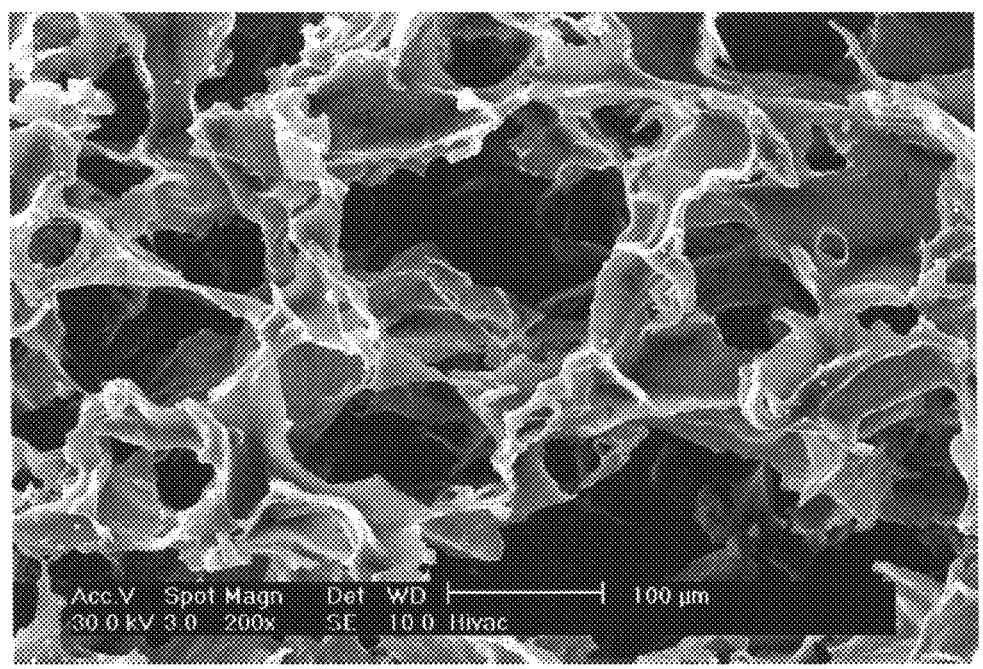
FIG. 31(b) is a cross sectional SEM photomicrograph of the scaffold matrix from a PUU-PPD-PEG microporous scaffold, according to one embodiment.
Figure 31C:
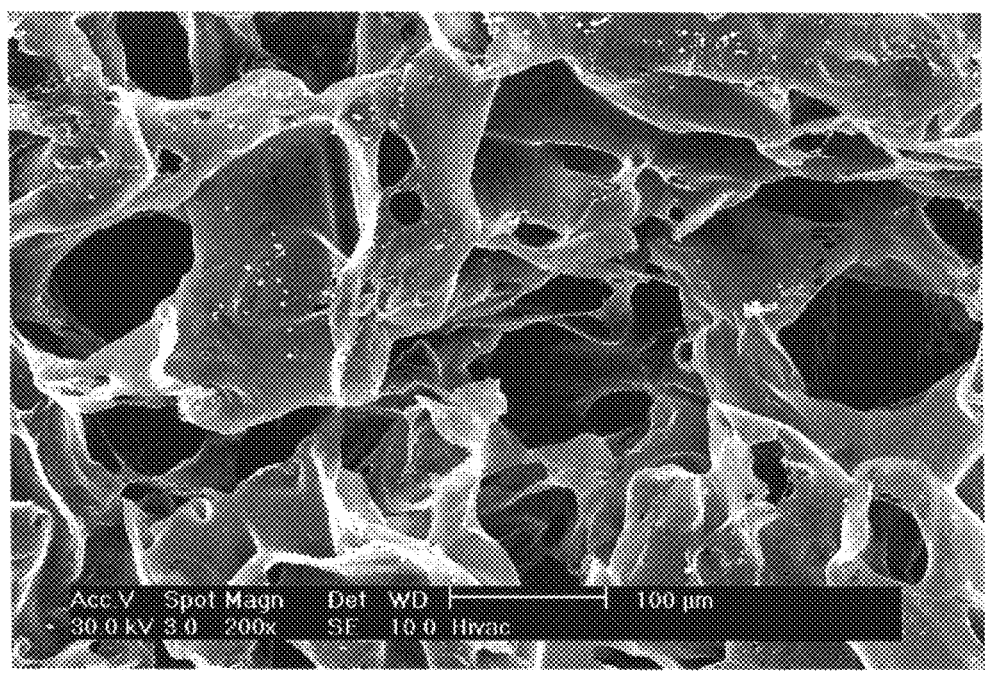
FIG. 31(c) is a surface SEM photomicrograph of the scaffold matrix from a PUU-PEG-YIGSR microporous scaffold, according to one embodiment.
Figure 31D:
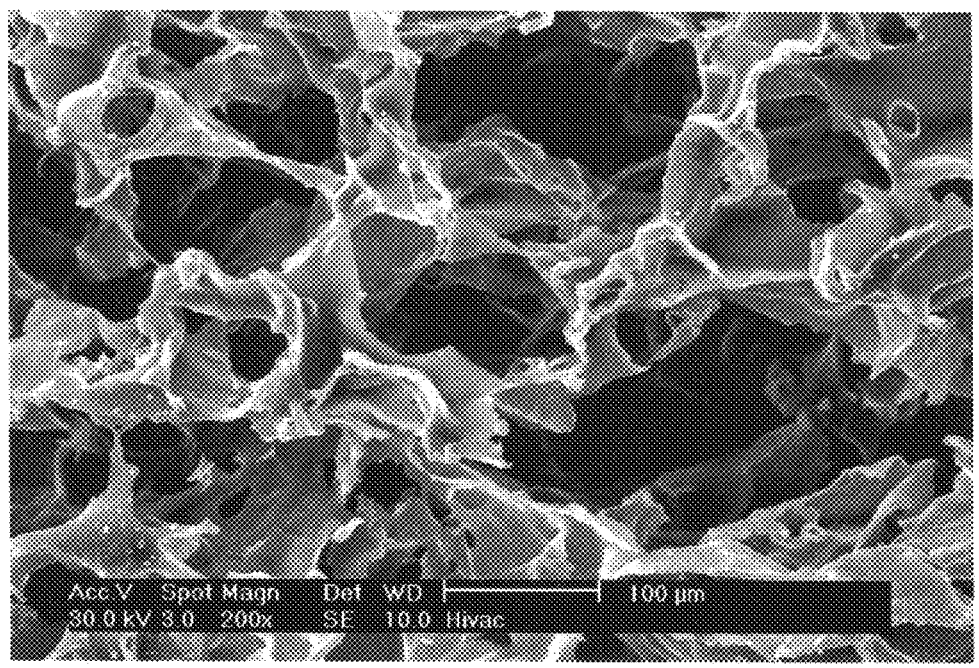
FIG. 31(d) is a cross sectional SEM photomicrograph of the scaffold matrix from a PUU-PEG-YIGSR microporous scaffold, according to one embodiment.

The effect of NO release on BAEC and SDSMC proliferation was examined using immunohistochemical staining for PCNA. The percentage of PCNA-positive BAECs exposed to PU-BD-NO films releasing NO in a rapid burst was significantly greater than those exposed to PU-BD after 48 hours of culture. However, the percent of PCNA-positive SDSMCs cultured with fast-releasing PU-BD-NO films was significantly lower than those cultured with PU-BD films (FIG. 23).

To determine the efficacy of our materials in the slower phase of NO release, PU-BD-NO and PU-BD films were incubated in HBS for 48 hours, and then both BAECs and SDSMCs were exposed to these films as previously described. Again, the percentage of PCNA-positive BAECs cultured with NO-releasing PU-BD films was higher than that of BAECs exposed to control PU-BD films, and the number of positively stained SDSMCs cultured with PU-BD-NO films was drastically lower than SDSMCs in the presence of PU-BD films (FIG. 23).

Platelet Adhesion to a PU-BD-NO Peptide-Modified Polyurethane Film.

Platelet adhesion to PU-BD and PU-BD-NO was examined using mepacrine-labeled whole blood. Platelet adhesion to PU-BD was approximately 40% less than on the positive control, collagen I (FIG. 24). Platelet adhesion on PU-BD-NO was lower, with almost no adherent platelets observed.

To ascertain if these materials would retain their thromboresistance during the slower stages of NO release, films were allowed to release in HBS for 48 hours before they were exposed to whole blood as described above. Once more, there was a 40% reduction in the number of platelets adhering to PU-BD when compared to collagen I (FIG. 24). Platelet adhesion to PUDB was again significantly lower.

NO Release Kinetics of a PU-BD-PEG-YIGSR-NO Peptide-Modified Polyurethane Film.

Figure 35:
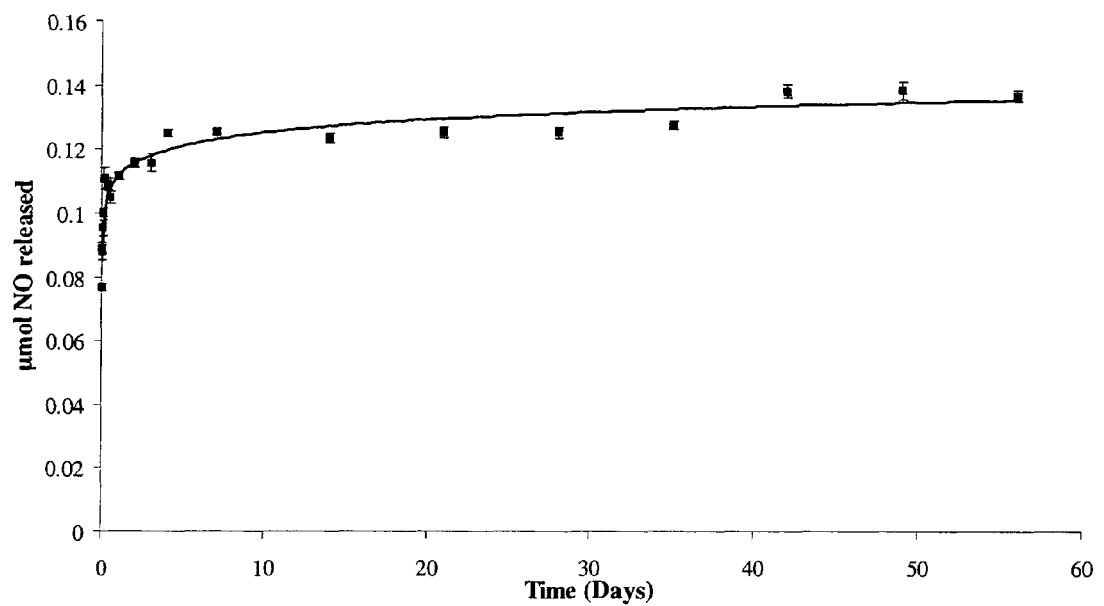
FIG. 35 is a graph showing NO release from a PU-BD-PEG-YIGSR-NO film, according to one embodiment.

NO release kinetics from PU-BD-PEG-YIGSR-NO films is shown in FIG. 35, occurring over 2 months. Rapid release occurred over the first 48 hours followed by much slower, sustained release for almost 60 days. By way of explanation, and not of limitation, the initial burst of NO release is likely caused by dissociation of diazeniumdiolate complexes on the surface of the films, while the prolonged release after 48 hours is likely caused by the escape of NO embedded in the matrix of the material. No release of NO was detected from PU-BD-PEG-YIGSR films reacted with NO gas.

BAEC and SDSMC Adhesion and Proliferation on a PU-BD-PEG-YIGSR-NO Peptide-Modified Polyurethane Film.

Figure 36:
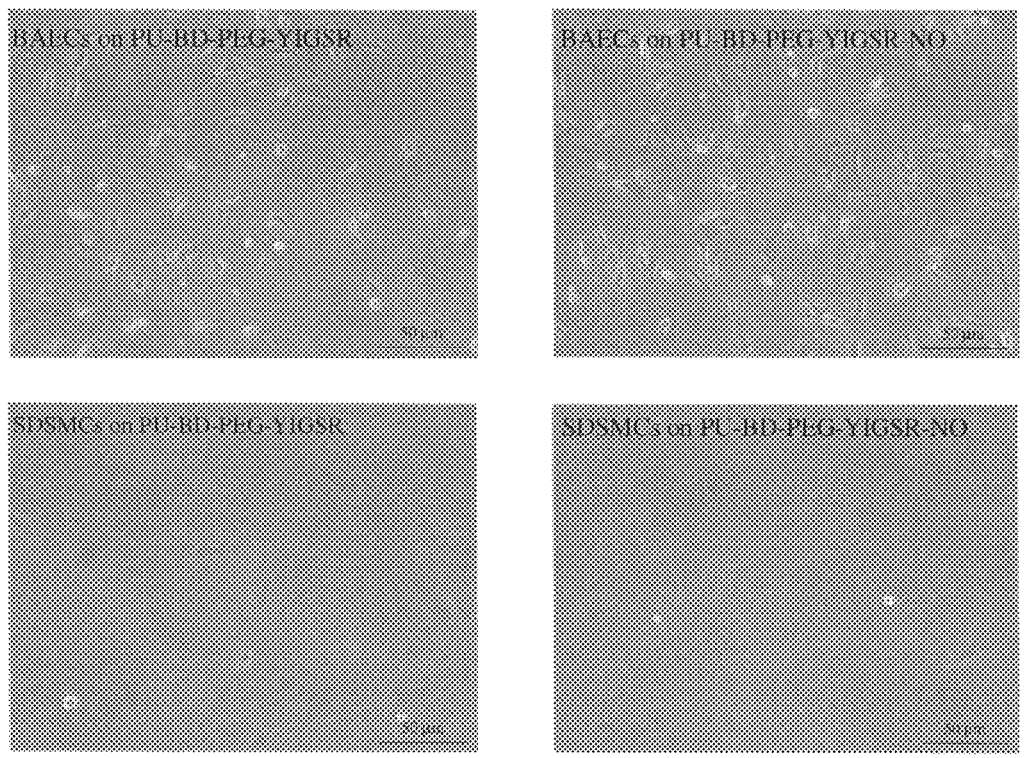
FIG. 36 are photomicrographs showing adhesion of BAECs and SDSMCs on films of PU-BD-PEG-YIGSR and PU-BD-PEG-YIGSR-NO, according to one embodiment.

The effects of adhesive peptides and NO on BAEC and SDSMC attachment were evaluated. The number of adherent BAECs was greater than adherent SDSMCs on both PU-BD-PEG-YIGSR-NO and PU-BD-PEG-YIGSR as shown in FIG. 36.

Figure 37:
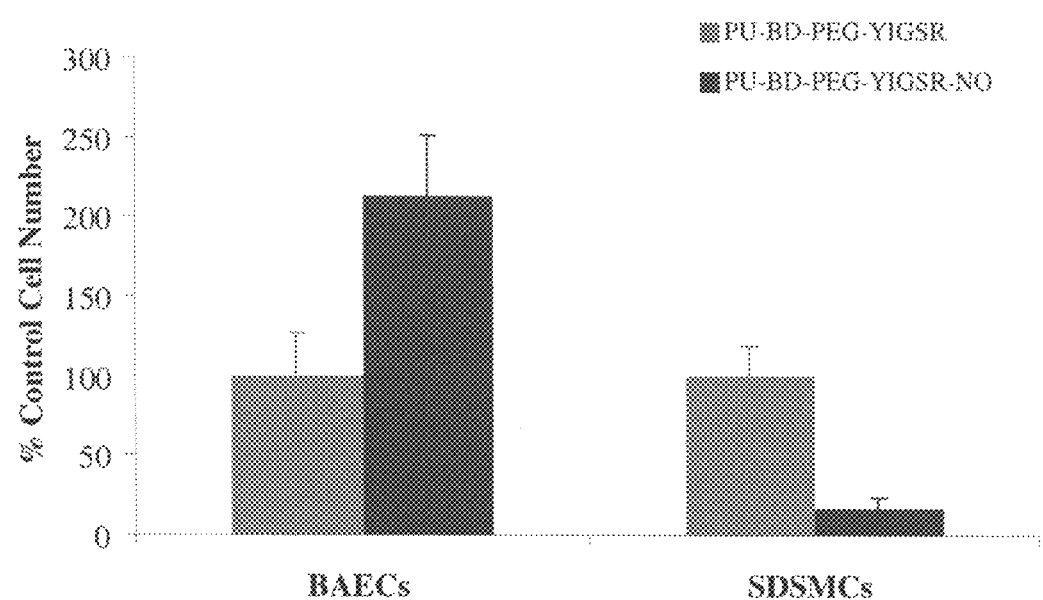
FIG. 37 is a graph comparing BAECs and SDSMCs proliferation on PU-BD-PEG-YIGSR and PU-BD-PEG-YIGSR-NO, according to one embodiment.

The effects of adhesive peptides and NO on BAEC and SDSMC prolfieration were evaluated. As shown in FIG. 37, the PU-BD-PEG-YIGSR-NO films stimulated growth of BAECs, but inhibited growth of SDSMCs.

Platelet Adhesion to a PU-BD-PEG-YIGSR-NO Peptide-Modified Polyurethane Film.

Figure 38:
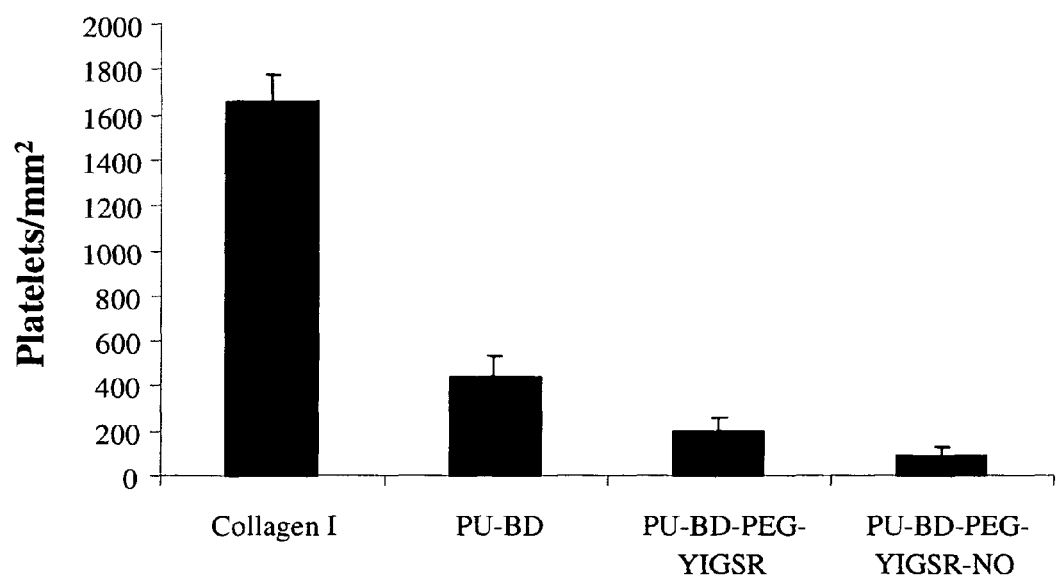
FIG. 38 is a graph comparing platelet adhesion on PU-BD, PU-BD-PEG-YIGSR, PU-BD-PEG-YIGSR-NO, and collagen I, according to one embodiment.

Platelet adhesion to PU-BD, PU-BD-PEG-YIGSR, and PU-BD-PEG-YIGSR-NO was examined using mepacrine-labeled whole blood. Platelet adhesion to PU-BD was approximately 40% less than on the positive control, collagen I (FIG. 38). Platelet adhesion was even lower on PU-BD-PEG-YIGSR, and lowest on PU-BD-PEG-YIGSR-NO, as shown in FIG. 38.

Synthesis and Characterization of a PUU-YIGSR-LGPA Peptide-Modified Polyurethane.

The NMR spectra were obtained and characterized as described above. The characteristic proton peaks of tyrosine (6.5-7.0 ppm) from the GGGYIGSRGGGK sequence were assigned, indicating the successful incorporation of the peptide sequence into the PUU-YIGSR polymer. The peaks of prepolymer, PUU-PPD, and PUU-YIGSR-LGPA were also assigned and characterized.

Proteolytic Degradation of a PUU-YIGSR-LGPA Peptide-Modified Polyurethane Film.

Figure 15:
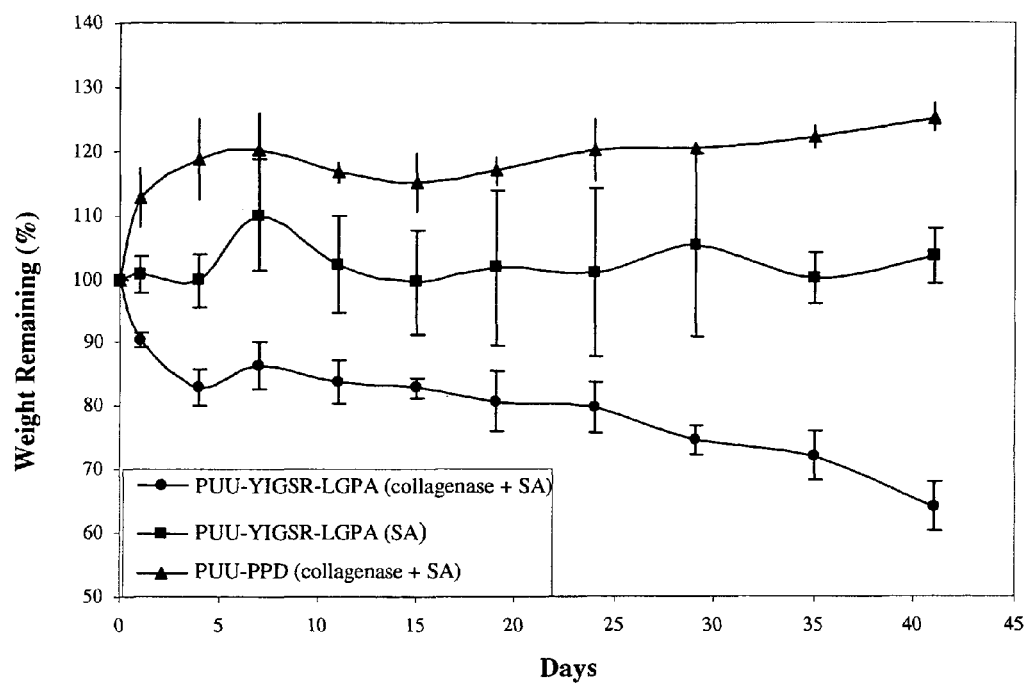
FIG. 15 is a graph showing the proteolytic degradation of PUU-YIGSR-LGPA and PUU-PPD by collagenase, collagenase and SA, and SA alone, according to one embodiment.

FIG. 15 shows the results of proteolytic degradation of PUU-YIGSR-LGPA by collagenase. PUU-YIGSR-LGPA with collagenase was degraded with incubation time and lost 35% of weight after 40 days. However, PUU-YIGSR-LGPA without collagenase and PUU-PPD with collagenase were not degraded. This result indicated that LGPA was successfully incorporate into the main chain and cleaved by collagenase, causing weight loss.

Adhesion and Spreading of BAECs on a PUU-YIGSR-LGPA Peptide-Modified Polyurethane Film.

Figure 16A:
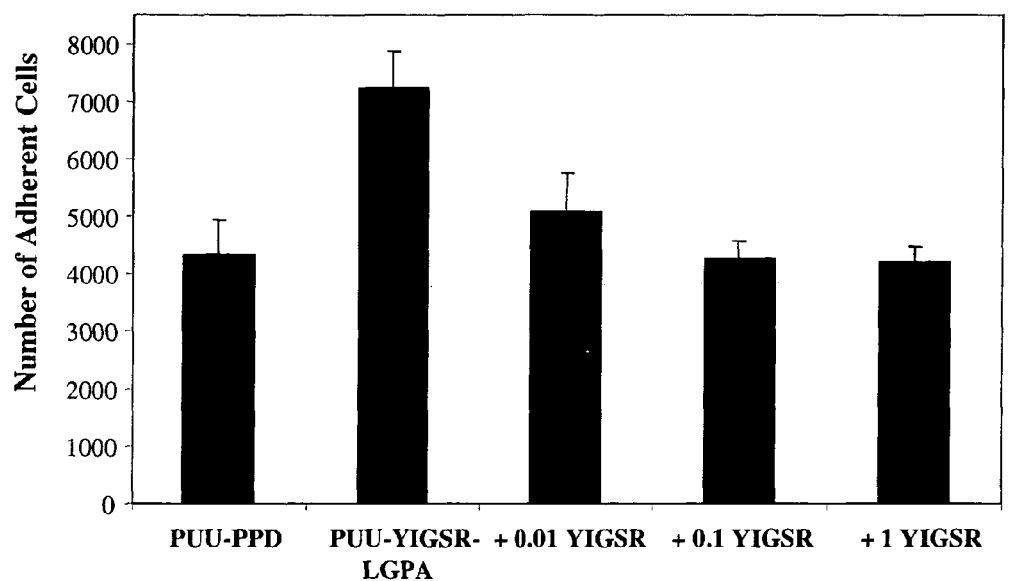
FIG. 16(a) is a graph comparing the competitive inhibition of attachment and spreading of BAECs by soluble YIGSR at three different concentrations (0.01, 0.1, and 1 mM) compared to PUU-PPD and PUU-YIGSR-LGPA as measured by adherent cells, according to one embodiment
Figure 16B:
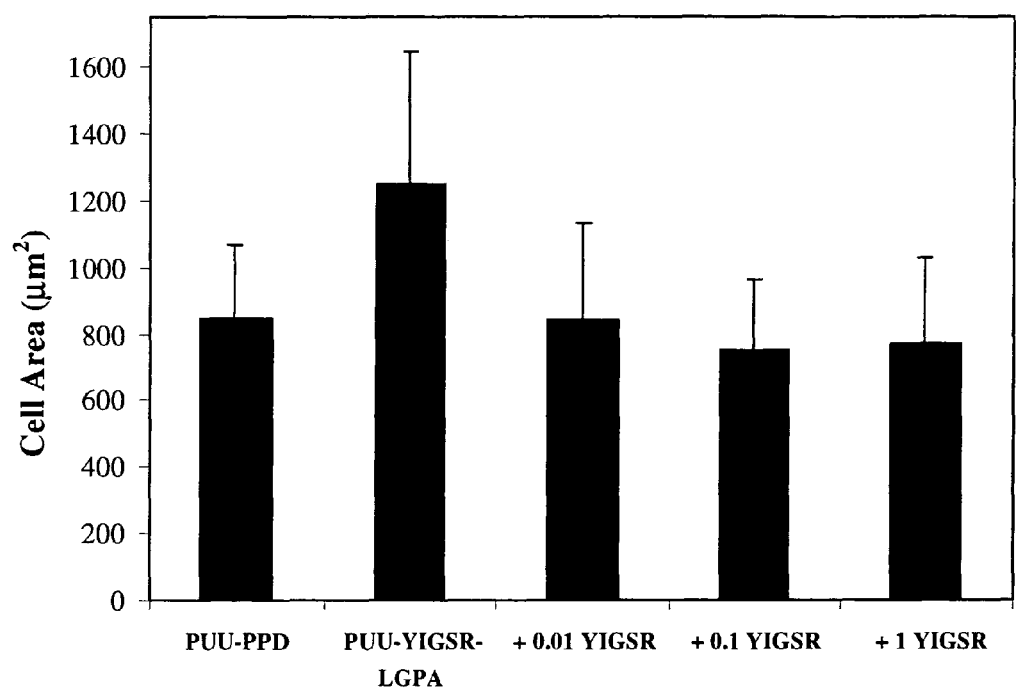
FIG. 16(b) is a graph comparing the competitive inhibition of attachment and spreading of BAECs by soluble YIGSR at three different concentrations (0.01, 0.1, and 1 mM) compared to PUU-PPD and PUU-YIGSR-LGPA as measured by cell surface area, according to one embodiment.
Figure 16C:
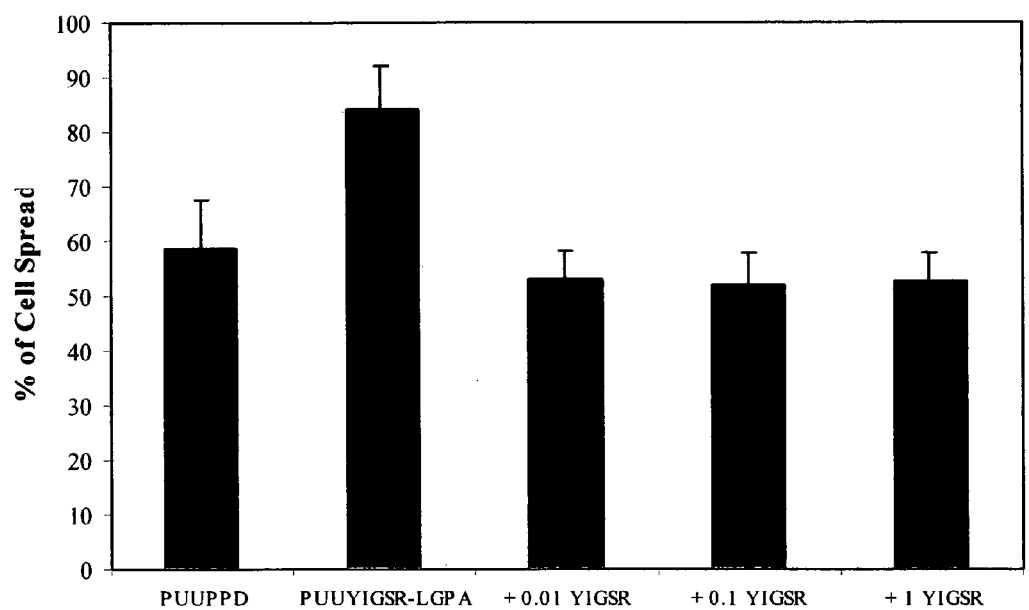
FIG. 16(c) is a graph comparing the competitive inhibition of attachment and spreading of BAECs by soluble YIGSR at three different concentrations (0.01, 0.1, and 1 mM) compared to PUU-PPD and PUU-YIGSR-LGPA as measured by the percent of cells that were spread, according to one embodiment.

An analysis was performed to determine whether the incorporation of adhesive peptides into a polyurethane impacted BAEC attachment and spreading. The number of adherent cells on PUU-YIGSR-LGPA was significantly greater than on PUU-PPD ($p<0.05$) as shown in FIG. 16(a). However, adhesion of BAECs was reduced in the presence of soluble YIGSR peptides over the entire ranges of the soluble peptide concentrations (0.01, 0.1, and 1 mM). Similar results were also observed in cell surface area and percent of cell spreading in FIG. 16(b)-(c). These results suggest that adhesion of BAECs to this peptide-modified material is mediated predominantly by specific receptor-ligand interactions.

Migration of BAECs on a PUU-YIGSR-LGPA Peptide-Modified Polyurethane Film.

Figure 17A:
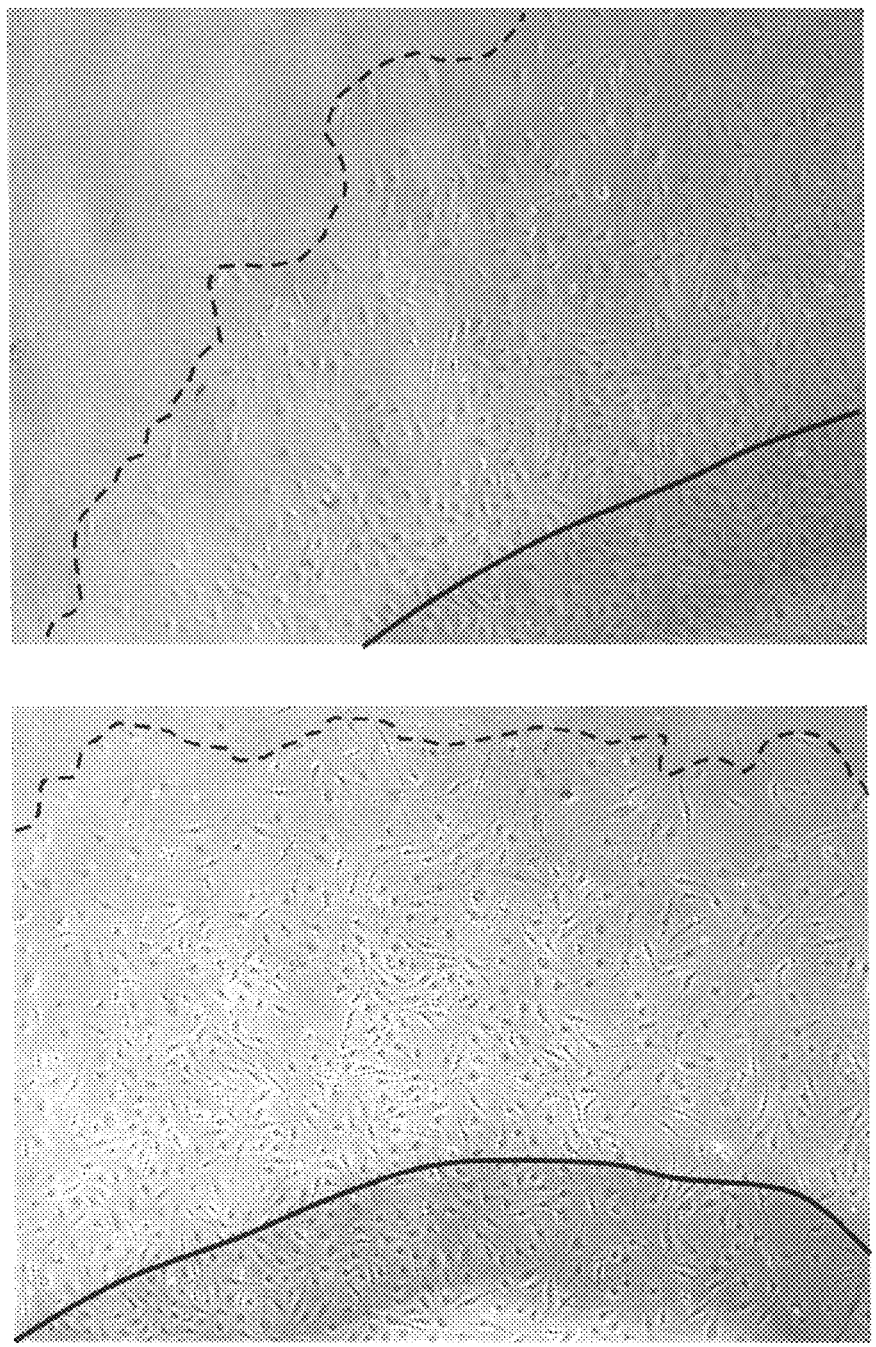
FIG. 17(a) is a photomicrograph showing the migration of BAECs on PUU-YIGSR-LGPA after 48 hours, according to one embodiment.
Figure 17B:
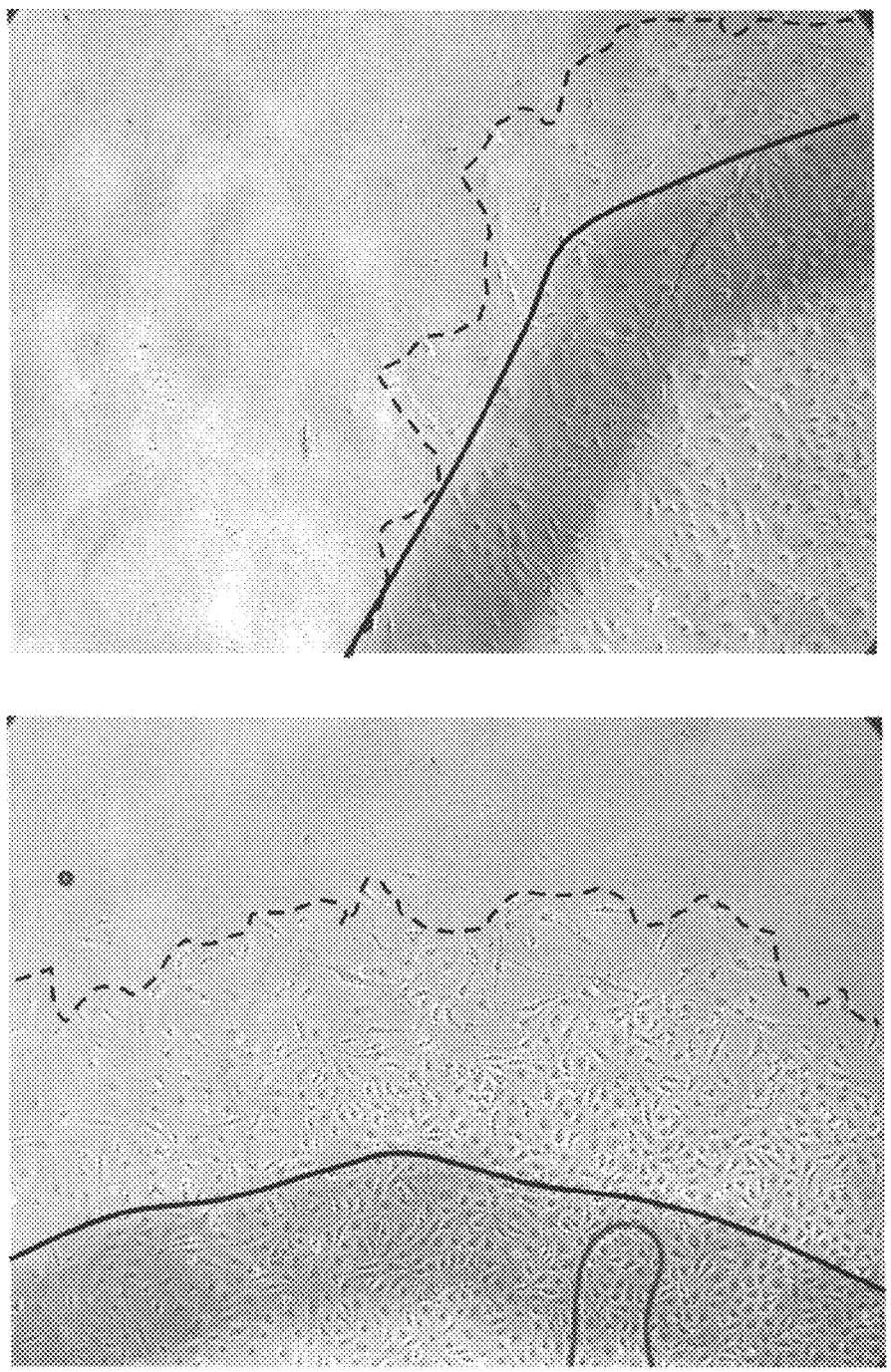
FIG. 17(b) is a photomicrograph showing the migration of BAECs on PUU-PPD after 48 hours, according to one embodiment.

As shown in FIG. 17(a)-(b), significantly greater cell migration beyond original boundary was found on PUU-YIGSR-LGPA surface compared to PUU-PPD after 48 hours of incubation.

Characterization of a PUU-PEG-YIGSR Peptide-Modified Polyurethane Microporous Scaffold.

PUU-PEG and PUU-PEG-YIGSR scaffolds were successfully fabricated using gas foaming and salt leaching. The porosity of the scaffolds was characterized using mercury intrusion porosimetry and SEM. Both PUU-PEG and PUU- PEG-YIGSR scaffolds showed highly interconnected pore structures through the matrices with porosities of approximately 78% (PUU-PEG: 78%±3.6 and PUU-PEG-YIGSR: 77%±8.4) and pore sizes of 20-200 μm. The pores were highly open on both surface and cross section of the scaffolds, as shown in FIG. 31(a)-(d).

Uniaxial mechanical testing was performed to determine mechanical properties of the scaffolds as shown in Table 1. The PUU-PEG-YIGSR scaffolds showed greater tensile strength and elongation at failure compared to PUU-PEG (tensile strength: 1.4 MPa±0.03 vs. 0.19 MPa±0.01, p<0.01 and elongation: 796 MPa±122 vs. 129 MPa±2.08, p<0.02). There was no significant difference in elastic modulus (PUU-PEG-YIGSR: 0.33 MPa±0.1 and PUU-PEG: 0.21 MPa±0.01).

TABLE 1

Summary of Mechanical Properties, Migration, DNA, and Hydroxyproline Production in PUU-PEG and PUU-PEG-YIGSR Scaffold Matrices.

|  | PUU-PEG | PYU-PEG-YIGSR |
| --- | --- | --- |
| Tensile strength (MPa) | 0.19 ± 0.01 | 1.4 ± 0.03 |
| Elongation at failure (%) | 129 ± 2.08 | 796 ± 122 |
| Number of cells migrated through the scaffolds | 1026.7 ± 266.3 | 4266.7 ± 482.2 |
| DNA (ng)/scaffold | 1.84 ± 0.26 | 4.41 ± 0.34 |
| Hydroxyproline production (ng)/(ng) DNA | 0.069 ± 0.062 | 1.092 ± 0.323 |

Cells Cultured on a PUU-PEG-YIGSR Peptide-Modified Polyurethane Microporous Scaffold.

Figure 32A:
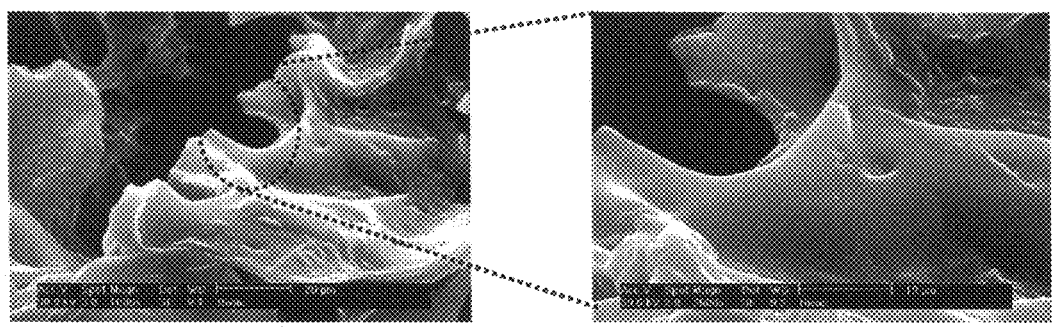
FIG. 32(a) is a SEM photomicrograph of BAECs cultured for 3 days in a PUU-PPD-PEG microporous scaffold matrix, according to one embodiment.
Figure 32B:
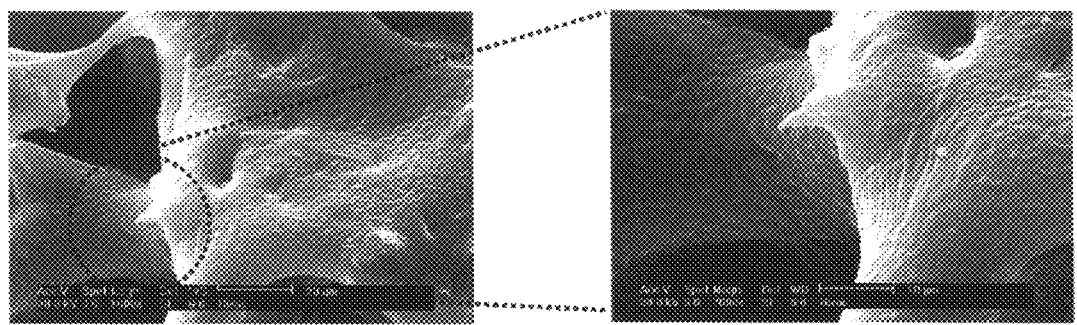
FIG. 32(b) is a SEM photomicrograph of BAECs cultured for 3 days in a PUU-PEG-YIGSR microporous scaffold matrix, according to one embodiment.
Figure 33A:
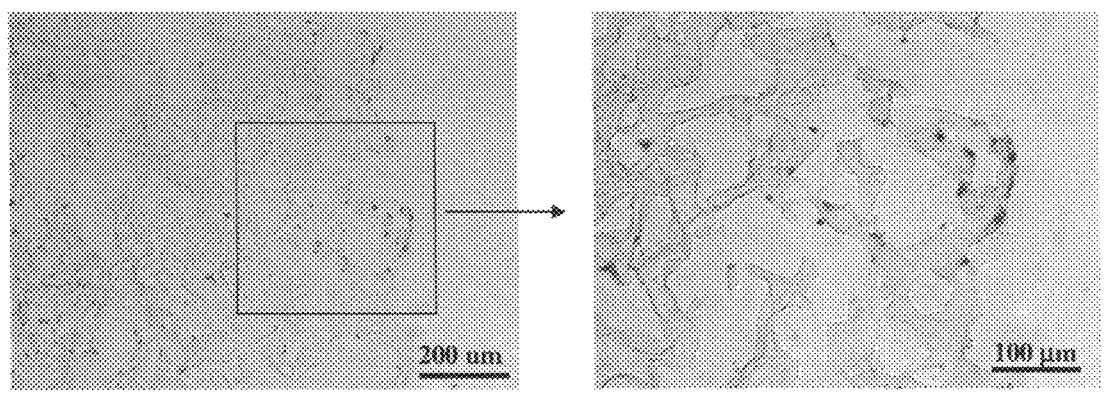
FIG. 33(a) is a cross sectional photomicrograph of a histological analysis of hematoxylin stained BAECs culture for 3 days on PUU-PPD-PEG, according to one embodiment.
Figure 33B:
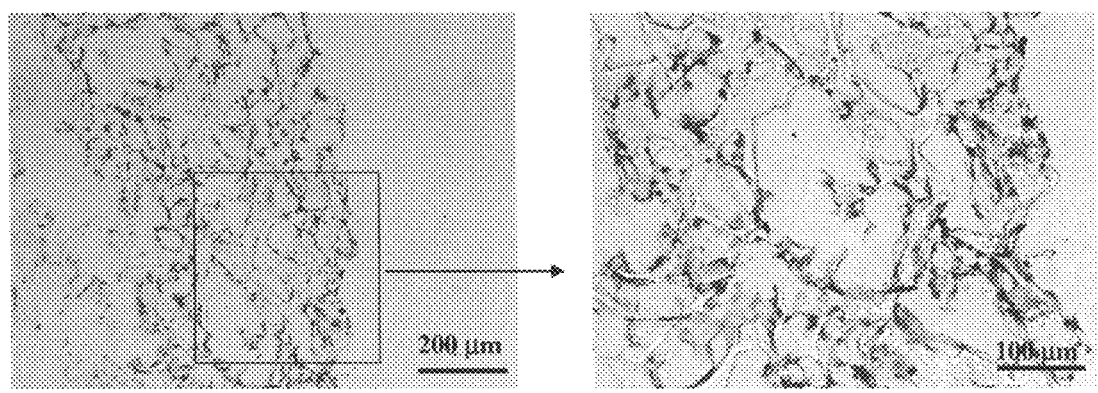
FIG. 33(b) is a cross sectional photomicrograph of a histological analysis of hematoxylin stained BAECs culture for 3 days on PUU-PEG-YIGSR, according to one embodiment.

Endothelial cells were seeded on the top and bottom of the scaffolds and cultured for three days. Cell attachment and morphology in the scaffolds were visualized using SEM as shown in FIG. 32(a)-(b). On the PUU-PEG scaffolds, few cells were found to adhere through the scaffolds. Individual cells were distributed randomly on the scaffolds, and cell colonies were not found (FIG. 32(a)). However, confluent endothelial cell attachment and spreading were found throughout the PUU-PEG-YIGSR scaffold matrix (FIG. 32(b)). Endothelial cells created monolayers along the interconnected pore network in the scaffold. This was also consistent with the histological analysis shown in FIG. 33(a)-(b).

Migration of Cells Through a PUU-PEG-YIGSR Peptide-Modified Polyurethane Microporous Scaffold.

To study the interconnectivity of the scaffold matrix and bioactivity of the peptide sequences on the polymer matrix, the migration of the cells through the scaffolds were studied. Cells were seeded on the top of the scaffolds, and cell-seeded scaffolds were maintained in tissue culture plates for 90 minute to ensure cell attachment on the scaffolds, then placed into the transwell insert. After 7 days of culture, scaffolds were removed. Then each insert well was transferred to another companion plate, and cells on the top and bottom of the membrane were counted. No cells were observed on the bottom of companion plates. As shown in Table 1, the number of cells that had migrated through the PUU-PEG-YIGSR matrices (4266.7±482.2) was significantly greater than for PUU-PEG (1026.7±266.3, p<0.005).

DNA and Hydroxyproline Measurements from a PUU-PEG-YIGSR Peptide-Modified Polyurethane Microporous Scaffold.

The effect of bioactive peptide sequence on endothelial cell proliferation and extracellular matrix production in the scaffolds were studied as shown in Table 1. DNA concentration in PUU-PEG-YIGSR matrices (4.41±0.34 ng/scaffold) was significantly greater than that in PUU-PEG (1.84±0.26 ng/scaffold, p<0.001). Hydroxyproline production, a marker for collagen synthesis, in PUU-PEG-YIGSR matrices (1.092±0.323 ng/ng DNA) was also significantly greater than that in PUU-PEG (0.069±0.062 ng/ng DNA, p<0.05). Higher DNA concentration in PUU-PEG-YIGSR scaffold matrices indicates the greater number of cells, so PUU-PEG-YIGSR scaffold matrices were expected to have higher hydroxyproline production. However, significantly greater hydroxyproline production per cell (ng hydroxyproline/ng DNA) indicates that the bioactive peptide sequences might not only enhance cell adhesion but also facilitate extracellular matrix production.

Therefore, the present invention is well adapted to attain the ends and advantages mentioned as well as those that are inherent therein. While numerous changes may be made by those skilled in the art, such changes are encompassed within the spirit of this invention as defined by the appended claims.

What is claimed is:

1. A peptide-modified polyurethane comprising a reaction product of an isocyanate, a chain extender, and a peptide, wherein the peptide is incorporated into and between units of a backbone chain of the peptide-modified polyurethane.

2. The peptide-modified polyurethane of claim 1 wherein the reaction product comprises an intermediate product.

3. The peptide-modified polyurethane of claim 1 wherein the reaction product comprises an intermediate product that comprises a prepolymer chosen from PUU-PPD, PU-BD, and PUU-PPD-PEG.

4. The peptide-modified polyurethane of claim 1 wherein the reaction product is chosen from PUU-YIGSR, PUU-PEG-YIGSR, PUU-YIGSR-LGPA, PU-BD-NO, PU-BD-PEG-YIGSR, and PU-BD-PEG-YIGSR-NO.

5. The peptide-modified polyurethane of claim 1 wherein the isocyanate comprises at least one isocyanate chosen from toluene diisocyanate; methylene diphenyl diisocyanate; methylene dicyclohexane diisocyanate; naphthalene diisocyanate; hexamethylene diisocyanate; p-phenylene diisocyanate; trans-cyclohexane-1,4-diisocyanate; 1,6-diisocyanatohexane; isophorone diisocyanate; tetramethylxylene diisocyanate; and an isomer thereof.

6. The peptide-modified polyurethane of claim 1 wherein the chain extender comprises at least one chain extender chosen from a polyol, a polyamine, a polysiloxane, and a peptide.

7. The peptide-modified polyurethane of claim 1 wherein the peptide comprises a bioactive peptide.

8. The peptide-modified polyurethane of claim 1 wherein the peptide comprises at least one bioactive peptide chosen from a cell modulating peptide, a chemotactic peptide, an anticoagulant peptide, an antithrombotic peptide, an antitumor peptide, an anti-infectious peptide, a growth potentiating peptide, and an antiinflammatory peptide.

9. The peptide-modified polyurethane of claim 1 wherein the peptide comprises an amino acid sequence chosen from RGDC (SEQ ID. NO:1), RGEC (SEQ ID. NO:2), RGDT (SEQ ID. NO:3), RGDS (SEQ ID. NO:4), LDV (SEQ ID. NO:5), REDV (SEQ ID. NO:6), RGDV (SEQ ID. NO:7), LRGDN (SEQ ID. NO:8), IKVAV (SEQ ID. NO:9), YIGSR (SEQ ID. NO:10), PDSGR (SEQ ID. NO:11), RNIAEIIKDA (SEQ ID. NO:12), RGDT (SEQ ID. NO:13), DGEA (SEQ ID. NO:14), DGEAGC (SEQ ID. NO:15), EPRGDNYR (SEQ ID. NO:16), EILDV (SEQ ID. NO:17), REDV (SEQ ID. NO:18), SIKVAV (SEQ ID. NO:19), RGD (SEQ ID. NO:20), KQAGDV (SEQ ID. NO:21), HRSNRKGV (SEQ ID. NO:22), VTXG (SEQ ID. NO:23), LGPA (SEQ ID. NO:24), and AAAAAAAAA (SEQ ID. NO:25).

10. A peptide-modified polyurethane comprising a reaction product of an isocyanate, a chain extender, and a peptide, wherein the peptide is incorporated into a backbone chain of the peptide-modified polyurethane so as to render the peptide-modified polyurethane degradable under physiological conditions.

11. The peptide-modified polyurethane of claim 10 wherein the reaction product is chosen from PUU-YIGSR, PUU-PEG-YIGSR, PUU-YIGSR-LGPA, PU-BD-NO, PU-BD-PEG-YIGSR, and PU-BD-PEG-YIGSR-NO.

12. The peptide-modified polyurethane of claim 10 wherein the peptide comprises an amino acid sequence chosen from RGDC (SEQ ID. NO:1), RGEC (SEQ ID. NO:2), RGDT (SEQ ID. NO:3), RGDS (SEQ ID. NO:4), LDV (SEQ ID. NO:5), REDV (SEQ ID. NO:6), RGDV (SEQ ID. NO:7), LRGDN (SEQ ID. NO:8), IKVAV (SEQ ID. NO:9), YIGSR (SEQ ID. NO:10), PDSGR (SEQ ID. NO:11), RNIAEIIKDA (SEQ ID. NO:12), RGDT (SEQ ID. NO:13), DGEA (SEQ ID. NO:14), DGEAGC (SEQ ID. NO:15), EPRGDNYR (SEQ ID. NO:16), EILDV (SEQ ID. NO:17), REDV (SEQ ID. NO:18), SIKVAV (SEQ ID. NO:19), RGD (SEQ ID. NO:20), KQAGDV (SEQ ID. NO:21), HRSNRKGV (SEQ ID. NO:22), VTXG (SEQ ID. NO:23), LGPA (SEQ ID. NO:24), and AAAAAAAAA (SEQ ID. NO:25).

13. A peptide-modified polyurethane comprising a reaction product of an isocyanate, a chain extender, and a peptide, wherein the peptide is incorporated into a backbone chain of the peptide-modified polyurethane and wherein the reaction product is chosen from PUU-YIGSR, PUU-PEG-YIGSR, PUU-YIGSR-LGPA, PU-BD-NO, PU-BD-PEG-YIGSR, and PU-BD-PEG-YIGSR-NO.

* * * * *

SEQUENCE LISTING

```
<160> NUMBER OF SEQ ID NOS: 33

<210> SEQ ID NO 1
<211> LENGTH: 4
<212> TYPE: PRT
<213> ORGANISM: Artificial Sequence
<220> FEATURE:
<223> OTHER INFORMATION: natural, artificial, or synthetic sequence

<400> SEQUENCE: 1

Arg Gly Asp Cys
 1

<210> SEQ ID NO 2
<211> LENGTH: 4
<212> TYPE: PRT
<213> ORGANISM: Artificial Sequence
<220> FEATURE:
<223> OTHER INFORMATION: natural, artificial, or synthetic sequence

<400> SEQUENCE: 2
```

Arg Gly Glu Cys
1

<210> SEQ ID NO 3
<211> LENGTH: 4
<212> TYPE: PRT
<213> ORGANISM: Artificial Sequence
<220> FEATURE:
<223> OTHER INFORMATION: natural, artificial, or synthetic sequence

<400> SEQUENCE: 3

Arg Gly Asp Thr
1

<210> SEQ ID NO 4
<211> LENGTH: 4
<212> TYPE: PRT
<213> ORGANISM: Artificial Sequence
<220> FEATURE:
<223> OTHER INFORMATION: natural, artificial, or synthetic sequence

<400> SEQUENCE: 4

Arg Gly Asp Ser
1

<210> SEQ ID NO 5
<211> LENGTH: 3
<212> TYPE: PRT
<213> ORGANISM: Artificial Sequence
<220> FEATURE:
<223> OTHER INFORMATION: natural, artificial, or synthetic sequence

<400> SEQUENCE: 5

Leu Asp Val
1

<210> SEQ ID NO 6
<211> LENGTH: 4
<212> TYPE: PRT
<213> ORGANISM: Artificial Sequence
<220> FEATURE:
<223> OTHER INFORMATION: natural, artificial, or synthetic sequence

<400> SEQUENCE: 6

Arg Glu Asp Val
1

<210> SEQ ID NO 7
<211> LENGTH: 4
<212> TYPE: PRT
<213> ORGANISM: Artificial Sequence
<220> FEATURE:
<223> OTHER INFORMATION: natural, artificial, or synthetic sequence

<400> SEQUENCE: 7

Arg Gly Asp Val
1

<210> SEQ ID NO 8
<211> LENGTH: 5
<212> TYPE: PRT
<213> ORGANISM: Artificial Sequence
<220> FEATURE:
<223> OTHER INFORMATION: natural, artificial, or synthetic sequence

<400> SEQUENCE: 8

Leu Arg Gly Asp Asn

```
<210> SEQ ID NO 9
<211> LENGTH: 4
<212> TYPE: PRT
<213> ORGANISM: Artificial Sequence
<220> FEATURE:
<223> OTHER INFORMATION: natural, artificial, or synthetic sequence

<400> SEQUENCE: 9

Lys Val Ala Val
1

<210> SEQ ID NO 10
<211> LENGTH: 5
<212> TYPE: PRT
<213> ORGANISM: Artificial Sequence
<220> FEATURE:
<223> OTHER INFORMATION: natural, artificial, or synthetic sequence

<400> SEQUENCE: 10

Tyr Ile Gly Ser Arg
1               5

<210> SEQ ID NO 11
<211> LENGTH: 5
<212> TYPE: PRT
<213> ORGANISM: Artificial Sequence
<220> FEATURE:
<223> OTHER INFORMATION: natural, artificial, or synthetic sequence

<400> SEQUENCE: 11

Pro Asp Ser Gly Arg
1               5

<210> SEQ ID NO 12
<211> LENGTH: 10
<212> TYPE: PRT
<213> ORGANISM: Artificial Sequence
<220> FEATURE:
<223> OTHER INFORMATION: natural, artificial, or synthetic sequence

<400> SEQUENCE: 12

Arg Asn Ile Ala Glu Ile Ile Lys Asp Ala
1               5                   10

<210> SEQ ID NO 13
<211> LENGTH: 4
<212> TYPE: PRT
<213> ORGANISM: Artificial Sequence
<220> FEATURE:
<223> OTHER INFORMATION: natural, artificial, or synthetic sequence

<400> SEQUENCE: 13

Arg Gly Asp Thr
1

<210> SEQ ID NO 14
<211> LENGTH: 4
<212> TYPE: PRT
<213> ORGANISM: Artificial Sequence
<220> FEATURE:
<223> OTHER INFORMATION: natural, artificial, or synthetic sequence

<400> SEQUENCE: 14

Asp Gly Glu Ala
1
```

```
<210> SEQ ID NO 15
<211> LENGTH: 6
<212> TYPE: PRT
<213> ORGANISM: Artificial Sequence
<220> FEATURE:
<223> OTHER INFORMATION: natural, artificial, or synthetic sequence

<400> SEQUENCE: 15

Asp Gly Glu Ala Gly Cys
 1               5

<210> SEQ ID NO 16
<211> LENGTH: 8
<212> TYPE: PRT
<213> ORGANISM: Artificial Sequence
<220> FEATURE:
<223> OTHER INFORMATION: natural, artificial, or synthetic sequence

<400> SEQUENCE: 16

Glu Pro Arg Gly Asp Asn Tyr Arg
 1               5

<210> SEQ ID NO 17
<211> LENGTH: 5
<212> TYPE: PRT
<213> ORGANISM: Artificial Sequence
<220> FEATURE:
<223> OTHER INFORMATION: natural, artificial, or synthetic sequence

<400> SEQUENCE: 17

Glu Ile Leu Asp Val
 1               5

<210> SEQ ID NO 18
<211> LENGTH: 4
<212> TYPE: PRT
<213> ORGANISM: Artificial Sequence
<220> FEATURE:
<223> OTHER INFORMATION: natural, artificial, or synthetic sequence

<400> SEQUENCE: 18

Arg Glu Asp Val
 1

<210> SEQ ID NO 19
<211> LENGTH: 6
<212> TYPE: PRT
<213> ORGANISM: Artificial Sequence
<220> FEATURE:
<223> OTHER INFORMATION: natural, artificial, or synthetic sequence

<400> SEQUENCE: 19

Ser Ile Lys Val Ala Val
 1               5

<210> SEQ ID NO 20
<211> LENGTH: 3
<212> TYPE: PRT
<213> ORGANISM: Artificial Sequence
<220> FEATURE:
<223> OTHER INFORMATION: natural, artificial, or synthetic sequence

<400> SEQUENCE: 20

Arg Gly Asp
 1
```

<210> SEQ ID NO 21
<211> LENGTH: 6
<212> TYPE: PRT
<213> ORGANISM: Artificial Sequence
<220> FEATURE:
<223> OTHER INFORMATION: natural, artificial, or synthetic sequence

<400> SEQUENCE: 21

Lys Gln Ala Gly Asp Val
 1               5

<210> SEQ ID NO 22
<211> LENGTH: 8
<212> TYPE: PRT
<213> ORGANISM: Artificial Sequence
<220> FEATURE:
<223> OTHER INFORMATION: natural, artificial, or synthetic sequence

<400> SEQUENCE: 22

His Arg Ser Asn Arg Lys Gly Val
 1               5

<210> SEQ ID NO 23
<211> LENGTH: 4
<212> TYPE: PRT
<213> ORGANISM: Artificial Sequence
<220> FEATURE:
<223> OTHER INFORMATION: natural, artificial, or synthetic sequence
<220> FEATURE:
<221> NAME/KEY: VARIANT
<222> LOCATION: 3
<223> OTHER INFORMATION: Xaa = Any Amino Acid

<400> SEQUENCE: 23

Val Thr Xaa Gly
 1

<210> SEQ ID NO 24
<211> LENGTH: 4
<212> TYPE: PRT
<213> ORGANISM: Artificial Sequence
<220> FEATURE:
<223> OTHER INFORMATION: proteolytically degradable, natural,
      artificial, or synthetic sequence

<400> SEQUENCE: 24

Leu Gly Pro Ala
 1

<210> SEQ ID NO 25
<211> LENGTH: 9
<212> TYPE: PRT
<213> ORGANISM: Artificial Sequence
<220> FEATURE:
<223> OTHER INFORMATION: proteolytically degradable, natural,
      artificial, or synthetic sequence

<400> SEQUENCE: 25

Ala Ala Ala Ala Ala Ala Ala Ala Ala
 1               5

<210> SEQ ID NO 26
<211> LENGTH: 4
<212> TYPE: PRT
<213> ORGANISM: Artificial Sequence
<220> FEATURE:
<223> OTHER INFORMATION: NO binding, natural, artificial, or synthetic
      sequence

```
<400> SEQUENCE: 26

Lys Lys Lys Lys
  1

<210> SEQ ID NO 27
<211> LENGTH: 4
<212> TYPE: PRT
<213> ORGANISM: Artificial Sequence
<220> FEATURE:
<223> OTHER INFORMATION: NO binding, natural, artificial, or synthetic
      sequence
<220> FEATURE:
<221> NAME/KEY: VARIANT
<222> LOCATION: (1)...(4)
<223> OTHER INFORMATION: lysines capable of forming a diazeniumdiolate
      ion
<220> FEATURE:
<223> OTHER INFORMATION: Xaa = Any Amino Acid

<400> SEQUENCE: 27

Xaa Xaa Xaa Xaa
  1

<210> SEQ ID NO 28
<211> LENGTH: 3
<212> TYPE: PRT
<213> ORGANISM: Artificial Sequence
<220> FEATURE:
<223> OTHER INFORMATION: NO binding, natural, artificial, or synthetic
      sequence

<400> SEQUENCE: 28

Cys Cys Cys
  1

<210> SEQ ID NO 29
<211> LENGTH: 12
<212> TYPE: PRT
<213> ORGANISM: Artificial Sequence
<220> FEATURE:
<223> OTHER INFORMATION: natural, artificial, or synthetic sequence

<400> SEQUENCE: 29

Gly Gly Gly Tyr Ile Gly Ser Arg Gly Gly Gly Lys
  1               5                  10

<210> SEQ ID NO 30
<211> LENGTH: 10
<212> TYPE: PRT
<213> ORGANISM: Artificial Sequence
<220> FEATURE:
<223> OTHER INFORMATION: natural, artificial, or synthetic sequence

<400> SEQUENCE: 30

Gly Gly Gly Cys Cys Cys Gly Gly Gly Lys
  1               5                  10

<210> SEQ ID NO 31
<211> LENGTH: 10
<212> TYPE: PRT
<213> ORGANISM: Artificial Sequence
<220> FEATURE:
<223> OTHER INFORMATION: natural, artificial, or synthetic sequence

<400> SEQUENCE: 31

Ser Gly Gly Lys Lys Lys Lys Gly Gly Ser
  1               5                  10
```

```
<210> SEQ ID NO 32
<211> LENGTH: 10
<212> TYPE: PRT
<213> ORGANISM: Artificial Sequence
<220> FEATURE:
<223> OTHER INFORMATION: NO binding, natural, artificial, or synthetic
      sequence
<220> FEATURE:
<221> NAME/KEY: VARIANT
<222> LOCATION: (4)...(7)
<223> OTHER INFORMATION: lysines capable of forming a diazeniumdiolate
      ion
<220> FEATURE:
<223> OTHER INFORMATION: Xaa = Any Amino Acid

<400> SEQUENCE: 32

Ser Gly Gly Xaa Xaa Xaa Xaa Gly Gly Ser
 1               5                  10

<210> SEQ ID NO 33
<211> LENGTH: 11
<212> TYPE: PRT
<213> ORGANISM: Artificial Sequence
<220> FEATURE:
<223> OTHER INFORMATION: proteolyitcally degradable, natural,
      artificial, or synthetic sequence

<400> SEQUENCE: 33

Gly Gly Gly Leu Gly Pro Ala Gly Gly Gly Lys
 1               5                  10
```